(12) United States Patent
Seeley

(10) Patent No.: US 6,410,312 B1
(45) Date of Patent: Jun. 25, 2002

(54) HUBUB3 GENE INVOLVED IN HUMAN CANCERS

(75) Inventor: Todd W. Seeley, Moraga, CA (US)

(73) Assignee: Chiron Corporation, Emeryville, CA (US)

(*) Notice: Subject to any disclaimer, the term of this patent is extended or adjusted under 35 U.S.C. 154(b) by 0 days.

(21) Appl. No.: 09/208,743

(22) Filed: Dec. 10, 1998

Related U.S. Application Data

(60) Provisional application No. 60/068,102, filed on Dec. 19, 1997, provisional application No. 60/070,182, filed on Dec. 30, 1997, and provisional application No. 60/088,991, filed on Jun. 11, 1998.

(51) Int. Cl.[7] .......................... C12N 15/00; C12N 5/00; C12P 21/06; C07H 21/02; C07H 21/05

(52) U.S. Cl. .................. 435/320.1; 435/69.1; 435/325; 435/455; 536/23.1; 536/23.5

(58) Field of Search .............................. 536/23.1, 23.5; 435/320.1, 325, 69.1, 455

(56) References Cited

U.S. PATENT DOCUMENTS

| | | | |
|---|---|---|---|
| 5,283,173 A | 2/1994 | Fields et al. | 435/6 |
| 5,518,911 A | 5/1996 | Abo et al. | 435/194 |

FOREIGN PATENT DOCUMENTS

| | | |
|---|---|---|
| WO | WO 93/19752 | 10/1993 |
| WO | WO 96/09835 | 4/1996 |

OTHER PUBLICATIONS

Kalitsis et al., Bub3 gene disruption in mice reveals essential mitotic spindle checkpoint function during early embryogenesis, 2000, Gene & Development, vol. 14 pp. 2277–2282.*

Taylor et al., The human Homolgue of Bub3 Is Reguired for Kinetochore Localization of Bub1 and a Mad3/Bub1–related Protein Kinase, Jully 1998, The Journal of Cell Biology, vol. 142 pp. 1–11.*

Seeley et al., Phosphorylation of Human MAD1 by the BUB1 Kinase in Vitro, 1999, Biochemical and Biophysical Research Communications, vol. 257 pp. 589–595.*

Martinez–Exposito et al., Retention of the Bub3 checkpoint protein in lagging chromosomes, Jul. 1999, Proc. Natl. Acad. Sci. USA, vol. 96 pp. 8493–8498.*

Downs et al., (Acct. No. U67327), Jan. 1997.*

Database EMBL ID No. HS1249493, AC. No. AA449311, Jun. 10, 1997.

Database EMBL ID No. HS1229812, AC. No. AA430092, May 25, 1997.

Database EMBL ID No./AC. No. P97397, May 1, 1997.

Database EMBL ID No. MMU67327, AC. No. U67327, Jan. 19, 1997.

Hoyt et al., "S. cerevisiae Genes Required For Cell Cycle Arrest in Response to Loss of Microtubule Function," *Cell* 66:507–517, 1991.

Ouyang et al., "Human Bub1: A Putative Spindle Checkpoint Kinase Closley Linked to Cell Proliferation," *Cell Growth & DIfferentiation* 9: 877–855, 1998.

Pangilinan et al., "Mammalian BUB1 Protein Kinases: Map Positions and in Vivo Ezpression," *Genomics* 46: 379–388, 1997.

Roberts et al., "*The Saccharomyces cerevisiae* Checkpoint Gene *BUB1* Encodes a Novel Protein Kinase," *Molecular And Cellular Biology* 14(12): 8282–8290, 1994.

Taylor and McKeon, "Kinetochore Localization of Murine Bub 1 Is Required for Normal Mitotic Timing and Checkpoint Response to Spindle Damage," *Cell* 89: 727–735, 1997.

* cited by examiner

*Primary Examiner*—Scott D. Priebe
*Assistant Examiner*—Sumesh Kaushal
(74) *Attorney, Agent, or Firm*—Jane E. R. Potter; Kimberlin L. Morley; Robert P. Blackburn

(57) ABSTRACT

Methods are provided for assessing mutations and/or loss of the huBUB3 gene in human tumors. Loss of wild-type huBUB3 genes is involved in neoplastic development. Therapeutic regimens can be planned on the basis of the mutational status of huBUB3.

5 Claims, 7 Drawing Sheets

```
GAAGCAAGGAGGCGGCGGCGGCCGAGCGAGTGGCGAGTAGTGGAAACGTTGC
TTCTGAGGGGAGCCCAAGATGACCGGTTCTAACGAGTTCAAGCTGAACCAGCC
ACCCGAGGATGGCATCTCCTCCGTGAAGTTCAGCCCCAACACCTCCCAGTTCCT
GCTTGTCTCCTCCTGGGACACGTCCGTGCGTCTCTACGATGTGCCGGCCAACTCC
ATGCGGCTCAAGTACCAGCACACCGGCGCCGTCCTGGACTGCGCCTTCTACGAT
CCAACGCATGCCTGGAGTGGAGGACTAGATCATCAATTGAAAATGCATGATT
TGAACACTGATCAAGAAAATCTTGTTGGGACCCATGATGCCCCTATCAGATGT
GTTGAATACTGTCCAGAAGTGAATGTGATGGTCACTGGAAGTTGGGATCAGA
CAGTTAAACTGTGGGATCCCAGAACTCCTTGTAATGCTGGGACCTTCTCTCAGC
CTGAAAAGGTATATACCCTCTCAGTGTCTGGAGACCGGCTGATTGTGGGAACA
GCAGGCCGCAGAGTGTTGGTGTGGGACTTACGGAACATGGGTTACGTGCAGCA
GCGCAGGGAGTCCAGCCTGAAATACCAGACTCGCTGCATACGAGCGTTTCCAA
ACAAGCAGGGTTATGTATTAAGCTCTATTGAAGGCCGAGTGGCAGTTGAGTA
TTTGGACCCAAGCCCTGAGGTACAGAAGAAGAAGTATGCCTTCAAATGTCAC
AGACTAAAAGAAAATAATATTGAGCAGATTTACCCAGTCAATGCCATTTCTT
TTCACAATATCCACAATACATTTGCCACAGGTGGTTCTGATGGCTTTGTAAAT
ATTTGGGATCCATTTAACAAAAAGCGACTGTGCCAATTCCATCGGTACCCCAC
GAGCATCGCATCACTTGCCTTCAGTAATGATGGGACTACGCTTGCAATAGCGT
CATCATATATGTATGAAATGGATGACACAGAACATCCTGAAGATGGTATCTT
CATTCGCCAAGTGACAGATGCAGAAACAAAACCCAAGTCACCATGTACTTGA
CAAGATTTCATTTACTTAAGTGCCATGTTGATGATAATAAAACAATTCGTAC
TCCCCAATGGTGGATTTATTACTATTAAAGAAACCAGGGAAAATATTAATTT
TAATATTATAACAACCTGAAAATAATGGAAAAGAGGTTTTTGAATTTTTTTT
TTTAAATAAACACCTTCTTAAGTGCATGAGATGGTTTGATGGTTTGCTGCATT
AAAGGTATTTGGGCAAACAAAATTGGAGGGCAAGTGACTGCAGTTTTGAGA
ATCAGTTTTGACCTTGATGATTTTTTGTTTCCACTGTGGAAATAAATGTTTGTA
AATAAGTGTAATAAAAATCCCTTTGCATTCTTTCTGGACCTTAAATGGTAGA
GGAAAAGGCTCGTGAGCCATTTGTTTCTTTTGCTGGTTATAGTTGCTAATTCTA
AAGCTGCTTCAGACTGCTTCATGAGGAGGTTAATCTACAATTAAACAATATT
TCCTCTTGGCCGTCCATTATTTTCTGAAGCAGATGGTTCATCATTTCCTGGGCTG
TTAAACAAAGCGAGGTTAAGGTTAGACTCTTGGGAATCAGCTAGTTTTCAAT
CTTATTAGGGTGCAGAAGGAAAACTAATAAGAAAACCTCCTAATATCATTTT
GTGACTGTAAACAATTATTTATTAGCAAACAATTGATCCCAGAAGGGCAAAT
TGTTTGAGTCAGTAATGAGCTGAGAAAAGACAGAGCATATCTGTGTATTTGG
AAAAATAATTGTAACGTAATTGCAGTGCATTTAGACAGGCATCTATTTGGAC
CTGTTTCTATCTCTAAATGAATTTTTGGAAACATTAATGAGGTTTACATATTT
CTCTGACATTTATATAGTTCTTATGTCCATTTCAGTTGACCAGCCGCTGGTGAT
TAAAGTTAAAAAGAAAAAAATTATAGTGAGAATGAGATTCATTTCAATGTA
ATGCACTAAAGCAGAACACGAACTTAGCTTGGCCTATTCTAGGTAGTTCCAA
ATAGTATTTTTGTTGTCAAACTTTAAAATTTATATTAATTTGCAAATGTATGT
CTCTGAGTAGGACTTGGACCTTTCCTGAGATTTATTTTATCCGTGATGTATTTT
TTTTAATTCTTTTGATACAGAGAAGGGTCTTTTTTTTTTTAAGTATTTCAGTGA
AAACTTGGTGTAAGTCTGAACCCATCTTTTGAAATGTATTTTCTTCATTGCAG
```

*Fig. 1B*

```
GTCCACCTAATCATCCTGTGAAAGTGGTTTCTCTATGGAAAGCTTTGTTTGCTT
CCTACAAATACATGCTTATTCCTTAAGGGATGTGTTAGAGTTACTGTGGATTT
CTCTGTTTTCTGTCTTACAAGAAACTTGTCTATGTACCTTAATACTTTGTTTAG
GATGAGGAGTCTTTGTGTCCCTGTACAGTAGTCTGACGTATTTCCCCTTCTGTC
CCCTAGTAAGCCCAGTTGCTGTATCTGAACAGTTTGAGCTCTTTTTGTAATATA
CTCTAAACCTGTTATTTCTGTGCTAATAAACGAGATGCAGAACCCTTGAAAA
AAAAAAAAAAAAAAAAAAAAAAAAAAAAAAA
```

Fig. 1B
(Continued)

Alignment of predicted huBUB3 gene products from ~1.4 Kb cDNA and ~2.7 Kb cDNA

```
                      20              40              60
huBUB3 2.7   MTGSNEFKLNQPPEDGISSVKFSPNTSQFLLVSSWDTSVRLYDVPANSMRLKYQHTGAVL
huBUB3 1.4   MTGSNEFKLNQPPEDGISSVKFSPNTSQFLLVSSWDTSVRLYDVPANSMRLKYQHTGAVL 80             100             120
huBUB3 2.7   DCAFYDPTHAWSGGLDHQLKMHDLNTDQENLVGTHDAPIRCVEYCPEVNVMVTGSWDQTV
huBUB3 1.4   DCAFYDPTHAWSGGLDHQLKMHDLNTDQENLVGTHDAPIRCVEYCPEVNVMVTGSWDQTV 140             160             180
huBUB3 2.7   KLWDPRTPCNAGTFSQPEKVYTLSVSGDRLIVGTAGRRVLVWDLRNMGYVQQRRESSLKY
huBUB3 1.4   KLWDPRTPCNAGTFSQPEKVYTLSVSGDRLIVGTAGRRVLVWDLRNMGYVQQRRESSLKY 200             220             240
huBUB3 2.7   QTRCIRAFPNKQGYVLSSIEGRVAVEYLDPSPEVQKKKYAFKCHRLKENNIEQIYPVNAI
huBUB3 1.4   QTRCIRAFPNKQGYVLSSIEGRVAVEYLDPSPEVQKKKYAFKCHRLKENNIEQIYPVNAI 260             280             300
huBUB3 2.7   SFHNIHNTFATGGSDGFVNIWDPFNKKRLCQFHRYPTSIASLAFSNDGTTLAIASSYMYE
huBUB3 1.4   SFHNIHNTFATGGSDGFVNIWDPFNKKRLCQFHRYPTSIASLAFSNDGTTLAIASSYMYE 320
huBUB3 2.7   MDDTEHPEDGIFIRQVTDAETKPKSPCT
huBUB3 1.4   MDDTEHPEDGIFIRQVTDAETKPKVHLIIL
```

Fig. 2

Alignment of related proteins scBUB3, muBUB3, huBUB3 (2.7), hu-rae1,
rae-1 (*Schizosaccharomyces pombe*), scYET7. scBUB3, hu-rae-1, sp-rae1 and scYET7
sequences were obtained from Genbank. The murine sequence is derived from
Genbank entry U67327, corrected using overlapping murine EST entries for a
reading frame error which truncated the predicted reading frame at the C-terminus.
Predicted WD40 repeat regions are indicated with roman numerals. Conserved
residues are indicated below the alignments.

```
scBUB3    1  ---------------------------MQIVQIEQAPKDYISDIKIIP---SKSLLL   27
muBUB3    1  --------------------MTG-------SNEFKLNQPPEDGISSVKFSPN--TSQFLL   31
huBUB3    1  --------------------MTG-------SNEFKLNQPPEDGISSVKFSPN--TSQFLL   31
rael-hu   1  MSLFGTTSGFGTSGTSMFGSATT--DNHNPMKDIEVTSSPDDSIGCLSFSPPTLPGNFLI   58
rae1      1  MSLFG------QATTSTVSNATG-----DLKKDVEVAQPPEDSISDLAFSP---QAEYLA   46
yet7      1  MSFFNR-----SNTTSALGTSTAMANEKDLANDIVINSPAEDSISDIAFSP---QQDFMF   52
                                                              .  D I . P ———I———                              ———II—
scBUB3   28  -ITSWDGSLTVYKFDIQAKNVDLLQSLRYKH--PLLCCNFI-DNTDLQIYVGTVQGEILK   83
muBUB3   32  -VSSWDT--SVRLYDVPA--NSM-R-LKYQHTGAVLDCAFY-DPT---HAWSGGLDHQLKM   81
huBUB3   32  -VSSWDT--SVRLYDVPA--NSM-R-LKYQHTGAVLDCAFY-DPT---HAWSGGLDHQLKM   81
rael-hu  59  -AGSWAN--DVRCWEVQDSGQTIPK-AQQMHTGPVLDVCWSDDGS--KVFTASCDKTAKM  112
rae1     47  -ASSWDS--KVRIYEVQATGQSIGK-ALYEHQGPVLSVNWSRDGT--KVASGSVDKSAKV  100
yet7     53  SASSWDG--KVRIWDVQN-GVPQGR-AQHESSSPVLCTRWSNDGT--KVASGGCDNALKL  106
                  SW      V    ..         .           .L         D . .

———III———
scBUB3   84  VDLIGSPSFQALTNNEANLGICRICKYGD--DKLIAASWDGLIEVIDPRNYGDGVIAVKN  141
muBUB3   82  HDLNTDQENLVGTHDAPIRCVEYCPEVNV----MVTGSWDQTVKLWDPR-TPCNAGTFS-  135
huBUB3   82  HDLNTDQENLVGTHDAPIRCVEYCPEVNV----MVTGSWDQTVKLWDPR-TPCNAGTFS-  135
rael-hu 113  WDLSSNQAIQIAQHDAPVKTIHWIKAPNY--SCVMTGSWDKTLKFWDTR-SSNPMMVLQ-  168
rae1    101  FDIQTGQNQQVAAHDDAVRCVRFVEAMGT-SPILATGSWDKTLKYWDLR-QSTPIATVS-  157
yet7    107  YDIASGQTQQIGMHSAPIKVLRFVQCGPSNTECIVTGSWDKTIKYWDMR-QPQPVSTVM-  164
              D.             .           . .       ..SWD .  D R ———IV———
scBUB3  142  LNSNNTKVKNKIFTMDTNSSRLIVGMNNSQVQWFRLPLCEDDNGTIEESGLKYQIRDVAL  201
muBUB3  136  Q-------PEKVYTLSVSGDRLIVGTAGRRVLVWDLWNMGYVQQRRE-SSLKYQTRCIRA  187
huBUB3  136  Q-------PEKVYTLSVSGDRLIVGTAGRRVLVWDLRNMGYVQQRRE-SSLKYQTRCIRA  187
rael-hu 169  L-------PERCYCADVIYPMAVVATAERGLIVYQLENQPSEFRRIE-SPLKHQHRCVAI  220
rae1    158  L-------PERVYAMDCVHPLLTVATAERNICVINLSEPTKIFKLAM-SPLKFQTRSLAC  209
yet7    165  M-------PERVYSMDNKQSLLVVATAERHIAIINLANPTTIFKATT-SPLKWQTRCVAC  216
                . ..              V         .   L           S LK Q R .
```

*Fig. 3A*

```
                     ———V———
scBUB3   202  LP---KEQEGYACSSIDGRVAVEFFDDQGDDYNSSKRFAFRCHRLNLKD-TNL-------  250
muBUB3   188  FP---NK-QGYVLSSIEGRVAVEYLDPS-PEV-QKKKYAFKCHRLKENN-IEQ-------  233
huBUB3   188  FP---NK-QGYVLSSIEGRVAVEYLDPS-PEV-QKKKYAFKCHRLKENN-IEQ-------  233
rae1-hu  221  FKDKQNKPTGFALGSIEGRVAIHYINPP-NP--AKDNFTFKCHRSNGTNTSAP-----QD  272
rae1     210  F----IKGDGYAIGSVEGRCAIQNIDE--KN--ASQNFSFRCHRNQAGN-SAD-------  253
yet7     217  Y----NEADGYAIGSVEGRCSIRYIDDG-MQ--KKSGFSFKCHRQTNPN-RAPGSNGQSL  268
              G.    S..GR ..               ..F.CHR ———VI———
scBUB3   251  AYPVNSIEFSPRHKFLYTAGSDGIISCWNLQTRKKIKNFAKFNED-SVVKIACSDNILCL  309
muBUB3   234  IYPVNAISFHNIHNTFATGGSDGFVNIWDPFNKKRLCQFHRYPTSIASLAFSNDGTTLAI  293
huBUB3   234  IYPVNAISFHNIHNTFATGGSDGFVNIWDPFNKKRLCQFHRYPTSIASLAFSNDGTTLAI  293
rae1-hu  273  IYAVNGIAFHPVHGTLATVGSDGRFSFWDKDARTKLKTSEQLDQPISACCFNHNGNIFAY  332
rae1     254  VYSVNSIAFHPQYGTFSTAGSDGTFSFWDKDSHQRLKSYPNVGGTISCSTFNRTGDIFAY  313
yet7     269  VYPVNSIAFHPLYGTFVTAGGDGTFNFWDKNQRHRLKGYPTLQASIPVCSFNRNGSVFAY  328
              Y VN I F       T G DG   W       ...

scBUB3   310  ATSDDTFKTNAAIDQTIELNASSIYIIFDYEN--------  341
muBUB3   294  ASSYMYEMDDT-EHPE---DGIFIRQVTDAETKPKS---T  326
huBUB3   294  ASSYMYEMDDT-EHPE---DGIFIRQVTDAETKPKSPC-T  328
rae1-hu  333  ASSYDWSKGHEFYNPQKK-NYIFLRNA-AEELKPRNKK--  368
rae1     314  AISYDWSKGYTFNNAQLP-NKIMLHPVPQDEIKPRPKKGR  352
yet7     329  ALSYDWHQGHMGNRPDYP-NVIRLHATTDEEVKEK-KK-R  365
              A S                  .         E
```

*Fig. 3B*

HUBUB3 GENE INVOLVED IN HUMAN CANCERS

This application claims the benefit of U.S. Provisional Patent Application No. 60/068,102 filed Dec. 19, 1997; U.S. Provisional Patent Application No. 60/070,182 filed Dec. 30, 1997 and U.S. Provisional Patent Application No. 60/088,991 filed Jun. 11, 1998, where these four provisional applications are incorporated herein by reference in their entireties.

TECHNICAL AREA OF THE INVENTION

The invention relates to the area of cancer diagnostics. More particularly, the invention relates to detection of the loss and or alteration of wild-type huBUB3 genes in tumor tissues.

BACKGROUND OF THE INVENTION

Genes and proteins involved in cell cycle regulation and apoptosis have been found to be important in the development of cancers. There is a continuing need in the art for identification of components of cells which control the cell cycle and apoptosis. These components can be used both diagnostically and therapeutically to identify and detect neoplasms as well as to treat them.

SUMMARY OF THE INVENTION

It is an object of the present invention to provide methods and tools for diagnosing and treating neoplasia. These and other objects of the invention are provided by one or more of the embodiments which are described below.

One embodiment of the invention is an isolated and purified huBUB3 protein having an amino acid sequence which is at least 85% identical to SEQ ID NO:2. Percent identity is determined using a Smith-Waterman homology search algorithm using an affine gap search with a gap open penalty of 12 and a gap extension penalty of 1.

Another embodiment of the invention is an isolated and purified polypeptide comprising at least 8 contiguous amino acids as shown in SEQ ID NO:2.

Even another embodiment of the invention is a huBUB3 fusion protein comprising a first protein segment and a second protein segment fused together by means of a peptide bond. The first protein segment consists of at least 8 contiguous amino acids of a huBUB3 protein as shown in SEQ ID NO:2.

Still another embodiment of the invention is a preparation of antibodies which specifically bind to a huBUB3 protein having an amino acid sequence as shown in SEQ ID NO:2.

A further embodiment of the invention is a cDNA molecule which encodes a huBUB3 protein having an amino acid sequence which is at least 85% identical to SEQ ID NO:2. Percent identity is determined using a Smith-Waterman homology search algorithm using an affine gap search with a gap open penalty of 12 and a gap extension penalty of 1.

Yet another embodiment of the invention is a cDNA molecule which encodes at least 8 contiguous amino acids of SEQ ID NO:2.

Another embodiment of the invention is a cDNA molecule comprising at least 12 contiguous nucleotides of SEQ ID NO:1.

Still another embodiment of the invention is a cDNA molecule which is at least 85% identical to the nucleotide sequence shown in SEQ ID NO:1. Percent identity is determined using a Smith-Waterman homology search algorithm using an affine gap search with a gap open penalty of 12 and a gap extension penalty of 1.

Even another embodiment of the invention is an isolated and purified subgenomic polynucleotide comprising a nucleotide sequence which hybridizes to SEQ ID NO:1 after washing with 0.2×SSC at 65° C. The nucleotide sequence encodes a huBUB3 protein having the amino acid sequence of SEQ ID NO:2.

Yet another embodiment of the invention is a construct comprising a promoter and a polynucleotide segment encoding at least 8 contiguous amino acids of a huBUB3 protein as shown in SEQ ID NO:2. The polynucleotide segment is located downstream from the promoter. Transcription of the polynucleotide segment initiates at the promoter.

Even another embodiment of the invention is a host cell comprising a construct which comprises a promoter and a polynucleotide segment encoding at least 8 contiguous amino acids of a huBUB3 protein having an amino acid sequence as shown in SEQ ID NO:2.

A further embodiment of the invention is a recombinant host cell comprising a new transcription initiation unit. The new transcription initiation unit comprises in 5' to 3' order an exogenous regulatory sequence, an exogenous exon, and a splice donor site. The new transcription initiation unit is located upstream of a coding sequence of a huBUB3 gene as shown in SEQ ID NO:1. The exogenous regulatory sequence controls transcription of the coding sequence of the huBUB3 gene.

Still another embodiment of the invention is a pair of single stranded DNA primers. The set allows synthesis of all or part of a huBUB3 gene coding sequence.

Yet another embodiment of the invention is a nucleic acid probe complementary to a wild-type huBUB3 gene as shown in SEQ ID NO:1.

Even another embodiment of the invention is a method of diagnosing a neoplastic tissue of a human. Loss of a wild-type huBUB3 gene or an expression product of the wild-type huBUB3 gene from a tissue suspected of being neoplastic is detected. The wild-type huBUB3 gene has the coding sequence shown in SEQ ID NO:1. The loss indicates neoplasia of the tissue.

Another embodiment of the invention is a method of identifying a neoplastic tissue of a human. Expression of a first huBUB3 gene in a first tissue of a human suspected of being neoplastic is compared with expression of a second huBUB3 gene in a second tissue of the human which is normal. The second huBUB3 gene has the coding sequence shown in SEQ ID NO:1. Decreased expression of the first huBUB3 gene relative to the second huBUB3 gene identifies the first tissue as being neoplastic.

Still another embodiment of the invention is a method to aid in the diagnosis or prognosis of neoplasia in a human. A first huBUB3 gene, mRNA, or protein in a first tissue of a human suspected of being neoplastic is compared with a second huBUB3 gene, mRNA, or protein in a second tissue of a human which is normal. The second huBUB3 gene has the coding sequence shown in SEQ ID NO:1. A difference between the first and second huBUB3 genes, mRNAs, or proteins indicates the presence of neoplastic cells in the first tissue.

Even another embodiment of the invention is a method to aid in detecting a genetic predisposition to neoplasia in a human. A huBUB3 gene, mRNA, or protein in the fetal tissue of a human is compared with a wild-type huBUB3 gene, mRNA, or protein. The wild-type huBUB3 gene has the coding sequence shown in SEQ ID NO:1. A difference between the huBUB3 gene, mRNA, or protein in the fetal tissue of the human and the wild-type huBUB3 gene, mRNA, or protein indicates a genetic predisposition to neoplasia in the human.

Yet another embodiment of the invention is a method of screening test compounds for the ability to interfere with the binding of a huBUB3 protein to a huBUB1 protein. A test compound is contacted with at least a huBUB3-binding domain of a huBUB1 protein as shown in SEQ ID NO:4 and at least a huBUB1-binding domain of a huBUB3 protein as shown in SEQ ID NO:2. The huBUB3-binding domain binds to the huBUB1-binding domain in the absence of the test compound. The amount of the huBUB1-binding domain which is bound or unbound to the huBUB3-binding domain or the amount of the huBUB3-binding domain which is bound or unbound to the huBUB1-binding domain in the presence of the test compound is determined. A test compound which decreases the amount of bound huBUB1- or huBUB3-binding domains or which increases the amount of unbound huBUB1- and huBUB3-binding domains is a potential inducer of mitosis or cell cycle progression.

Even another embodiment of the invention is a method of screening test compounds for the ability to interfere with the binding of a huBUB1 protein to a huBUB3 protein. A cell is with a test compound. The cell comprises a first fusion protein, a second fusion protein, and a reporter gene. The first fusion protein comprises (1) at least a huBUB1-binding domain of a huBUB3 protein as shown in SEQ ID NO:2 and (2) either a DNA binding domain or a transcriptional activating domain. The second fusion protein comprises at least a huBUB3-binding domain of a huBUB1 protein as shown in SEQ ID NO:4. The huBUB1-binding domain binds to the huBUB3-binding domain. If the first fusion protein comprises a DNA binding domain, then the second fusion protein comprises a transcriptional activating domain. If the first fusion protein comprises a transcriptional activating domain, then the second fusion protein comprises a DNA binding domain. The interaction of the first and second fusion proteins reconstitutes a sequence-specific transcription activating factor. The reporter gene comprises a DNA sequence to which the DNA binding domain specifically binds. Expression of the reporter gene is measured. A test compound which decreases the expression of the reporter gene is a potential inducer of mitosis or cell cycle progression.

Another embodiment of the invention is a method of identifying compounds which interfere with the binding of a huBUB3 protein to a huBUB1 protein. A cell which comprises three recombinant DNA constructs is provided. A first construct encodes a first polypeptide fused to a sequence-specific DNA-binding domain, a second construct encodes a second polypeptide fused to a transcriptional activation domain, and a third construct comprises a reporter gene downstream from a DNA element which is recognized by the sequence-specific DNA-binding domain. The first polypeptide comprises a huBUB1-binding domain of a huBUB3 protein as shown in SEQ ID NO:2 and the second polypeptide comprises a huBUB3-binding domain of a huBUB1 protein as shown in SEQ ID NO:4 or the first polypeptide comprises a huBUB3-binding domain of a huBUB1 protein as shown in SEQ ID NO:4 and the second polypeptide comprises a huBUB1-binding domain of a huBUB3 protein as shown in SEQ ID NO:2. The cell is contacted with a test compound. Expression of the reporter gene in the presence of the test compound is determined. A test compound which decreases expression of the reporter gene is identified as a candidate therapeutic agent.

Yet another embodiment of the invention is a cell which comprises three recombinant DNA constructs. A first construct encodes a first polypeptide fused to a sequence-specific DNA-binding domain, a second construct encodes a second polypeptide fused to a transcriptional activation domain, and a third construct comprises a reporter gene downstream from a DNA element which is recognized by the sequence-specific DNA-binding domain. The first polypeptide comprises a huBUB1-binding domain of a huBUB3 protein as shown in SEQ ID NO:2 and the second polypeptide comprises a huBUB3-binding domain of a huBUB1 protein as shown in SEQ ID NO:4, or the first polypeptide comprises a huBUB3-binding domain of a huBUB1 protein as shown in SEQ ID NO:4 and the second polypeptide comprises a huBUB1-binding domain of a huBUB3 protein as shown in SEQ ID NO:2.

Even another embodiment of the invention is a method of determining the quantity of huBUB1 which binds to huBUB3, or of huBUB3 which binds to huBUB1. A first protein and a second protein are contacted. If the first protein is huBUB3 then the second protein is huBUB1 and if the first protein is huBUB1 the second protein is huBUB3. The quantity of the first protein which is bound to the second protein is determined.

Still another embodiment of the invention is a method for identifying compounds which decrease the kinase activity of a huBUB1–huBUB3 complex. A huBUB1–huBUB3 complex is contacted with a test compound. The kinase activity of the huBUB1–huBUB3 complex is determined. A compound which decreases kinase activity of the huBUB1–huBUB3 complex is identified as a candidate therapeutic agent.

The present invention thus provides the art with the sequence of the human BUB3 gene and protein. This information allows highly specific assays to be done to assess the neoplastic status of a particular tumor tissue.

BRIEF DESCRIPTION OF THE DRAWINGS

FIG. 2. Alignment of predicted huBUB3 gene products from ~1.4 kb cDNA and (SEQ ID NO:27 ) and ~2.7 kb cDNA (SEQ ID NO:2).

FIG. 3. Alignment of related proteins scBUB3 (SEQ ID NO:28), muBUB3 (SEQ ID NO:29), huBUB3 (2.7 SEQ ID NO:2), hu-rae1 (SEQ ID NO:30), rae-1 (*Schizosaccharomyces pombe*; SEQ ID NO:31), scYET7 (SEQ ID NO:31), scBUB7 (SEQ ID NO:32). scBUB3, hu-rae1, sp-rae1 and scYET7 sequences were obtained from Genbank. The murine sequence is derived from Genbank entry U67327, corrected using overlapping murine EST entries for a reading frame error which truncated the predicted reading frame at the N-terminus. Predicted WD40 repeat regions are indicated with roman numerals. Conserved residues are indicated below the alignments.

DETAILED DESCRIPTION

Figure 1A:
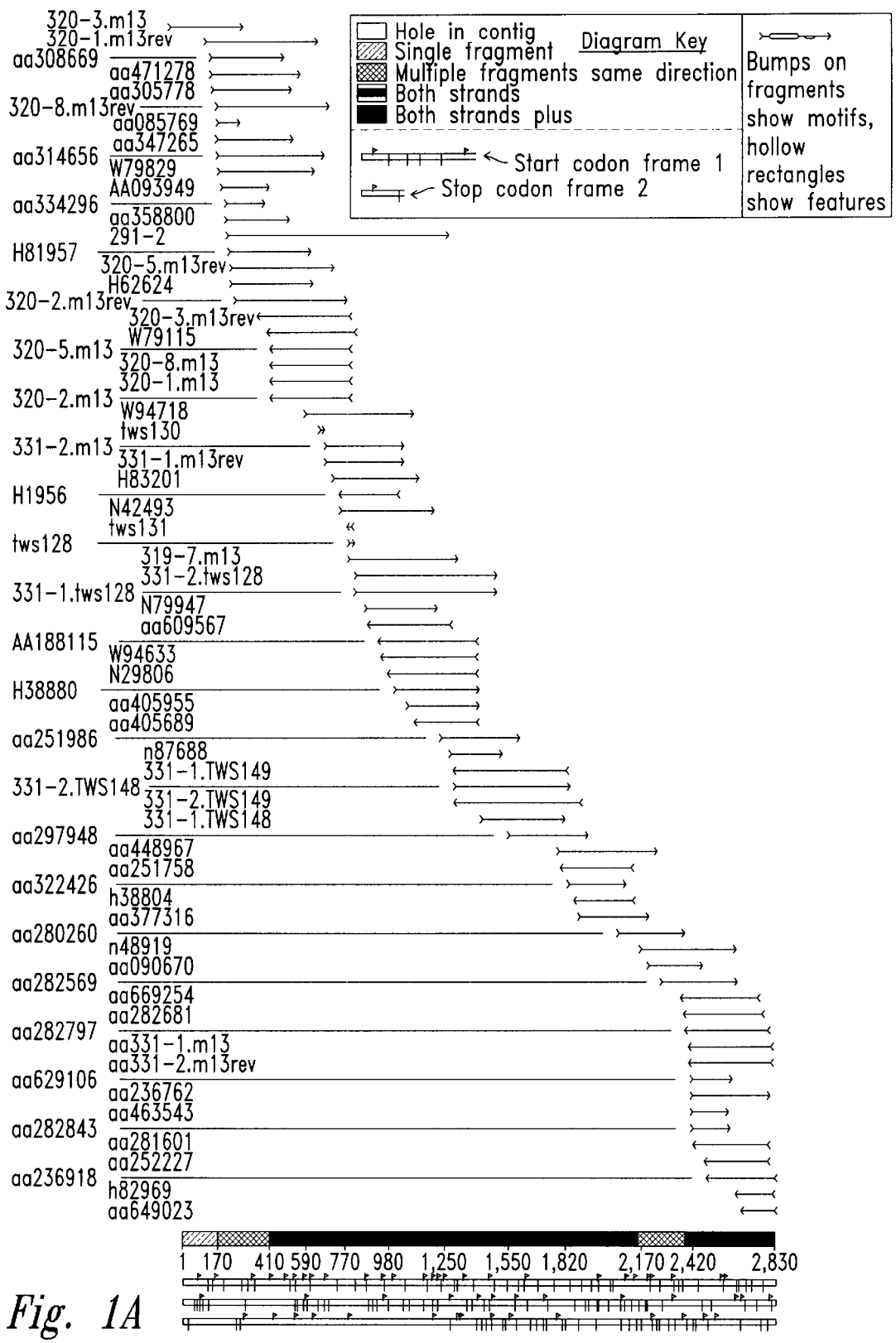
FIG. 1. Compiled huBUB3 ~2.7 kb cDNA sequence. (A) ESTs and experimentally determined sequence data are arrayed relative to the final cDNA sequence, along with the annealing positions of some of the primers described in the text. (B) Nucleotide sequence data describing huBUB3 ~2.7 kb cDNA. By omitting DNA sequence between the exon junctions CCAAG|TCACC (SEQ ID NO:16) and TGCAG|GTCCA (SEQ ID NO:17), this sequence also describes the ~1.4 kb huBUB3 cDNA sequence (see text).

It is a discovery of the present invention that the human BUB3 protein (huBUB3) is involved in cell cycle control and apoptosis. huBUB3 protein also binds to a human BUB1 (huBUB1) protein, and this complex has kinase activity. The huBUB3 gene has the coding sequence shown in SEQ ID NO:1. Mutations in huBUB3 are diagnostic of neoplasia. In addition, the mutational status of huBUB3 can be determined to indicate which chemotherapeutic regimes should be used. For example, because wild-type huBUB3 confers resistance to microtubule poisons such as vincristine, vinblastine, taxol, and taxotere, the finding of a mutation in huBUB3 will indicate that these agents can be used efficaciously. In contrast, finding a wild-type huBUB3 will suggest the use of other agents.

A huBUB3 protein has the amino acid sequence shown in SEQ ID NO:2. huBUB3 polypeptides differ in length from full-length huBUB3 and contain 6, 8, 10, 12, 15, 18, 20, 25, 30, 35, 40, 45, 50, 75, 80, 90, 100, 125, 150, 175, 200, 225, 250, or 275 or more contiguous amino acids of a huBUB3 protein.

Variants of huBUB3 protein and huBUB3 polypeptides can also occur. Biologically active variants of full-length huBUB3 bind to huBUB1. huBUB3 variants can be naturally or non-naturally occurring. Naturally occurring huBUB3 variants are found in humans or other species and comprise amino acid sequences which are substantially identical to the amino acid sequence shown in SEQ ID NO:2. Species homologs of huBUB3 can be obtained using huBUB3 subgenomic polynucleotides of the invention, described below, to make suitable probes or primers to screening cDNA expression libraries from other species, such as mice, monkeys, yeast, or bacteria, identifying cDNAs which encode homologs of huBUB3, and expressing the cDNAs as is known in the art.

Non-naturally occurring huBUB3 variants which retain substantially the same biological activities, such as the ability to bind to huBUB1, as naturally occurring huBUB3 variants are also included here. Preferably, naturally or non-naturally occurring huBUB3 variants have amino acid sequences which are at least 85%, 90%, or 95% identical to amino acid sequences shown in SEQ ID NO:2. More preferably, the molecules are at least 98% or 99% identical. Percent identity between a putative huBUB3 variant and the amino acid sequence of SEQ ID NO:2 is determined using the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* (1981) 2:482–489.

Guidance in determining which amino acid residues can be substituted, inserted, or deleted without abolishing biological or immunological activity can be found using computer programs well known in the art, such as DNASTAR software. Preferably, amino acid changes in huBUB3 variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting huBUB3 variant.

Whether an amino acid change results in a functional huBUB3 protein or polypeptide can readily be determined by assaying its ability to bind to huBUB1 and the ability of the huBUB3–huBUB1 complex to phosphorylate a substrate such as huBUB1, huBUB3, or histone H1. Other in vitro kinase substrates, such as myelin basic protein, casein, and myosin light chain, can also be used. In vitro kinase assays are taught, for example, in WO 96/36642, which is incorporated herein by reference. Binding of a huBUB3 variant to huBUB1 can be detected, for example, using specific antibodies, which are disclosed herein.

huBUB3 variants include glycosylated forms of huBUB3, aggregative conjugates of huBUB3 with other molecules, and covalent conjugates of huBUB3 with unrelated chemical moieties. Covalent variants can be prepared by linking functionalities to groups which are found in the amino acid chain or at the N- or C-terminal residue, as is known in the art. huBUB3 variants also include allelic variants, species variants, and muteins. Truncations or deletions of regions which do not affect the binding of huBUB3 to huBUB1 are also huBUB3 variants.

A subset of mutants, called muteins, is a group of polypeptides in which neutral amino acids, such as serines, are substituted for cysteine residues which do not participate in disulfide bonds. These mutants may be stable over a broader temperature range than native huBUB3. See Mark et al., U.S. Pat. No. 4,959,314.

huBUB3 can be extracted from huBUB3-producing human cells, such as spleen, thymus, prostate, testis, small intestine, colon, peripheral blood lymphocytes, heart, brain, placenta, lung, liver, skeletal muscle, kidney, or pancreas using standard biochemical methods. These methods include, but are not limited to, size exclusion chromatography, ammonium sulfate fractionation, ion exchange chromatography, affinity chromatography, crystallization, electrofocusing, and preparative gel electrophoresis. An isolated and purified huBUB3 protein or polypeptide is separated from other compounds which normally associate with a huBUB3 protein or polypeptide in a cell, such as certain proteins, carbohydrates, lipids, or subcellular organelles. A preparation of isolated and purified huBUB3 proteins or polypeptides is at least 80% pure; preferably, the preparations are 90%, 95%, or 99% pure. Purity of the preparations can be assessed by any means known in the art, such as SDS-polyacrylamide gel electrophoresis.

huBUB3 proteins, polypeptides, and variants can also be produced by recombinant DNA methods or by synthetic chemical methods. For production of recombinant huBUB3 proteins, polypeptides, or variants, coding sequences selected from the huBUB3 nucleotide sequence shown in SEQ ID NO:1, or variants of that sequence which encode huBUB3 protein, can be expressed in known prokaryotic or eukaryotic expression systems (see below). Bacterial, yeast, insect, or mammalian expression systems can be used, as is known in the art.

Alternatively, synthetic chemical methods, such as solid phase peptide synthesis, can be used to synthesize a huBUB3 protein or polypeptide. General means for the production of peptides, analogs or derivatives are outlined in CHEMISTRY AND BIOCHEMISTRY OF AMINO ACIDS, PEPTIDES, AND PROTEINS—A SURVEY OF RECENT DEVELOPMENTS, B. Weinstein, (1983). Substitution of D-amino acids for the normal L-stereoisomer can be carried out to increase the half-life of the molecule. huBUB3 variants can be similarly produced.

Fusion proteins comprising at least 6, 8, 10, 12, 15, 18, 20, 25, 50, 60, 75, 80, 90, 100, 125, 150, 175, 200, 225, 250, or 275 or more contiguous huBUB3 amino acids can also be constructed. huBUB3 fusion proteins are useful for generating antibodies against huBUB3 amino acid sequences and for use in various assay systems. For example, huBUB3 fusion proteins can be used to identify proteins which interact with huBUB3 protein or which interfere with the binding of huBUB3 to huBUB1. Physical methods, such as protein affinity chromatography, or library-based assays for protein-protein interactions, such as the yeast two-hybrid or phage display systems, can also be used for this purpose. Such methods are well known in the art and can also be used as drug screens.

A huBUB3 fusion protein comprises two protein segments fused together by means of a peptide bond. The first protein segment comprises at least 6, 8, 10, 12, 15, 18, 20, 25, 30, 35, 40, 50, 60, 75, 80, 90, 100, 125, 150, 175, 200, 225, 250, or 275 or more contiguous amino acids of a huBUB3 protein. For example, a huBUB3 fusion protein can comprise the huBUB1 binding site. huBUB3 amino acids can be selected from the amino acid sequence shown in SEQ ID NO:2 or from a biologically active variant of that sequence, such as those described above. The first protein segment can also comprise full-length huBUB3.

The second protein segment can be a full-length protein or a protein fragment or polypeptide. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions.

These fusions can be made, for example, by covalently linking two protein segments or by standard procedures in the art of molecular biology. Recombinant DNA methods can be used to prepare huBUB3 fusion proteins, for example, by making a DNA construct which comprises coding sequences selected from SEQ ID NO:1 in proper reading frame with nucleotides encoding the second protein segment and expressing the DNA construct in a host cell, as is known in the art. Many kits for constructing fusion proteins are available from companies that supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-4 888-DNA-KITS).

Isolated and purified huBUB3 proteins, polypeptides, variants, or fusion proteins can be used as immunogens, to obtain preparations of antibodies which specifically bind to huBUB3 protein. The antibodies can be used, inter alia, to detect wild-type huBUB3 protein or huBUB3–huBUB1 complexes in human tissue and fractions thereof The antibodies can also be used to detect the presence of mutations in the huBUB3 gene which result in under- or over-expression of a huBUB3 protein or in expression of a huBUB3 protein with altered size or electrophoretic mobility. Antibodies which specifically bind to huBUB3 protein can be similarly used and prepared, as described below for huBUB3 antibodies.

Any type of antibody known in the art can be generated to bind specifically to huBUB3 epitopes. For example, preparations of polyclonal and monoclonal antibodies can be made using standard methods which are well known in the art. Similarly, single-chain antibodies can also be prepared. Single-chain antibodies which specifically bind to huBUB3 epitopes can be isolated, for example, from single-chain immunoglobulin display libraries, as is known in the art. The library is "panned" against huBUB3 amino acid sequences, and a number of single chain antibodies which bind with high-affinity to different epitopes of huBUB3 protein can be isolated. Hayashi et al., 1995, *Gene* 160:129–30. Single-chain antibodies can also be constructed using a DNA amplification method, such as the polymerase chain reaction (PCR), using hybridoma cDNA as a template. Thirion et al., 1996, *Eur. J. Cancer Prev.* 5:507–11.

Single-chain antibodies can be mono- or bispecific, and can be bivalent or tetravalent. Construction of tetravalent, bispecific single-chain antibodies is taught, for example, in Coloma and Morrison, 1997, *Nat. Biotechnol.* 15:159–63. Construction of bivalent, bispecific single-chain antibodies is taught inter alia in Mallender and Voss, 1994, *J. Biol. Chem.* 269:199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology. Verhaar et al., 1995, *Int. J. Cancer* 61:497–501; Nicholls et al., 1993, *J. Immunol. Meth.* 165:81–91.

Monoclonal and other antibodies can also be "humanized" in order to prevent a patient from mounting an immune response against the antibody when it is used therapeutically. Such antibodies may be sufficiently similar in sequence to human antibodies to be used directly in therapy or may require alteration of a few key residues. Sequence differences between, for example, rodent antibodies and human sequences can be minimized by replacing residues which differ from those in the human sequences, for example, by site directed mutagenesis of individual residues, or by grating of entire complementarity determining regions. Alternatively, one can produce humanized antibodies using recombinant methods, as described in GB2188638B. Antibodies which specifically bind to huBUB3 epitopes can contain antigen binding sites which are either partially or fully humanized, as disclosed in U.S. Pat. No. 5,565,332.

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, can also be prepared.

Antibodies of the invention can be purified by methods well known in the art. For example, antibodies can be affinity purified by passing the antibodies over a column to which a huBUB3 protein, polypeptide, variant, or fusion protein is bound. The bound antibodies can then be eluted from the column, using a buffer with a high salt concentration.

huBUB3-specific antibodies specifically bind to epitopes present in a full-length huBUB3 protein having the amino acid sequence shown in SEQ ID NO:2, to huBUB3 polypeptides, or to huBUB3 variants, either alone or as part of a fusion protein. Preferably, huBUB3 epitopes are not present in other human proteins. Typically, at least 6, 8, 10, or 12 contiguous amino acids are required to form an epitope. However, epitopes which involve non-contiguous amino acids may require more, e.g., at least 15, 25, or 50 amino acids.

Antibodies which specifically bind to epitopes of huBUB3 proteins, polypeptides, fusion proteins, or biologically active variants can be used in immunochemical assays, including but not limited to Western blots, ELISAs, radioimmunoassays, immunohistochemical assays, immunoprecipitations, or other immunochemical assays known in the art. Typically, antibodies of the invention provide a detection signal at least 5-, 10-, or 20-fold higher than a detection signal provided with other proteins when used in such immunochemical assays. Preferably, antibodies which specifically bind to huBUB3 epitopes do not detect other proteins in immunochemical assays and can immunoprecipitate huBUB3 protein or polypeptides from solution.

Antibodies can be purified by methods well known in the art. Preferably, the antibodies are affinity purified, by passing the antibodies over a column to which a huBUB3 protein, polypeptide, variant, or fusion protein is bound. The bound antibodies can then be eluted from the column, for example, using a buffer with a high salt concentration.

The huBUB3 gene has the coding sequence shown in SEQ ID NO:1. Subgenomic polynucleotides of the invention contain less than a whole chromosome and can be single- or double-stranded. Preferably, the polynucleotides are intron-free. Isolated huBUB3 subgenomic polynucleotides can comprise at least 6, 8, 10, 12, 15, 20, 25, 30, 35, 40, 45, 50, 75, 100, 125, 150, 175, 200, 300, 400, 500, 600, 700, 800, 900, 1000, 1250, 1500, 1750, 2000, 2250, or 2500 or more contiguous nucleotides selected from the nucleotide sequence shown in SEQ ID NO:1 or its complement. In one embodiment, a huBUB3 subgenomic polynucleotide comprises nucleotides which encode the huBUB1-binding site.

The complement of the nucleotide sequence shown in SEQ ID NO:1 is a contiguous nucleotide sequence which forms Watson-Crick base pairs with the contiguous nucleotide sequence shown in SEQ ID NO:1. The complement of the nucleotide sequence shown in SEQ ID NO:1 (the antisense strand) is also a subgenomic polynucleotide and can be used provide huBUB3 antisense oligonucleotides. huBUB3 subgenomic polynucleotides also include polynucleotides which encode huBUB3-specific single-chain antibodies and ribozymes or which encode fusion proteins comprising huBUB3 amino acid sequences.

Degenerate nucleotide sequences encoding amino acid sequences of huBUB3 protein and or variants, as well as homologous nucleotide sequences which are at least 65%, 75%, 85%, 90%, 95%, 98%, or 99% identical to the nucleotide sequence shown in SEQ ID NO:1, are also huBUB3 subgenomic polynucleotides. Percent sequence identity between the sequence of a wild-type huBUB3 subgenomic polynucleotide and a homologous huBUB3 nucleotide sequence is determined using computer programs which employ the Smith-Waterman algorithm, for example as implemented in the MPSRCH program (Oxford Molecular), using an affine gap search with the following parameters: a gap open penalty of 12 and a gap extension penalty of 1.

Typically, homologous huBUB3 sequences can be confirmed by hybridization under stringent conditions, as is known in the art. For example, using the following wash conditions—2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of huBUB3 subgenomic polynucleotides of the invention can also be identified by making suitable probes or primers and screening cDNA expression libraries from other species, such as mice, monkeys, yeast, or bacteria, as well as human cDNA expression libraries. It is well known that the $T_m$ of a double-stranded DNA decreases by 1–1.5° C. with every 1% decrease in homology (Bonner et al., *J. Mol. Biol.* 81, 123 (1973). Homologous huBUB3 human polynucleotides or huBUB3 polynucleotides of other species can therefore be identified, for example, by hybridizing a putative homologous huBUB3 polynucleotide with a polynucleotide having the nucleotide sequence of SEQ ID NO:1 to form a test hybrids, comparing the melting temperature of the test hybrid with the melting temperature of a hybrid comprising a polynucleotide having SEQ ID NO:1 and a polynucleotide which is perfectly complementary to SEQ ID NO:1, and calculating the number or percent of basepair mismatches within the test hybrid.

Nucleotide sequences which hybridize to the coding sequence shown in SEQ ID NO:1 or its complement following stringent hybridization and/or wash conditions are also huBUB3 subgenomic polynucleotides of the invention. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between the huBUB3 sequence shown in SEQ ID NO:1 and a polynucleotide sequence which is 65%, 75%, 85%, 90%, 95%, 96%, 97%, 98%, or 99% identical to SEQ ID NO:1 can be calculated, for example, using the equation of Bolton and McCarthy, *Proc. Natl. Acad. Sci. U.S.A.* 48, 1390 (1962):

$$T_m = 81.5°\,C. - 16.6(\log_{10}[Na^+]) + 0.41(\%G+C) - 0.63(\%formamide) - 600/l),$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

huBUB3 subgenomic polynucleotides can be isolated and purified free from other nucleotide sequences using standard nucleic acid purification techniques. For example, restriction enzymes and probes can be used to isolate polynucleotide fragments which comprise nucleotide sequences encoding a huBUB3 protein. Isolated and purified subgenomic polynucleotides are in preparations which are free or at least 90% free of other molecules.

Complementary DNA (cDNA) molecules which encode huBUB3 proteins are also huBUB3 subgenomic polynucleotides of the invention. huBUB3 cDNA molecules can be made with standard molecular biology techniques, using huBUB3 mRNA as a template. huBUB3 cDNA molecules can thereafter be replicated using molecular biology techniques known in the art and disclosed in manuals such as Sambrook et al., 1989. An amplification technique, such as the polymerase chain reaction (PCR), can be used to obtain additional copies of subgenomic polynucleotides of the invention, using either human genomic DNA or cDNA as a template.

Alternatively, synthetic chemistry techniques can be used to synthesize huBUB3 subgenomic polynucleotide molecules of the invention. The degeneracy of the genetic code allows alternate nucleotide sequences to be synthesized which will encode a huBUB3 protein having the amino acid sequence shown in SEQ ID NO:2 or a biologically active variant of that sequence. All such nucleotide sequences are within the scope of the present invention.

The invention also provides polynucleotide probes which can be used to detect huBUB3 sequences, for example, in hybridization protocols such as Northern or Southern blotting or in situ hybridizations. Polynucleotide probes of the invention comprise at least 12, 13, 14, 15, 16, 17, 18, 19, 20, 30, or 40 or more contiguous nucleotides selected from SEQ ID NO:1. Polynucleotide probes of the invention can comprise a detectable label, such as a radioisotopic, fluorescent, enzymatic, or chemiluminescent label.

huBUB3 subgenomic polynucleotides can be used as primers to obtain additional copies of huBUB3 polynucleotides. huBUB3 subgenomic polynucleotides can also be used to express huBUB3 mRNA, protein, polypeptides, antibodies, or fusion proteins and to generate huBUB3 antisense oligonucleotides and ribozymes.

A huBUB3 subgenomic polynucleotide comprising huBUB3 coding sequences can be used in a construct, such as a DNA or RNA construct. huBUB3 constructs can be used, for example, to express all or a portion of a huBUB3 protein in a host cell. Preferably, the huBUB3 subgenomic polynucleotide is inserted into an expression plasmid (for example, the Ecdyson system, pIND, In Vitro Gene). huBUB3 subgenomic polynucleotides can be propagated in vectors and cell lines using techniques well known in the art. huBUB3 subgenomic polynucleotides can be on linear or circular molecules. They can be on autonomously replicating molecules or on molecules without replication sequences. They can be regulated by their own or by other regulatory sequences, as is known in the art.

A host cell comprising a huBUB3 expression construct can then be used to express all or a portion of a huBUB3 protein. Host cells comprising huBUB3 expression constructs can be prokaryotic or eukaryotic. A variety of host cells are available for use in bacterial, yeast, insect, and human expression systems and can be used to express or to propagate huBUB3 expression constructs (see below). Expression constructs can be introduced into host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and calcium phosphate-mediated transfection.

A huBUB3 expression construct comprises a promoter which is functional in a chosen host cell. The skilled artisan can readily select an appropriate promoter from the large number of cell type-specific promoters known and used in the art. The expression construct can also contain a transcription terminator which is functional in the host cell. The expression construct comprises a polynucleotide segment which encodes all or a portion of the huBUB3 protein, variant, fusion protein, antibody, or ribozyme. The polynucleotide segment is located downstream from the promoter. Transcription of the polynucleotide segment initiates at the promoter. The expression construct can be linear or circular and can contain sequences, if desired, for autonomous replication.

Bacterial systems for expressing huBUB3 expression constructs include those described in Chang et al., *Nature* (1978) 275: 615, Goeddel et al., *Nature* (1979) 281: 544, Goeddel et al., *Nucleic Acids Res.* (1980) 8: 4057, EP 36,776, U.S. Pat. No. 4,551,433, deBoer et al., *Proc. Natl. Acad. Sci. USA* (1983) 80: 21–25, and Siebenlist et al., *Cell* (1980)20: 269.

Expression systems in yeast include those described in Hinnen et al., *Proc. Natl. Acad. Sci. USA* (1978) 75: 1929; Ito et al., *J. Bacteriol.* (1983) 153: 163; Kurtz et al., *Mol. Cell. Biol.* (1986) 6: 142; Kunze et al., *J. Basic Microbiol.* (1985) 25: 141; Gleeson et al., *J. Gen. Microbiol.* (1986) 132: 3459, Roggenkamp et al., *Mol. Gen. Genet.* (1986) 202:302) Das et al., *J. Bacteriol.* (1984) 158: 1165; De Louvencourt et al., *J. Bacteriol.* (1983) 154: 737, Van den Berg et al., *Bio/Technology* (1990) 8: 135; Kunze et al., *J. Basic Microbiol.* (1985) 25: 141; Cregg et al., *Mol. Cell. Biol.* (1985) 5: 3376, U.S. Pat. Nos. 4,837,148, 4,929,555; Beach and Nurse, *Nature* (1981) 300: 706; Davidow et al., *Curr. Genet.* (1985) 10: 380, Gaillardin et al., *Curr. Genet.* (1985) 10: 49, Ballance et at, *Biochem. Biophys. Res. Commun.* (1983) 112: 284–289; Tilburn et al., *Gene* (1983) 26: 205–221, Yelton et al, *Proc. Natl. Acad. Sci. USA* (1984) 81: 1470–1474, Kelly and Hynes, *EMBO J.* (1985) 4: 475479; EP 244,234, and WO 91/00357.

Expression of huBUB3 expression constructs in insects can be carried out as described in U.S. Pat. No. 4,745,051, Friesen et al. (1986) "The Regulation of Baculovirus Gene Expression" in: THE MOLECULAR BIOLOGY OF BACULOVIRUSES (W. Doerfler, ed.), EP 127,839, EP 155,476, and Vlak et al., *J. Gen. Virol.* (1988) 69: 765–776, Miller et al., *Ann. Rev. Microbiol.* (1988) 42: 177, Carbonell et al., *Gene* (1988) 73: 409, Maeda et al., *Nature* (1985) 315: 592–594, Lebacq-Verheyden et al., *Mol. Cell. Biol.* (1988) 8: 3129; Smith et al., *Proc. Natl. Acad Sci. USA* (1985) 82: 8404, Miyajima et al., *Gene* (1987) 58: 273; and Martin et al., *DNA* (1988) 7:99. Numerous baculoviral strains and variants and corresponding permissive insect host cells from hosts are described in Luckow et al., *Bio/Technology* (1988) 6: 47–55, Miller et al., in GENETIC ENGINEERING (Setlow, J. K. et al. eds.), Vol. 8 (Plenum Publishing, 1986), pp.277–279, and Maeda et al., *Nature,* (1985) 315: 592–594.

Mammalian expression of huBUB3 expression constructs can be achieved as described in Dijkema et al., *EMBO J.* (1985) 4: 761, Gorman et al., *Proc. Natl. Acad. Sci. USA* (1982b) 79: 6777, Boshart et al., *Cell* (1985) 41: 521 and U.S. Pat. No. 4,399,216. Other features of mammalian expression of huBUB3 expression constructs can be facilitated as described in Ham and Wallace, *Meth. Enz.* (1979) 58: 44, Barnes and Sato, *Anal. Biochem.* (1980) 102: 255, U.S. Pat. Nos. 4,767,704, 4,657,866, 4,927,762, 4,560,655, WO 90/103430, WO 87/00195, and U.S. Pat. No. RE 30,985.

Subgenomic polynucleotides of the invention can also be used in gene delivery vehicles, for the purpose of delivering a huBUB3 mRNA or oligonucleotide (either with the sequence of native huBUB3 mRNA or its complement), full-length huBUB3 protein, huBUB3 fusion protein, huBUB3 polypeptide, or huBUB3-specific ribozyme or single-chain antibody into a cell, preferably a eukaryotic cell. According to the present invention, a gene delivery vehicle can be, for example, naked plasmid DNA, a viral expression vector comprising a huBUB3 subgenomic polynucleotide, or a huBUB3 subgenomic polynucleotide in conjunction with a liposome or a condensing agent.

In one embodiment of the invention, the gene delivery vehicle comprises a promoter and a huBUB3 subgenomic polynucleotide. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter.

A huBUB3 gene delivery vehicle can comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the huBUB3 gene delivery vehicle is a recombinant retroviral vector. Recombinant retroviruses and various uses thereof have been described in numerous references including, for example, Mann et al., *Cell* 33:153, 1983, Cane and Mulligan, *Proc. Nat'l. Acad. Sci. USA* 81:6349, 1984, Miller et al., *Human Gene Therapy* 1:5–14, 1990, U.S. Pat. Nos. 4,405,712, 4,861,719, and 4,980,289, and PCT Application Nos. WO 89/02,468, WO 89/05,349, and WO 90/02, 806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, *Cancer Res.* 53:3860–3864, 1993; Vile and Hart, *Cancer Res.* 53:962–967, 1993; Ram et al., *Cancer Res.* 53:83–88, 1993; Takamiya et al., *J. Neurosci. Res.* 33:493–503, 1992; Baba et al., *J. Neurosurg.* 79:729–735, 1993 (U.S. Pat. No. 4,777,127, GB 2,200,651, EP 0,345,242 and WO91/02805).

Particularly preferred retroviruses are derived from retroviruses which include avian leukosis virus (ATCC Nos. VR-535 and VR-247), bovine leukemia virus (VR-1315), murine leukemia virus (MLV), mink-cell focus-inducing virus (Koch et al., *J. Vir.* 49:828, 1984; and Oliff et al., *J. Vir.* 48:542, 1983), murine sarcoma virus (ATCC Nos. VR-844, 45010 and 45016), reticuloendotheliosis virus (ATCC Nos VR-994, VR-770 and 45011), Rous sarcoma virus, Mason-Pfizer monkey virus, baboon endogenous virus, endogenous feline retrovirus (e.g., RD114), and mouse or rat gL30 sequences used as a retroviral vector. Particularly preferred strains of MLV from which recombinant retroviruses can be generated include 4070A and 1504A (Hartley and Rowe, *J. Vir.* 19:19, 1976), Abelson (ATCC No. VR-999), Friend (ATCC No. VR-245), Grafi (Ru et al., *J. Vir.* 67:4722, 1993; and Yantchev *Neoplasma* 26:397, 1979), Gross (ATCC No. VR-590), Kirsten (Albino et al., *J. Exp. Med.* 164:1710, 1986), Harvey sarcoma virus (Manly et al., *J. Vir.* 62:3540, 1988; and Albino et al., *J. Exp. Med.* 164:1710, 1986) and Rauscher (ATCC No. VR-998), and Moloney MLV (ATCC No. VR-190). A particularly preferred non-mouse retrovirus is Rous sarcoma virus. Preferred Rous sarcoma viruses include Bratislava (Manly et al., *J. Vir.* 62:3540, 1988; and Albino et al., *J. Exp. Med.* 164:1710,1986), Bryan high titer (e.g., ATCC Nos. VR-334, VR-657, VR-726, VR-659, and VR-728), Bryan standard (ATCC No. VR-140), Carr-Zilber (Adgighitov et al., *Neoplasma* 27:159, 1980), Engelbreth-Holm (Laurent et al., *Biochem Biophys Acta* 908:241, 1987), Harris, Prague (e.g., ATCC Nos. VR-772, and 45033), and Schmidt-Ruppin (e.g. ATCC Nos. VR-724, VR-725, VR-354) viruses.

Any of the above retroviruses can be readily utilized in order to assemble or construct retroviral huBUB3 gene delivery vehicles given the disclosure provided herein and standard recombinant techniques (e.g., Sambrook et al., MOLECULAR CLONING: A LABORATORY MANUAL, 2d ed., Cold Spring Harbor Laboratory Press, 1989, and Kunkle, *Proc. Natl. Acad. Sci. U.S.A.* 82:488, 1985) known in the art. Portions of retroviral huBUB3 expression vectors can be derived from different retroviruses. For example, retrovector LTRs can be derived from a murine sarcoma virus, a tRNA binding site from a Rous sarcoma virus, a packaging signal from a murine leukemia virus, and an origin of second strand synthesis from an avian leukosis virus. These recombinant retroviral vectors can be used to generate transduction competent retroviral vector particles by introducing them into appropriate packaging cell lines (see U.S. Ser. No. 07/800,921, filed Nov. 29, 1991) now abandoned. Recombinant retroviruses can be produced which direct the site-specific integration of the recombinant retroviral genome into specific regions of the host cell DNA. Such site-specific integration can be mediated by a chimeric integrase incorporated into the retroviral particle (see U.S. Ser. No. 08/445, 466 filed May 22, 1995) now abandoned. It is preferable that the recombinant viral gene delivery vehicle is a replication-defective recombinant virus.

Packaging cell lines suitable for use with the above-described retroviral gene delivery vehicles can be readily prepared (see U.S. Ser. No. 08/240,030, filed May 9, 1994 now abandoned; see also WO 92/05266) and used to create producer cell lines (also termed vector cell lines or "VCLs") for production of recombinant viral particles. In particularly preferred embodiments of the present invention, packaging cell lines are made from human (e.g., HT1080 cells) or mink parent cell lines, thereby allowing production of recombinant retroviral gene delivery vehicles which are capable of surviving inactivation in human serum. The construction of recombinant retroviral gene delivery vehicles is described in detail in WO 91/02805. These recombinant retroviral gene delivery vehicles can be used to generate transduction competent retroviral particles by introducing them into appropriate packaging cell lines (see U.S. Ser. No. 07/800, 921). Similarly, adenovirus gene delivery vehicles can also be readily prepared and utilized given the disclosure provided herein (see also Berkner, *Biotechniques* 6:616–627, 1988, and Rosenfeld et al., *Science* 252:431–434, 1991, WO 93/07283, WO 93/06223, and WO 93/07282).

A huBUB3 gene delivery vehicle can also be a recombinant adenoviral gene delivery vehicle. Such vehicles can be readily prepared and utilized given the disclosure provided herein (see Berkner, *Biotechniques* 6:616, 1988, and Rosenfeld et al., *Science* 252:431, 1991, WO 93/07283, WO 93/06223, and WO 93/07282). Adeno-associated viral huBUB3 gene delivery vehicles can also be constructed and used to deliver huBUB3 amino acids or nucleotides. The use of adeno-associated viral gene delivery vehicles in vitro is described in Chatterjee et al., *Science* 258: 1485–1488 (1992), Walsh et al., *Proc. Nat'l. Acad. Sci.* 89: 7257–7261 (1992), Walsh et al., *J. Clin. Invest.* 94: 1440–1448 (1994), Flotte et al., *J. Biol. Chem.* 268: 3781–3790 (1993), Ponnazhagan et al., *J. Exp. Med.* 179: 733–738 (1994), Miller et al., *Proc. Nat'l Acad. Sci.* 91: 10183–10187 (1994), Einerhand et al., *Gene Ther.* 2: 336–343 (1995), Luo et al., *Exp. Hematol.* 23: 1261–1267 (1995), and Zhou et al., *Gene Therapy* 3: 223–229 (1996). In vivo use of these vehicles is described in Flotte et al., *Proc. Nat'l Acad. Sci.* 90: 10613–10617 (1993), and Kaplitt et al., *Nature Genet.* 8:148–153 (1994).

In another embodiment of the invention, a huBUB3 gene delivery vehicle is derived from a togavirus. Preferred togaviruses include alphaviruses, in particular those described in U.S. Ser. No. 08/405,627, filed Mar. 15, 1995, WO 95/07994. Alpha viruses, including Sindbis and ELVS viruses can be gene delivery vehicles for huBUB3 polynucleotides. Alpha viruses are described in WO 94/21792, WO 92/10578 and WO 95/07994. Several different alphavirus gene delivery vehicle systems can be constructed and used to deliver huBUB3 subgenomic polynucleotides to a cell according to the present invention. Representative examples of such systems include those described in U.S. Pat. Nos. 5,091,309 and 5,217,879. Particularly preferred alphavirus gene delivery vehicles for use in the present invention include those which are described in WO 95/07994, and U.S. Ser. No. 08/405,627.

Preferably, the recombinant viral vehicle is a recombinant alphavirus viral vehicle based on a Sindbis virus Sindbis constructs, as well as numerous similar constructs, can be readily prepared essentially as described in U.S. Ser. No. 08/198,450. Sindbis viral gene delivery vehicles typically comprise a 5' sequence capable of initiating Sindbis virus transcription, a nucleotide sequence encoding Sindbis nonstructural proteins, a viral junction region inactivated so as to prevent subgenomic fragment transcription, and a Sindbis RNA polymerase recognition sequence. Optionally, the viral junction region can be modified so that subgenomic polynucleotide transcription is reduced, increased, or maintained. As will be appreciated by those in the art, corresponding regions from other alphaviruses can be used in place of those described above.

The viral junction region of an alphavirus-derived gene delivery vehicle can comprise a first viral junction region which has been inactivated in order to prevent transcription of the subgenomic polynucleotide and a second viral junction region which has been modified such that subgenomic polynucleotide transcription is reduced. An alphavirus-derived vehicle can also include a 5' promoter capable of initiating synthesis of viral RNA from cDNA and a 3' sequence which controls transcription termination.

Other recombinant togaviral gene delivery vehicles which can be utilized in the present invention include those derived from Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309 and 5,217,879 and in WO 92/10578. The Sindbis vehicles described above, as well as numerous similar constructs, can be readily prepared essentially as described in U.S. Ser. No. 08/198,450 now abandoned.

Other viral gene delivery vehicles suitable for use in the present invention include, for example, those derived from poliovirus (Evans et al., *Nature* 339:385, 1989, and Sabin et al., *J. Biol. Standardization* 1:115, 1973) (ATCC VR-58); rhinovirus (Arnold et al., *J. Cell. Biochem.* L401, 1990) (ATCC VR-1110); pox viruses, such as canary pox virus or vaccinia virus (Fisher-Hoch et al., *Proc. Natl. Acad. Sci. U.S.A.* 86:317, 1989; Flexner et al., *Ann. N.Y. Acad. Sci.* 569:86, 1989; Flexner et al., *Vaccine* 8:17, 1990; U.S. Pat. No. 4,603,112 and U.S. 4,769,330; WO 89/01973) (ATCC VR-111; ATCC VR-2010); SV40 (Mulligan et al., *Nature* 277:108, 1979) (ATCC VR-305), (Madzak et al., *J. Gen. Vir.* 73:1533, 1992); influenza virus (Luytjes et al., *Cell* 59:1107, 1989; McMicheal et al., *The New England Journal of Medicine* 309:13, 1983; and Yap et al., *Nature* 273:238, 1978) (ATCC VR-797); parvovirus such as adeno-associated virus (Samulski et al., *J. Vir.* 63:3822, 1989, and Mendelson et a., *Virology* 166:154, 1988) (ATCC VR-645); herpes simplex virus (Kit et al., *Adv. Exp. Med. Biol.* 215:219, 1989) (ATCC VR-977; ATCC VR-260); *Nature* 277:108, 1979); human immunodeficiency virus (EPO 386, 882, Buchschacher et al., *J. Vir.* 66:2731, 1992); measles virus (EPO 440,219) (ATCC VR-24); a (ATCC VR-67; ATCC VR-1247), Aura (ATCC VR-368), Bebaru virus (ATCC VR-600; ATCC VR-1240), Cabassou (ATCC VR-922), Chikungunya virus (ATCC VR-64; ATCC VR-1241), Fort Morgan (ATCC VR-924), Getah virus (ATCC VR-369; ATCC VR-1243), Kyzylagach (ATCC VR-927), Mayaro (ATCC VR-66), Mucambo virus (ATCC VR-580; ATCC VR-1244), Ndumu (ATCC VR-371), Pixuna virus (ATCC VR-372; ATCC VR-1245), Tonate (ATCC VR-925), Triniti (ATCC VR-469), Una (ATCC VR-374), Whataroa (ATCC VR-926), Y-62–33 (ATCC VR-375), O'Nyong virus, Eastern encephalitis virus (ATCC VR-65; ATCC VR-1 242), Western encephalitis virus (ATCC VR-70; ATCC VR-1251; ATCC VR-622; ATCC VR-1252), and coronavirus (Hamre et al., *Proc. Soc. Exp. Biol. Med.* 121:190,1966) (ATCC VR-740).

A huBUB3 subgenomic polynucleotide of the invention can also be combined with a condensing agent to form a gene delivery vehicle. In a preferred embodiment, the condensing agent is a polycation, such as polylysine, polyarginine, polyornithine, protamine, spermine, spermidine, and putrescine. Many suitable methods for making such linkages are known in the art (see, for example, U.S. Ser. No. 08/366,787, filed Dec. 30, 1994) now abandoned.

In an alternative embodiment, a huBUB3 subgenomic polynucleotide is associated with a liposome to form a gene delivery vehicle. Liposomes are small, lipid vesicles comprised of an aqueous compartment enclosed by a lipid bilayer, typically spherical or slightly elongated structures several hundred Angstroms in diameter. Under appropriate conditions, a liposome can fuse with the plasma membrane of a cell or with the membrane of an endocytic vesicle within a cell which has internalized the liposome, thereby releasing its contents into the cytoplasm. Prior to interaction with the surface of a cell, however, the liposome membrane acts as a relatively impermeable barrier which sequesters and protects its contents, for example, from degradative enzymes. Additionally, because a liposome is a synthetic structure, specially designed liposomes can be produced which incorporate desirable features. See Stryer, *Biochemistry*, pp. 236–240, 1975 (W. H. Freeman, San Francisco, Calif.); Szoka et al., *Biochim. Biophys. Acta* 600:1, 1980; Bayer et al., *Biochim. Biophys. Acta.* 550:464, 1979; Rivnay et al., *Meth. Enzymol.* 149:119, 1987; Wang et al., *Proc. Natl. Acad. Sci. U.S.A.* 84: 7851, 1987, Plant et al., *Anal. Biochem.* 176:420, 1989, and U.S. Pat. No. 4,762,915. Liposomes can encapsulate a variety of nucleic acid molecules including DNA, RNA, plasmids, and expression constructs comprising huBUB3 subgenomic polynucleotides such those disclosed in the present invention.

Liposomal preparations for use in the present invention include cationic (positively charged), anionic (negatively charged) and neutral preparations. Cationic liposomes have been shown to mediate intracellular delivery of plasmid DNA (Felgner et al., *Proc. Natl. Acad. Sci. USA* 84:7413–7416, 1987), mRNA (Malone et al., *Proc. Natl. Acad. Sci. USA* 86:6077–6081, 1989), and purified transcription factors (Debs et al., *J. Biol. Chem.* 265:10189–10192, 1990), in functional form. Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. See also Felgner et al., *Proc. Natl. Acad. Sci. USA* 91: 5148–5152.87, 1994. Other commercially available liposomes include Transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* 75:4194–4198, 1978; and WO 90/11092 for descriptions of the synthesis of DOTAP (1,2-bis(oleoyloxy)-3-(trimethylammonio)propane) liposomes.

Similarly, anionic and neutral liposomes are readily available, for example, from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphosphatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., METHODS OF IMMUNOLOGY (1983), Vol. 101, pp. 512–527; Szoka et al., *Proc. Natl. Acad. Sci. USA* 87:3410–3414, 1990; Papahadjopoulos et al., *Biochim. Biophys. Acta* 394:483, 1975; Wilson et al., *Cell* 17:77, 1979; Deamer and Bangham, *Biochim. Biophys. Acta* 443:629, 1976; Ostro et al., *Biochem. Biophys. Res. Commun.* 76:836, 1977; Fraley et al., *Proc. Natl. Acad. Sci. USA* 76:3348, 1979; Enoch and Strittmatter, *Proc. Natl. Acad. Sci. USA* 76:145, 1979; Fraley et al., *J. Biol Chem.* 255:10431, 1980; Szoka and Papahadjopoulos, *Proc. Natl. Acad. Sci. USA* 75:145, 1979; and Schaefer-Ridder et al., *Science* 215:166, 1982.

In addition, lipoproteins can be included with a huBUB3 subgenomic polynucleotide for delivery to a cell. Examples of such lipoproteins include chylomicrons, HDL, IDL, LDL, and VLDL. Mutants, fragments, or fusions of these proteins can also be used. Modifications of naturally occurring lipoproteins can also be used, such as acetylated LDL. These lipoproteins can target the delivery of polynucleotides to cells expressing lipoprotein receptors. Preferably, if lipoproteins are included with a polynucleotide, no other targeting ligand is included in the composition.

In another embodiment, naked huBUB3 subgenomic polynucleotide molecules are used as gene delivery vehicles, as described in WO 90/11092 and U.S. Pat. No. 5,580,859. Such gene delivery vehicles can be either huBUB3 DNA or RNA and, in certain embodiments, are linked to killed adenovirus. Curiel et al., *Hum. Gene. Ther.* 3:147–154, 1992. Other suitable vehicles include DNA-ligand (Wu et al., *J. Biol. Chem.* 264:16985–16987, 1989), lipid-DNA combinations (Felgner et al., *Proc. Natl. Acad. Sci. USA* 84:7413 7417,1989), liposomes (Wang et al., *Proc. Natl. Acad. Sci.* 84:7851–7855, 1987) and microprojectiles (Williams et al., *Proc. Natl. Acad. Sci.* 88:2726–2730, 1991).

One can increase the efficiency of naked huBUB3 subgenomic polynucleotide uptake into cells by coating the polynucleotides onto biodegradable latex beads. This approach takes advantage of the observation that latex beads, when incubated with cells in culture, are efficiently transported and concentrated in the perinuclear region of the cells. The beads will then be transported into cells when injected into muscle. huBUB3 subgenomic polynucleotide-coated latex beads will be efficiently transported into cells after endocytosis is initiated by the latex beads and thus increase gene transfer and expression efficiency. This method can be improved further by treating the beads to increase their hydrophobicity, thereby facilitating the disruption of the endosome and release of huBUB3 subgenomic polynucleotides into the cytoplasm.

huBUB3 or huBUB1 activity can be decreased in a cell by contacting the cell with a reagent which binds to an expression product of huBUB3 or huBUB1, respectively. In one embodiment of the invention, the reagent is a ribozyme, an RNA molecule with catalytic activity. See, e.g., Cech, *Science* 236: 1532–1539; 1987; Cech, *Ann. Rev. Biochem.* 59:543–568; 1990, Cech, *Curr. Opin. Struct. Biol.* 2: 605–609; 1992, Couture and Stinchcomb, *Trends Genet.* 12: 510–515, 1996. Ribozymes can be used to inhibit gene function by cleaving an RNA sequence, as is known in the art (e.g., Haseloff et al., U.S. Pat. No. 5,641,673).

The coding sequence of a huBUB1 or huBUB3 genes can be used to generate ribozymes which will specifically bind to mRNA transcribed from the huBUB1 or huBUB3 genes. Methods of designing and constructing ribozymes which can cleave other RNA molecules in trans in a highly sequence specific manner have been developed and described in the art (see Haseloff, J. et al. *Nature* 334:585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201). The nucleotide sequences shown in SEQ ID NOS:1 and 3 provide a source of suitable hybridization region sequences. Longer complementary sequences can be used to increase the affinity of the hybridization sequence for the target. The hybridizing and cleavage regions of the ribozyme can be integrally related; thus, upon hybridizing to the target RNA through the complementary regions, the catalytic region of the ribozyme can cleave the target.

Ribozymes can be introduced into cells as part of a DNA construct, as is known in the art and described above. Mechanical methods, such as microinjection, liposome-mediated transfection, electroporation, or calcium phosphate precipitation, can be used to introduce the ribozyme-containing DNA construct into cells in which it is desired to decrease huBUB1 or huBUB3 expression, as described above. Alternatively, if it is desired that the cells stably retain the DNA construct, it can be supplied on a plasmid and maintained as a separate element or integrated into the genome of the cells, as is known in the art. The DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors which induce expression of a target gene. Ribozymes can also be engineered to provide an additional level of regulation, so that destruction of mRNA occurs only when both a ribozyme and a target gene are induced in the cells.

In another embodiment of the invention, the level of huBUB1 or huBUB3 gene expression is decreased using an antisense oligonucleotide sequence. The antisense sequence is complementary to at least a portion of the sequence encoding huBUB1 or huBUB3 selected from the nucleotide sequences shown in SEQ ID NOS:1 or 3. Preferably, the antisense oligonucleotide sequence is at least 11 nucleotides in length, but can be at least 12, 15, 20, 25, 30, 35, 40, 45, or 50 or more nucleotides long. Longer sequences can also be used. Antisense oligonucleotide molecules can be provided in a DNA construct and introduced into cells as described above to decrease the level of huBUB1 or huBUB3 in the cells.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such as alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20:1–8, 1994; Sonveaux, *Meth. Mol. Biol.* 26:1–72, 1994; Uhlmann et al., *Chem. Rev.* 90:543–583, 1990.

Precise complementarity is not required for successful duplex formation between an antisense molecule and the complementary coding sequence of a huBUB1 or huBUB3 gene. Antisense molecules which comprise, for example, 2, 3, 4, or 5 or more stretches of contiguous nucleotides which are precisely complementary to a huBUB1 or huBUB3 coding sequence, each separated by a stretch of contiguous nucleotides which are not complementary to adjacent huBUB1 or huBUB3 coding sequences, can provide targeting specificity for huBUB1 or huBUB3 mRNA. Preferably, each stretch of contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular huBUB1 or huBUB3 coding sequence.

Antisense oligonucleotides can be modified without affecting their ability to hybridize to a huBUB1 or huBUB3 coding sequence. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, can also be employed in a modified antisense oligonucleotide. These modified oligonucleotides can be prepared by methods well known in the art. See, e.g., Agrawal et al., *Trends Biotechnol.* 10:152–158, 1992; Uhlmann et al., *Chem. Rev.* 90:543–584, 1990; Uhlmann et al., *Tetrahedron. Lett.* 215:3539–3542, 1987.

Antibodies of the invention which specifically bind to huBUB3, particularly single-chain antibodies, can also be used to alter levels of huBUB3. Antibodies similarly prepared against huBUB3 can be used to alter levels of huBUB3. The antibodies prevent huBUB3 and huBUB1 from binding. Polynucleotides encoding single-chain antibodies of the invention can be introduced into cells as described above.

Preferably, the mechanism used to decrease the level of huBUB1 or huBUB3 expression, whether ribozyme, antisense oligonucleotide sequence, or antibody, decreases the level of gene expression by at least 50%, 60%, 70%, or 80%. Most preferably, the level of gene expression is decreased by at least 90%, 95%, 99%, or 100%. The effectiveness of the mechanism chosen to decrease the level of gene expression can be assessed using methods well known in the art, such as hybridization of nucleotide probes to huBUB1 or huBUB3 mRNA, quantitative RT-PCR, or detection of huBUB1 or huBUB3 protein using specific antibodies of the invention.

Compositions comprising huBUB1 or huBUB3 antibodies, ribozymes, or antisense oligonucleotides can optionally comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in huBUB1 or huBUB3 compositions, for example, mineral salts such as hydrochlorides, hydrobromides, phosphates, or sulfates, as well as salts of organic acids such as acetates, proprionates, malonates, or benzoates. huBUB1 or huBUB3 compositions can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for a huBUB3 composition.

Typically, a huBUB1 or huBUB3 composition is prepared as an injectable, either as a liquid solution or suspension; however, solid forms suitable for solution or suspension in liquid vehicles prior to injection can also be prepared. A huBUB1 or huBUB3 composition can also be formulated into an enteric coated tablet or gel capsule according to known methods in the art, such as those described in U.S. Pat. No. 4,853,230, EP 225,189, AU 9,224,296, and AU 9,230,801.

According to one diagnostic method of the invention, loss of a wild-type huBUB3 gene is detected. The loss can be due to deletional, missense, frameshift, and/or point mutational events. If only a single huBUB3 allele is mutated, an early neoplastic state is indicated. However, if both alleles are mutated then a late neoplastic state is indicated. Point mutational events can occur in regulatory regions, such as in the promoter of the huBUB3 gene, leading to loss or diminution of expression of the huBUB3 mRNA. This can be determined using assays for quantitating huBUB3 expression.

In order to detect the loss of a wild-type huBUB3 gene in a tissue, it is helpful to isolate the tissue free from surrounding normal tissues. Means for enriching a tissue preparation for tumor (or cancer) cells are known in the art. For example, the tissue can be isolated from paraffin or cryostat sections. Cancer cells can also be separated from normal cells by flow cytometry. These as well as other techniques for separating tumor from normal cells are well known in the art. If the tumor tissue is highly contaminated with normal cells, detection of mutations is more difficult.

Detection of point mutations can be accomplished by molecular cloning of the huBUB3 allele (or alleles) present in the tumor tissue and sequencing the allele(s) using techniques well known in the art. Alternatively, an amplification technique, such as the polymerase chain reaction, can be used to amplify huBUB3 gene sequences directly from a genomic DNA preparation from tumor tissue. The DNA sequence of the amplified sequences can then be determined. The polymerase chain reaction itself is well known in the art. See, e.g., Saiki et al., *Science* 239, 487, 1988; U.S. Pat. Nos. 4,683,203; and 4,683,195. Specific primers which can be used in order to amplify the huBUB3 gene will be discussed in more detail below.

Specific deletions of huBUB3 genes can also be detected. For example, restriction fragment length polymorphism (RFLP) probes for the huBUB3 gene or surrounding marker genes can be used to score loss of a huBUB3 allele. Any other techniques for detecting deletions known in the art can be used.

Loss of wild-type huBUB3 genes can also be detected on the basis of the loss of a wild-type expression product of the huBUB3 gene. Such expression products include both the mRNA as well as the huBUB3 protein product itself. Point mutations can be detected by sequencing the mRNA directly or via molecular cloning of cDNA made from the mRNA. The sequence of the cloned cDNA can be determined using DNA sequencing techniques which are well known in the art. See Sambrook et al., 1989.

Alternatively, mismatch detection can be used to detect point mutations in the huBUB3 gene or its mRNA product. While these techniques are less sensitive than sequencing, they are simpler to perform on a large number of tumors. An example of a mismatch cleavage technique is the RNase protection method, which is described in detail in Winter et al., *Proc. Natl. Acad. Sci. U.S.A.* 82, 7575 (1985) and Meyers et al., *Science* 230, 1242 (1985). In the practice of the present invention, the method involves the use of a labeled riboprobe which is complementary to the human wild-type huBUB3 gene. The riboprobe and either mRNA or DNA isolated from the tumor tissue are hybridized together and subsequently digested with the enzyme RNase a, which is able to detect some mismatches in a duplex RNA structure. If a mismatch is detected by RNase a, it cleaves at the site of the mismatch. When the hybridized RNA preparation is separated on an electrophoretic gel matrix, a mismatch which has been detected and cleaved by RNase a will be evidenced by an RNA product which is smaller than the full-length duplex RNA for the riboprobe and the huBUB3 mRNA or DNA. The riboprobe need not be the fill length of the huBUB3 mRNA or gene but can be a segment of either. If the riboprobe comprises only a segment of the huBUB3 mRNA or gene it will be desirable to use a number of these probes to screen the whole mRNA sequence for mismatches.

In similar fashion, DNA probes can be used to detect mismatches through enzymatic or chemical cleavage. See, e.g., Cotton et al., *Proc. Natl. Acad. Sci. U.S.A.* 85, 4397 (1988) and Shenk et al., *Proc. Natl. Acad. Sci. U.S.A.* 72, 989 (1975). Alternatively, mismatches can be detected by shifts in the electrophoretic mobility of mismatched duplexes relative to matched duplexes. See, e.g. Cariello, *Human Genetics* 42, 726 (1988). With either riboprobes or DNA probes, the cellular mRNA or DNA which might contain a mutation can be amplified before hybridization using PCR or other amplification techniques, as is known in the art.

DNA sequences of the huBUB3 gene from the tumor tissue which have been amplified can also be screened using allele-specific probes. These probes are nucleic acid oligomers, each of which contains a region of the huBUB3 gene sequence harboring a known mutation. For example, one oligomer can be at least about 15, 18, 20, 30, or 50 nucleotides in length, corresponding to a portion of the huBUB3 gene sequence. By use of a battery of such allele-specific probes, amplification products can be screened to identify the presence of a previously identified mutation in the huBUB3 gene. Hybridization of allele-specific probes with amplified huBUB3 sequences can be performed, for example, on a solid support, such as a nitrocellulose or nylon filter. Hybridization to a particular probe indicates the presence of the same mutation in the tumor tissue as in the allele-specific probe.

Loss of wild-type huBUB3 genes can also be detected by screening for loss of wild-type huBUB3 protein function. Although all of the functions which the huBUB3 protein undoubtedly possesses have yet to be elucidated, at least one specific function is known. The huBUB3 protein binds to huBUB1. Loss of the ability of the huBUB3 protein to bind to huBUB1 indicates a mutational alteration in the protein which reflects a mutational alteration of the huBUB3 gene itself. Similarly, loss of kinase activity of huBUB3 can be monitored as a means of detecting mutations. Alternatively, a panel of monoclonal or single-chain antibodies can be used in which epitopes involved in huBUB3 functions are represented by a monoclonal or single-chain antibody. Loss or perturbation of binding of huBUB3 to a monoclonal antibody in the panel would indicate mutational alteration of the huBUB3 protein and thus of the huBUB3 gene itself. Any means for detecting an altered huBUB3 protein can be used to detect loss of wild-type huBUB3 genes.

Mutant huBUB3 genes or gene products can also be detected in body samples, such as serum or stool, or other body fluids, such as urine and sputum. The same techniques discussed above for detection of mutant huBUB3 genes or gene products in tissues can be applied to other body samples. By screening such body samples, a simple early diagnosis can be achieved for many types of cancers. In addition, the progress of chemotherapy can be monitored more easily by testing such body samples for mutant huBUB3 genes or gene products.

It appears that the huBUB3 gene has a role in the development of a broad range of tumors. The diagnostic methods of the invention are therefore applicable to any tumor in which huBUB3 has a role in tumorigenesis. These include lung, breast, brain, colorectal, bladder, mesenchyme, prostate, liver, stomach, leukemias, osteosarcomas. The diagnostic method of the invention is useful for clinicians so that they can decide upon an appropriate course of treatment. For example, a tumor displaying loss of wild-type huBUB3 alleles suggests the use of mitotic poison-type chemotherapy. Wild-type huBUB3 in a tumor suggests that other types of anti-cancer therapies should be used.

The invention also provides diagnostic kits. A kit of the present invention is useful for determination of the nucleotide sequence of a huBUB3 gene using the a polymerase chain reaction or other amplification technique. A kit comprises one or a set of pairs of single-stranded DNA primers which can be annealed to sequences within or surrounding the huBUB3 gene in order to prime amplifying DNA synthesis of the huBUB3 gene itself. The complete set allows synthesis of all of the nucleotides of the huBUB3 gene coding sequences, although isolated primers for selected portions can also be used. The set of primers may or may not allow synthesis of both intron and exon sequences. However, it should allow synthesis of all exon sequences. Instructions for using the primer(s) in the appropriate amplification method, as well as reagents required for the method, such as buffers and polymerase, can also be provided.

In order to facilitate subsequent cloning of amplified sequences, primers may have restriction enzyme sites appended to their 5' ends. Thus, all nucleotides of the primers are derived from huBUB3 sequences or sequences adjacent to huBUB3 except the few nucleotides necessary to form a restriction enzyme site. Such enzymes and sites are well known in the art. The primers themselves can be synthesized using techniques which are well known in the art. Generally, the primers can be made using synthesizing machines which are commercially available. In a preferred embodiment, the primer pairs comprise: sense primer TWS95 (GGGAGCCCAAGATGACCGGTT) (SEQ ID NO:5) and antisense primer TWS96 (AAATCCACCATTGGGGAGTACGAATTGT) (SEQ ID NO:6).

Nucleotide probes according to the present invention comprise at least about 10, 12, 14, 16, 18, 20, 25, or 30 contiguous nucleotides of huBUB3. The probes can also contain labeling moieties with which the probes can be detected, including but not limited to radiolabels, fluorescent labels, and enzymatic labels. Nucleotide probes provided by the present invention are useful in the RNase protection method, for detecting point mutations already discussed above. Probes can also be used to detect mismatches with a huBUB3 gene or mRNA using other techniques. Mismatches can be detected using other enzymes (e.g., S1 nuclease), chemicals (e.g., hydroxylamine or osmium tetroxide and piperidine), or changes in electrophoretic mobility of mismatched hybrids as compared to totally matched hybrids. These techniques are known in the art. See Cotton; Shenk; Myers; Winter; and Novack et al., *Proc. Natl. Acad. Sci. U.S.A.* 83, 586 (1986).

If a riboprobe is used to detect mismatches with mRNA, it is complementary to the mRNA of the human wild-type huBUB3 gene. The riboprobe thus is an anti-sense probe in that it does not code for the huBUB3 protein because it is of the opposite polarity to the sense strand. The riboprobe generally will be radioactively labeled; such labeling can be accomplished by any means known in the art. If the riboprobe is used to detect mismatches with DNA it can be of either polarity, sense or anti-sense. Similarly, DNA probes also may be used to detect mismatches. Probes may also be complementary to mutant alleles of huBUB3. These probes are useful to detect similar mutations in other patients on the basis of hybridization rather than mismatches. These probes are discussed above and referred to as allele-specific probes.

Genetic predisposition to cancers or neoplasia can be ascertained by testing normal tissues of humans, including prenatal humans. For example, a person who has inherited a germline huBUB3 mutation would be prone to develop cancers. This predisposition can be determined by testing DNA from any tissue of the person's body. Most simply, blood can be drawn and DNA extracted from cells of the blood. Loss of a wild-type huBUB3 allele, either by point mutation, deletion, or insertion can be detected by any of the means discussed above. DNA can also be extracted and tested from fetal tissues for this purpose.

According to the present invention a method is also provided of supplying wild-type huBUB3 function to a cell which carries mutant huBUB3 alleles. The wild-type huBUB3 gene or a part of the gene can be introduced into the cell in a vector such that the gene remains extrachromosomal. In such a situation the gene will be expressed by the cell from the extrachromosomal location. If a gene portion is introduced and expressed in a cell carrying a mutant huBUB3 allele, the gene portion should encode a part of the huBUB3 protein which is required for non-neoplastic growth of the cell. The portion of huBUB3 protein which is required for non-neoplastic growth can be readily determined, for example, by transfecting DNA expression constructs comprising portions of huBUB3 protein, such as the huBUB1 binding domain, into neoplastic cell lines in vitro and observing alterations in cellular morphology or lowered rates of cell division, as is known in the art.

More preferred is the situation where the wild-type huBUB3 gene or a part of it is introduced into the mutant cell in such a way that it recombines with the endogenous mutant huBUB3 gene present in the cell. Such recombination would require a double recombination event which would result in the correction of the huBUB3 gene mutation. Vectors and gene delivery vehicles for introduction of genes both for recombination and for extrachromosomal maintenance are known in the art and any suitable method, such as those described in detail above, can be used.

A composition comprising all or a portion of a huBUB3 subgenomic polynucleotide or polypeptide or other molecule which has huBUB3 activity can be supplied to cells which carry mutant huBUB3 alleles. The active molecules can be introduced into the cells by local or systemic administration, including injection, oral administration, particle gun, or catheterized administration, and topical administration. Alternatively, some such active molecules can be taken up by the cells, actively or by diffusion.

Various methods can be used to administer a huBUB3 therapeutic composition directly to a specific site in the body. For treatment of a tumor, for example, an appropriate huBUB3 composition injected several times in several different locations within the body of the tumor. Alternatively, arteries which serve the tumor can be identified, and a huBUB3 composition can be injected into such an artery in order to deliver the composition to the tumor.

A tumor which has a necrotic center can be aspirated, and a huBUB3 composition can be injected directly into the now empty center of the tumor. A huBUB3 composition can also be administered directly to the surface of a tumor, for example, by topical application of the composition. X-ray imaging can be used to assist in certain of these delivery methods. Combination therapeutic agents, including a huBUB3 protein or polypeptide or a huBUB3 subgenomic polynucleotide, can be administered simultaneously or sequentially together with other therapeutic agents.

huBUB3 compositions can also be delivered to specific tissues using receptor-mediated targeted delivery. Receptor-mediated DNA delivery techniques are taught in, for example, Findeis et al. *Trends in Biotechnol.* 11, 202–05, (1993); Chiou et al., GENE THERAPEUTICS: METHODS AND APPLICATIONS OF DIRECT GENE TRANSFER (J. A. Wolff, ed.) (1994); Wu & Wu, *J. Biol. Chem.* 263, 621–24, 1988; Wu et al., *J. Biol. Chem.* 269, 542–46, 1994; Zenke et al., *Proc. Natl. Acad. Sci. U.S.A.* 87, 3655–59, 1990; Wu et al., *J. Biol. Chem.* 266, 338–42, 1991.

Both the dose of a particular huBUB3 composition and the means of administering the composition can be determined based on specific qualities of the huBUB3 composition, the condition, age, and weight of the patient, the progression of the particular disease being treated, and other relevant factors. If the composition contains huBUB3 proteins, polypeptides, or antibodies, effective dosages of the composition are in the range of about 5 µg to about 50 µg/kg of patient body weight, about 50 µg to about 5 mg/kg, about 100 µg to about 500 µg/kg of patient body weight, and about 200 to about 250 µg/kg.

Compositions containing huBUB3 subgenomic polynucleotides, including antisense oligonucleotides and ribozyme-or antibody-encoding sequences, can be administered in a range of about 100 ng to about 200 mg of DNA for local administration. Suitable concentrations range from about 500 ng to about 50 mg, about 1 µg to about 2 mg, about 5 µg to about 500 µg, and about 20 µg to about 100 µg of DNA. Factors such as method of action and efficacy of transformation and expression are considerations which will affect the dosage required for ultimate efficacy of the huBUB3 composition. If greater expression is desired over a larger area of tissue, larger amounts of a huBUB3 composition or the same amount administered successively, or several administrations to different adjacent or close tissue portions of, for example, a tumor site, may be required to effect a positive therapeutic outcome. In all cases, routine experimentation in clinical trials will determine specific ranges for optimal therapeutic effect.

Expression of an endogenous huBUB3 gene in a cell can be altered by introducing in frame with the endogenous huBUB3 gene a DNA construct comprising a huBUB3 targeting sequence, a regulatory sequence, an exon, and an unpaired splice donor site by homologous recombination, such that a homologously recombinant cell comprising a new huBUB3 transcription unit is formed. The new transcription unit can be used to turn the huBUB3 gene on or off as desired. This method of affecting endogenous gene expression is taught in U.S. Pat. No. 5,641,670.

The targeting sequence is a segment of at least 10, 12, 15, 20, or 50 contiguous nucleotides selected from the nucleotide sequence shown in SEQ ID NO:1. The transcription unit is located upstream of a coding sequence of the endogenous huBUB3 gene. The exogenous regulatory sequence directs transcription of the coding sequence of the huBUB3 gene.

According to another aspect of the invention, test compounds can be screened for utility as anti-cancer agents by the ability to suppress the expression or function of human huBUB3 protein. Potential drugs can be contacted with cells and the expression of huBUB3 mRNA or protein monitored. This can be accomplished by well known techniques in the art, such as Northern blots, immunoprecipitation, immunoblots, etc. Any technique which utilizes a huBUB3 nucleic acid probe or an antibody specific for huBUB3 protein can be used. Other techniques, such as quantitative reverse PCR can also be employed.

In addition, in vitro techniques can be employed for testing the ability of candidate drugs to inhibit huBUB3 binding to huBUB1. Such assays are well within the skill of the art, once provided with the full sequences of the huBUB3 and huBUB1 genes and proteins. In addition, a yeast two-hybrid system can be used wherein one of the partners is huBUB3 and one of the partners is huBUB1. A cell which contains both of these partners can be contacted with test compounds and the loss or diminution of transactivation of the reporter gene can be monitored.

Inhibitors of huBUB1–huBUB3 binding can be, for example, polypeptides, small peptides, peptoids, or other peptide analogs or other chemical inhibitors. Some of these inhibitors, such as related peptides or fusion proteins, can be developed rationally on the basis of knowledge of the sequences of huBUB1 and huBUB3 which are disclosed herein. Alternatively, a random array of compounds can be screened for the ability to compete in a huBUB1–huBUB3 binding assay.

The test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art.

A test compound can be contacted with a mixture of at least a huBUB1-binding domain of a huBUB3 protein and at least a huBUB3-binding domain of a huBUB1 protein. These molecules can be produced recombinantly or can be synthesized using standard chemical methods. The binding domains or proteins can be pre-bound prior to the step of contacting the test compound. Alternatively, the test compound can contact one of the binding domains or proteins before the second binding domain or protein is added.

The binding domains or proteins can be in solution or one binding domain or protein can be bound to a solid support. The binding domains or proteins can be unlabeled or labeled, for example, with a radioactive, fluorescent, or other detectable marker. They can be fusion proteins comprising huBUB1 or huBUB3 fused to another protein with or without a detectable enzymatic activity.

In one embodiment, the amount of at least one of the two binding domains or proteins that is bound or unbound in the presence of the test compound is then measured. A number of methods can be used to measure the amount of binding domains or proteins or dimers. For example, the relative concentration of binding domains or proteins bound to unbound can be detected by examining the apparent molecular masses of the molecules by size exclusion chromatography or by polyacrylamide gel electrophoresis under non-reducing conditions. Other methods of measuring binding or dissociation of the binding domains or proteins will readily occur to those of ordinary skill in the art and can be used. A test compound which diminishes the quantity of one binding domain or protein bound to a second binding domain or protein, or which displaces one binding domain or protein bound to a second binding domain or protein, or which prevents one binding domain or protein from binding to a second binding domain or protein is identified as a candidate therapeutic agent.

According to the present invention a method is also provided of using the yeast two-hybrid technique to screen for test compounds which interfere with huBUB1–huBUB3 binding. The yeast two-hybrid technique is taught in Fields & Song, *Nature* 340, 245–46, 1989.

In a preferred embodiment, a cell is contacted with a test compound. The cell comprises two fusion proteins, which can be supplied to the cell by means of recombinant DNA constructs. The first fusion protein comprises a DNA-binding domain. The second fusion protein comprises a transcriptional activating domain. The first fusion protein also comprises either (I) a binding domain of huBUB1 that binds to huBUB3 or (ii) a binding domain of huBUB3 that binds to huBUB1. If the first fusion protein comprises a binding domain of huBUB1 that binds to huBUB3, then the second fusion protein comprises a binding domain of huBUB3 that binds to huBUB1. If the first fusion protein comprises a binding domain of huBUB3 that binds to huBUB1, then the second fusion protein comprises a binding domain of huBUB1 that binds to huBUB3. The cell also comprises a reporter gene comprising a DNA sequence downstream from a DNA element to which the DNA binding domain of the first fusion protein binds.

When the huBUB3 and huBUB1 binding domains are bound together, the DNA binding domain and the transcriptional activating domain will be in close enough proximity to reconstitute a transcriptional activator capable of initiating transcription of a detectable reporter gene in the cell. The expression of the reporter gene in the presence of the test compound is then measured. A test compound that increases the expression of the reporter gene is a potential drug for increasing huBUB1–huBUB3 binding. A test compound that decreases the expression of the reporter gene is a potential drug for decreasing huBUB1–huBUB3 binding.

Many DNA binding domains and transcriptional activating domains can be used in this system, including the DNA binding domains of GAL4, LexA, and the human estrogen receptor paired with the acidic transcriptional activating domains of GAL4 or the herpes virus simplex protein VP16 (see, e.g., Hannon et al., *Genes Dev.* 7,2378,1993; A. S. Zervos et al., *Cell* 72,223,1993; A. B. Votjet et al., *Cell* 74, 205, 1993; Harper et al., *Cell* 75, 805, 1993; B. Le Douarin et al., *Nucl. Acids Res.* 23, 876, 1995). A number of plasmids known in the art can be constructed to contain the coding sequences for the fusion proteins using standard laboratory techniques for manipulating DNA (see, e.g., Example 1, below).

Suitable detectable reporter genes include the *E. coli* lacZ gene, whose expression can be measured colorimetrically (see, e.g., Fields and Song), and yeast selectable genes such as HIS3 (Harper et al.; Votjet et al.; Hannon et al.) or URA3 (Le Douarin et al.). Methods for transforming cells are also well known in the art. See, e.g., a. Hinnen et al., *Proc. Natl. Acad. Sci. U.S.A.* 75, 1929–1933, 1978. The test compound can comprise part of the cell culture medium or it may be added separately.

For example, compounds which decrease the kinase activity of huBUB1 or of a huBUB1–huBUB3 complex can be identified by contacting huBUB1 or a huBUB1–huBUB3 complex with a test compound and determining the kinase activity of the huBUB1 or huBUB1–huBUB3 complex. Any in vitro kinase assay known in the art, such as taught in W096/36642, can be used for this purpose. Phosphorylation of a substrate, such as huBUB1 itself or a synthetic peptide substrate based on huBUB1 sequences shown in SEQ ID NO:2, or a kinase substrate such as PHAS-1, can be measured. Optionally, the substrate can comprise a detectable label, such as biotin, for use in a purification or separation step. A test compound which decreases kinase activity of huBUB1 or of the huBUB1–huBUB3 complex is identified as a candidate therapeutic agent.

The huBUB3-binding domain of huBUB1 and the huBUB1-binding domain of huBUB3 can be readily determined, for example, by testing various portions of each protein for the ability to bind to its partner. A variety of techniques can be used for this purpose, including but not limited to the yeast two-hybrid assay, affinity column chromatography, and polyacrylamide gel electrophoresis under non-reducing conditions.

The invention also provides methods of increasing the sensitivity of a tumor to a metabolic inhibitor. Normal cell division includes a highly controlled segregation of subcellular components, especially chromosomes and spindle pole bodies, a process which requires the function of microtubules. In normal cells, the presence of microtubule poisons arrests cell division prior to segregation of these components. In this manner, cells refrain from attempting to segregate these components under conditions which might affect the normal fidelity of this segregation.

In mutant cells lacking huBUB3 (and/or other genes known to function in this pathway such as huBUB1), a signal transduction pathway which senses proper microtubule function is absent. Thus, mutant cells treated with these drugs fail to regulate cell cycle progression. In this case, cell division occurs without proper segregation of subcellular components, and progeny cells may inherit a random fraction of genetic material (ranging from none to all), and may inherit one, none or both spindle poles. If progeny cells retain a less than complete complement of chromosomes and none or two spindle pole bodies, resulting cells are fated to die, either through loss of essential genes, through lack of spindle pole bodies, or through the catastrophic effects of a subsequent multipolar mitosis. This phenomenon is termed "mitotic catastrophe."

Mitotic catastrophe can be exploited to enhance the cytotoxic effect of anti-tumor agents on cancer cells to known microtubule poisons. Specifically, mutations in huBUB3 and functionally related genes (e.g., huBUB1) can determine the relative sensitivity of cells to microtubule poisons. In humans, the mutant status of huBUB3 and/or other genes can determine the relative cytotoxic effect of microtubule poison treatment in cancer chemotherapy. Such an effect may account for the difference between partial response and a complete remission in microtubule poison-mediated cancer chemotherapy. At the present time, the precise mechanism of tumor cytotoxicity by microtubule poisons in cancer chemotherapy is relatively poorly understood. Inactivation of huBUB3 and/or other genes can be used to increase the relative sensitivity of many tumors to microtubule poisons, such as vinblastin, taxol, vincristine, and taxotere. Treatment of tumors comprising huBUB3 mutant cells with these agents can induce gross failure of mitotic segregation of subcellular components, thereby producing profound cytotoxicity. In contrast, treatment of non-mutant cells can induce transient cell cycle delay, from which cells can immediately recover following termination of treatment. The mutational status of huBUB3 can therefore be determined to indicate which chemotherapeutic regimes should be used. For example, since wild-type huBUB3 confers resistance to microtubule poisons, the finding of a mutation in huBUB3 in a tumor indicates that such agents could be employed effectively to treat the tumor. In contrast, finding a wild-type huBUB3 will suggest use of other agents.

The invention also provides a novel chemotherapeutic regimen for treating neoplasia or its symptoms, in which tumor cells with a wild-type copy of the huBUB3 gene can be induced to undergo a lethal mitotic catastrophe effect in the presence of microtubule inhibitors. This can be accomplished by administering one or more biochemical inhibitors of huBUB3 and/or huBUB1 function, as well as one or more microtubule poisons. Inhibitors of huBUB3 and/or huBUB1 generate a transient loss of huBUB3 function analogous to that seen in genetically huBUB3-mutant cells, thereby generating a failure to properly regulate cell cycle when confronted with a microtubule poison. The resulting cytotoxicity resulting from failure of mitotic segregation would parallel that seen in huBUB3 mutant cells, with the added benefit that upon removal of the huBUB1 huBUB3 inhibitor, cells would return to a genetically stable state. In this manner, a transient inhibition of this pathway can be used to exploit the normal requirement of loss of huBUB3 function for the chemotherapeutic efficacy of microtubule poisons.

huBUB1 or huBUB3 inhibitors can be identified, for example, by kinase screening assays or by interference with huBUB1–huBUB3 binding, as described herein. Inhibitors can be added together, separately, or sequentially with the microtubule poison(s), as is desired. It is expected that the class of compounds including huBUB1/huBUB3 biochemical inhibitors described here would be used as adjuvants to normal cancer chemotherapy. Treated cells would therefore not be expected to express the constitutive genetic instability commonly observed in cancer cells. Cells transiently treated with huBUB1/huBUB3 inhibitors would be expected to return to a genetically stable state following cessation of treatment.

According to another aspect of the invention, potential drugs can be screened for utility as anti-cancer agents by the ability to suppress the expression or function of huBUB3 protein. Thus potential drugs can be contacted with cells and the expression of huBUB3 mRNA or protein monitored. This can be accomplished by well known techniques in the art, such as Northern blots, immunoprecipitation, immunoblots, etc. Any technique which utilizes a huBUB3 nucleic acid probe or an antibody specific for huBUB3 protein can be used. Other techniques, such as quantitative RT PCR can also be employed. In addition, in vitro techniques can be employed for testing the ability of candidate drugs to inhibit huBUB3 binding to huBUB1. Such assays are well within the skill of the art, once provided with the full sequence of the huBUB3 gene and protein. In addition, a yeast two-hybrid system can be used wherein one of the partners comprises all or a portion of huBUB1 and one of the partners comprises all or a portion of huBUB3. A cell which contains both of these partners can be contacted with test compounds and the loss or diminution of transactivation of the reporter gene can be monitored.

A huBUB3 subgenomic polynucleotide can also be delivered to subjects for the purpose of screening test compounds for those which are useful for enhancing transfer of huBUB3 subgenomic polynucleotides to the cell or for enhancing subsequent biological effects of huBUB3 subgenomic polynucleotides within the cell. Such biological effects include hybridization to complementary huBUB3 mRNA and inhibition of its translation, expression of a huBUB3 subgenomic polynucleotide to form huBUB3 mRNA and/or huBUB3 protein, and replication and integration of a huBUB3 subgenomic polynucleotide. The subject can be a cell culture or an animal, preferably a mammal, more preferably a human.

Test compounds which can be screened include any substances, whether natural products or synthetic, which can be administered to the subject. Libraries or mixtures of compounds can be tested. The compounds or substances can be those for which a pharmaceutical effect is previously known or unknown. The compounds or substances can be delivered before, after, or concomitantly with a huBUB3 subgenomic polynucleotide. They can be administered separately or in admixture with a huBUB3 subgenomic polynucleotide.

Integration of a delivered huBUB3 subgenomic polynucleotide can be monitored by any means known in the art. For example, Southern blotting of the delivered huBUB3 subgenomic polynucleotide can be performed. A change in the size of the fragments of a delivered polynucleotide indicates integration. Replication of a delivered polynucleotide can be monitored inter alia by detecting incorporation of labeled nucleotides combined with hybridization to a huBUB3 probe. Expression of a huBUB3 subgenomic polynucleotide can be monitored by detecting production of huBUB3 mRNA which hybridizes to the delivered polynucleotide or by detecting huBUB3 protein. huBUB3 protein can be detected immunologically. Thus, the delivery of huBUB3 subgenomic polynucleotides according to the present invention provides an excellent system for screening test compounds for their ability to enhance transfer of huBUB3 subgenomic polynucleotides to a cell, by enhancing delivery, integration, hybridization, expression, replication or integration in a cell in vitro or in an animal, preferably a mammal, more preferably a human.

The complete contents of all references cited in this disclosure are expressly incorporated herein.

The following examples are provided for exemplification purposes only and are not intended to limit the scope of the invention which has been described in broad terms above.

EXAMPLE 1

Tissue Distribution

We initially found a ~1.4 kb human cDNA fragment with homology to the *Saccharomyces cerevisiae* scBUB3 gene, which we designated huBUB3. A ~1.1 kb PCR fragment encompassing the predicted open reading frame (ORF) from this predicted cDNA fragment was amplified from a testis cDNA pool, using sense primer TWS95 (5'.GGGAGCCCAAGATGACCGGTT) (SEQ ID NO:5) and antisense primer TWS96 (AAATCCACCATTGGGGAGTACGAATTGT) (SEQ ID NO:6). This fragment was cloned (p291-45). The sequence of this cloned fragment matched the anticipated sequence derived from EST arraying, demonstrating that these ESTs are linked in the manner originally postulated.

Figure 5:
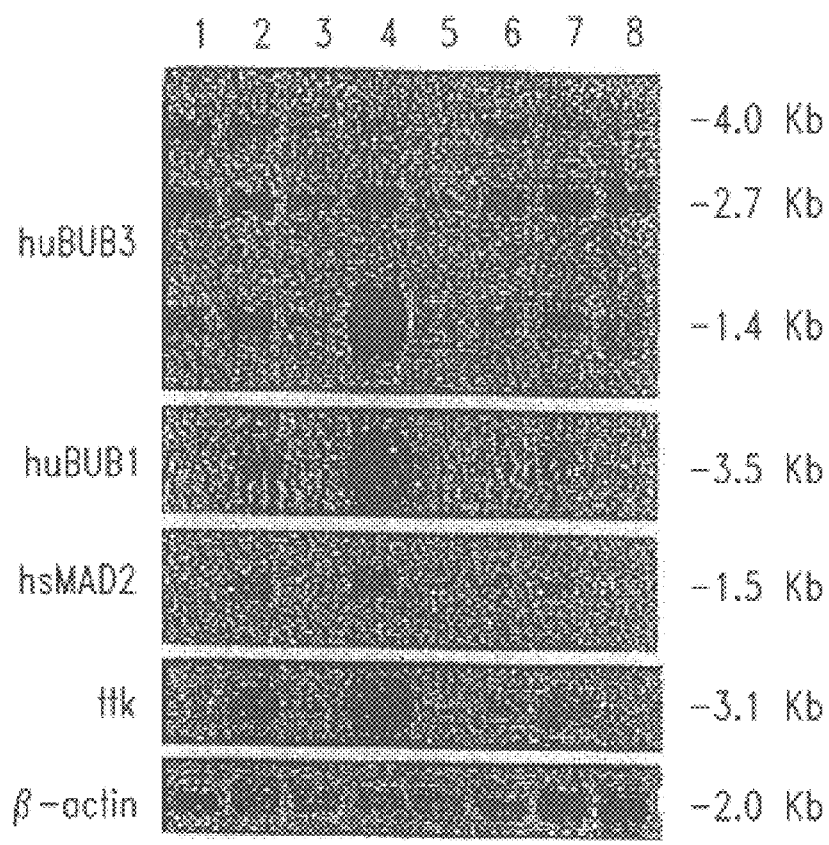
FIG. 5. mRNA expression of BUB/MAD homologs in various tissues. In separate experiments, $^{32}$P-labeled probes were prepared from cDNA fragments from indicated genes and annealed to a blot prepared from polyA$^+$ mRNA from various tissues. Actin cDNA probe (Clontech) was also annealed as a control. Lane 1, spleen; lane 2, thymus; lane 3, prostate; lane 4 testis; lane 5, ovary; lane 6, small intestine; lane 7, colon (mucosal lining); lane 8, peripheral blood leukocytes.

Tissue distribution of the huBUB3 mRNA was examined using a $^{32}$-P labeled hybridization probe derived from a 1.1 kb EcoRI fragment from p291-45. This probe was hybridized to a commercial multiple tissue Northern blot (Clontech, #7759-1), consisting of poly-a$^+$ mRNA samples from human spleen, thymus, prostate, testis, ovary, small intestine, colon (mucosal lining), and peripheral blood leukocyte. Results indicated that three human mRNA species, of ~1.4, 2.7 and 4.0 kb each hybridize to this probe. Strongest huBUB3 signal was detected with testis mRNA, specifically from the ~1.4 kb transcript. Testis is recognized as a highly proliferative tissue in adults. The next highest expression was exhibited by thymus, followed by spleen and colon, with lower but detectable expression observed in other tissues. The relative abundance of the three species of mRNA varied significantly between tissues. While in testis the ~1.4 transcript was responsible for the majority of the hybridization signal, many tissues demonstrated an equal or higher hybridization signal from the ~2.7 kb transcript. Hybridization signal from the ~4.0 transcript was generally equal or less than that observed with the ~2.7 transcript. An actin cDNA probe (Clontech, #9800-1), labeled and hybridized to the same blot, indicated that poly-a$^+$ mRNA was equally represented on the blot.

huBUB3 mRNA expression patterns were compared to those of other human homologs of BUB/MAD pathway genes, including BUB1, MAD2 and ttk, a candidate *S.* cerevisiae MPS1 homolog (FIG. 5). In these experiments, BUB1, MAD2 and ttk exhibited a characteristic expression pattern, with highest expression in testis, followed by thymus, and lower expression in colon mucosal lining and small intestine. This coordinated expression pattern suggests co-regulation of the expression of these three genes. Of the various BUB3 transcripts, the ~1.4 kb transcript follows this pattern most closely, with highest expression in testis. Testis is generally regarded as a highly proliferative tissue, and may suggest a link between mitotic activity and expression of these genes.

EXAMPLE 2

Characterization of huBUB3 mRNA

By combination of RACE (Rapid Amplification of EDNA Ends) and DNA sequencing of cloned RACE PCR products, we have further characterized the mRNA species hybridizing to the huBUB3 probe. The relationship of these species to the original 1.4 kb huBUB3 cDNA fragment we found has also been determined. Conclusions from these experiments have been confirmed by new EST entries subsequently deposited. The sequence of ~2.7 kb transcript-related cDNA clones suggest that the original 1.4 kb cDNA fragment described in our invention disclosure is derived from the ~2.7 kb transcript (FIG. 1). TWS95, a sense primer used to synthesize the ORF fragment, appears to exist as part of the sequence of the ~1.4, 2.7 and 4.0 transcripts. The antisense primer ORF primer TWS96 binds to a sequence in an exon identified in the 2.7 kb transcript. This exon is absent from the 1.4 kb transcript. The following paragraphs describe the experiments leading to these conclusions, and other details describing the characterization of cDNA products.

Using the sequence of the cloned huBUB3 ORF (plasmid p291-2), sense and antisense RACE primers were designed across the huBUB3 ORF. RACE is a PCR-based method for characterizing 5' and/or 3' ends of a cDNA. In current versions of this technique, a common primer is designed to anneal to an arbitrary adaptor sequence ligated to cDNA ends. When a single gene-specific RACE primer is paired with the common primer, preferential amplification of sequences between the single gene specific primer and the common primer occurs. Commercial cDNA pools specifically modified for use in RACE are widely available.

5' RACE PCRS were performed using antisense primers and modified cDNA templates from spleen and testis (Clontech "Marathon"). Each antisense primer produced single discrete products, suggesting a single shared 5 ' end for all three transcripts. In contrast, sense RACE primers produced multiple bands, suggesting variable ends for the 3' terminus. Given the known annealing sites of these primers, 3' RACE products were judged as sufficient to account for the synthesis of each of the ~1.4, 2.7 and 4.0 kb hybridizing transcripts. This was particularly apparent using the spleen cDNA pool, where expression of the ~1.4 kb transcript is expected to be low by previous Northern blotting analysis. From these results it was concluded that the three hybridizing huBUB3 bands arise from transcription of the same gene.

5' RACE products were cloned and sequenced, from reactions containing RACE-modified testis cDNA template and antisense huBUB3 primer TWS131 (5'.CCCTGCTTGTTTGGAAACGCTCGTATG) (SEQ ID NO:7). The sequence of these cloned 5' RACE products overlapped with public EST sequences, and suggested transcriptional initiation at variable sites within a region extending ~22–86 nucleotides upstream from the huBUB3 ATG start codon. Two 5' RACE clones, p320-1 and p320-3, exhibited additional but divergent upstream sequence. Portions of these sequences matched separate EST entries, making the identification of the 5'-most transcriptional initiation sites difficult. In three independent clones, p320-1, p320-3, and p320-8, a NotI cleavage sequence was identified near the 5' terminus. This NotI sequence is present in one overlapping EST sequence (aa305778) but is absent from 6 overlapping EST sequences, and is therefore a likely artifact. NotI sites are especially rare and the probability of identifying a site at the 5' end of a transcript is highly improbable. NotI sequence was also present in the RACE primer and may have served as a template for conversion of huBUB3 5' sequence during PCR synthesis. Consistent with this interpretation, a similar anomalous NotI sequence was found at a different position 26 nucleotides upstream in a separate clone (320-5). The final huBUB3 sequence (FIG. 1) is compiled without a NotI site.

We attempted to confirm the sequence of the 5'-most end of the huBUB3 transcript using genomic DNA sequence. A huBUB3 genomic fragment was amplified from a modified PvuII restricted genomic DNA pool (Genomewalker, Clontech), using primer TWS170 (5'.CGGGTGGCTGGTTCAGCTTGAACTCGT) (SEQ ID NO:8) in single sided PCR reactions, as described in Siebert et al. (1995). TWS170 binds in an antisense orientation to a site 10 nucleotides to the 3' side of the predicted huBUB3 ATG initiation codon. Cloned fragments were sequenced (p347-1, p347-3) and found to retain huBUB3 cDNA sequence for only 15 nucleotides before encountering a divergent DNA sequence. From these results, we conclude that the huBUB3 mRNA transcript includes an exon junction close to the 5' end of the transcript. A consensus sequence compiled from known splice junctions has been described [(CA)AG|G] (SEQ ID NO:9). Using this consensus, an exon junction can be defined within the 5' huBUB3 cDNA sequence at the site CCAAG|ATGAC (SEQ ID NO:10), where the ATG in this sequence corresponds to the predicted huBUB3 translation initiation codon.

On the basis of RACE and EST data, we propose that huBUB3 transcripts initiate primarily in a region ~11 to 54 nucleotides upstream of the predicted huBUB3 ATG start codon. The exact locations of transcription initiation sites have not been determined, but can be precisely located by established methods including RNASE protection or primer extension assay. In eight ESTs and three RACE sequences, the huBUB3 ATG start codon is preceded 12 nucleotides upstream by an stop codon (TGA) in the same reading frame. This appears to preclude the possibility that an alternative mRNA transcript can encode a protein with an extended C-terminus sharing the predicted huBUB3 ORF.

Variability of huBUB3 transcripts at the 3' terminus can result from alternative mRNA splicing, variable transcriptional termination sites, or specific mRNA degradation. To determine which of these mechanisms is responsible for the formation of the various observed huBUB3 transcripts, the sequence of the ~2.7 kb transcript was characterized using cloned spleen cDNA-derived 3' RACE products. Two highly-related clones (p331-2 and p33 1-1) with a size consistent with a ~2.7 kb transcript origin were obtained with sense primer TWS130 (5'.ACCCTCTCAGTGTCTGGAGACCGGCT) (SEQ ID NO:11). These fragments matched huBUB3 ORF sequence at the 5' end and exhibited poly-a tracts at the 3' end. The sequence immediately adjacent to the poly-a tracts was used in homology searches to identify a series of overlapping ESTs, resulting in a well-defined EST contig of 995 nt extending from the presumed 3' end of the ~2.7 kb transcript. Additional sequence data was then obtained from p331-2 and p331-1 using huBUB3 sense strand sequencing primers TWS128 (5'.CGACGGTTTCCAAACAAGCAGGGTTATG, SEQ ID NO:12); TWS148 (5'.TGATGATAATAAAACAATTCGTACTCCCCA, SEQ ID NO:13), and TWS149, (GACTCAAACAATTTGCCCTTCTGGGATCA, SEQ ID NO:14), an antisense primer derived from the EST contig, which demonstrated that this EST contig is linked to huBUB3 ORF sequences. The full predicted sequence of the ~2.7 kb huBUB3 transcript was compiled by combining this sequence with the EST contig and known 5' huBUB3 sequence (FIG. 1B). A recent search of EST databanks reveals new entries which also serve to bridge the gap between the EST contig and 3' sequence data (FIG 1A).

huBUB3 mRNA expression was also examined with the 3'-most end of the ~2.7 kb transcript, using a ~1.3 kb fragment derived from a PstI-EcoRI digest of p331-1. This fragment shares ~300 nt of 3' terminal sequence with the ~1.4 kb transcript, as discussed later. Probe prepared from this fragment was hybridized to a second commercial Northern blot (Clontech), consisting of poly-a+ mRNA samples from 8 neoplastic cell lines including: promyelocytic leukemia HL-60, HeLa cell S3, chronic myelogenous leukemia K562, lymphoblastic leukemia MOLT-4, Burkitt's lymphoma Raji, colorectal adenocarcinoma SW480, lung carcinoma A549, and melanoma G361. This probe again detected ~1.4, 2.7 and 4.0 kb bands, indicating that portions of this probe are shared by these transcripts. Strongest hybridization signal was obtained from HeLa S3, CML K562 and colorectal adenocarcinoma SW480, though hybridization was detected in all neoplastic tissues examined. Again, the relative signals from the ~1.4, 2.7 and 4.0 species were variable, with the ~2.7 kb transcript providing the strongest signal in the SW480 sample, but with equal signal from the 1.4 and 2.7 kb transcripts in HeLa. In these samples, the signal from the ~4.0 transcript was weakest. Again, hybridization with an actin probe indicated that poly-a+ mRNA was equally represented on the blot.

To characterize the nature of the ~1.4 kb huBUB3 transcript, 3' RACE products obtained using testis cDNA template and sense primer TWS132 (5.GGAGCCCAAGATGACCGGTTCTAACGA) (SEQ ID NO:15) were cloned and sequenced. Two independent but closely matched clones, p341-3 and p341-6, exhibited clear poly-a tracts at one end of a fragment of a size consistent with an origin from the 3' end of ~1.4 kb huBUB3 transcript. Six additional EST sequences can be identified with overlapping sequence. These data can be combined to define a cDNA corresponding to the ~1.4 kb transcript.

A comparison of the predicted ~2.7 kb and ~1.4 kb huBUB3 transcripts reveals that these transcripts share a 3' end, with an insertion of additional sequence (e.g., additional exon sequence) into the ~2.7 kb transcript, at a position ~1000 nucleotides from the predicted transcriptional initiation region. Thus, the ~1.4 kb transcript consists of sequence from the ~2.7 transcript. Using the previously described exon junction consensus sequence [(CA)AG|G] (SEQ ID NO:9), the likely splice junctions at which additional exon sequence appears in the ~2.7 transcript can be defined, with a 3' exon junction within the ~2.7 sequence defined as CCAAG|TCACC (SEQ ID NO:16), and a 5' junction defined as TGCAG|GTCCA (SEQ ID NO:17). The ~1.4 kb transcript then joins these sequences directly, forming the predicted exon junction CCAAG|GTCCA (SEQ ID NO:17). Because of this alternative exon structure, the ~1.4 and ~2.7 kb huBUB3 transcripts specify the production of proteins that share the first 324 amino acids, and are terminated by either 6 additional amino acids in the case of the ~1.4 transcript or 4 alternative amino acids in the case of the ~2.7 transcript. Thus, these two cDNAs predict the synthesis of essentially similar proteins, with a few divergent amino acids at the C-terminal ends (FIG. 2).

By RACE analysis, the 4.0 transcript appears closely related to the 1.4 and 2.7 kb transcripts, with a shared 5' end and additional sequence, (e.g., alternative or additional exons) at the 3' end. Cloning all the cDNA products which define the ~4.0 transcript can be completed using RACE and other tools known in the art.

A complete characterization of the huBUB3 gene, including associated intron/exon boundaries, promoters, enhancers, and other regulatory sites, will require cloning and characterization of additional huBUB3 genomic DNA. The identification of large, overlapping cloned human genomic fragments, including BACs and/or YACs, is relatively straightforward, and be readily identified by the ability to produce huBUB3-specific products in PCR-based screening reactions.

The proteins encoded by the ~1.4 and ~2.7 kb huBUB3 transcripts are structurally similar to scBUB3, retaining a WD40 repeat structure and other conserved residues (FIG. 3). A murine BUB3-like sequence was identified (Genbank U67327) with a truncated reading frame. Many huBUB3 EST databank entries (FIG. 1A) were annotated with homology to *Schizosaccharomyces pombe* rae1 gene. A human homolog of the sp-rae1 (hu-rae1) was previously identified in the databanks. A sequence comparison indicates this gene is clearly distinct from the huBUB3 gene. Based on analogy from known yeast gene functions, we anticipated a partner to the previously disclosed huBUB1 gene would exist. We have now identified a physical interaction between the product of this huBUB3 gene with the huBUB1 gene product (see below), confirming that the huBUB3 gene described here is the anticipated ligand for huBUB1. Based on sequence comparisons, we propose that the closely related rae1 genes from human and *S. pombe* may be functionally related to the structurally related *S. cerevisiae* YET7 gene product.

EXAMPLE 3

Developmental Expression

Human EST deposits of clear huBUB3 origin include numerous fetal cDNA sequences, strongly suggestive of expression in these tissues. This is consistent with our earlier conclusions that huBUB3 may be active in proliferating tissues.

EXAMPLE 4

Chromosomal Locus of huBUB3 huBUB3 was successfully mapped to a chromosomal locus in our lab. These results indicate that huBUB3 is located at a site known by other work to be frequently mutated in cancer cells. This chromosomal location appears to be involved in the genesis of cancers from a wide variety of tissue types, producing both solid and hematologic neoplasms. Experiments leading to these conclusions are described in the following paragraphs.

a huBUB3 cDNA sequence search of the NCBI Sequence Tagged Site (STS) database to determine if huBUB3 is associated with known STS sequences produced negative results. The huBUB3 map position (10q24) was subsequently identified by Radiation Hybrid (RH) mapping (Walter et al., 1994, *Nature Genetics* 7:22–28). Commercially prepared genomic DNAs from individual hybrid hamster cell lines harboring human irradiated chromosomal fragments (Stanford G3 panel, Research Genetics) were used as templates in PCR reactions to identify individual hybrid cell lines carrying huBUB3 DNA. Three separate mapping experiments were conducted, using primer pairs engineered from 3' untranslated (UTS) ~2.7 kb huBUB3 transcript sequence data (TWS157/TWS158, TWS172/TWS173, and TWS176/TWS177).

| Primer | sequence |
|---|---|
| TWS157 | 5'.TCATTGCAGGTCCACCTAATCATCCTGTGAAAGTGGTT (SEQ ID NO:18) |
| TWS158 | 5'.ACTAGGGGACAGAAGGGGAAATACGTCAGACTACT (SEQ ID NO:19) |
| TWS172 | 5'.TTTGGGCAAACAAAATTGGAGGGCAAGTGAC (SEQ ID NO:20) |
| TWS173 | 5'.ACCAGCAAAAGAAACAAATGGCTCACGAGCCT (SEQ ID NO:21) |
| TWS176 | 5'.TGCAGGTCCACCTAATCATCCTGTGAAAGTGGTT (SEQ ID NO:22) |
| TWS177 | 5'.ACAGAAGGGGAAATACGTCAGACTACTGTACAGGG (SEQ ID NO:23) |

In each experiment, human/hamster hybrid genomic templates which produced the anticipated huBUB3 genomic PCR products were recorded. For scoring purposes, results were submitted to the Stanford Human Genome Center (SHGC) Web server. Data from each of the three primer pairs produced similar map locations, indicating strong linkage of huBUB3 sequences to STS locus SHGC-13269. Using the SHGC Web server, STS markers D10S216 and D10S244E were identified as closely linked markers for SHGC-13269. Using the Entrez genome feature of the NCBI web site, SHGC-13269 and linked markers were all found to map to chromosomal locus 10q24, indicating that this is the chromosomal location of the huBUB3 gene.

10q24 is the known chromosomal location of recurrent cancer-related genetic rearrangements, as cataloged in Mitelman et al. *Nature Genet.* (Supp.) pp. 417–74 (1997). A literature search indicated that other potential cancer-related genes mapped in and near 10q24 include Wnt8B, FGF8, Fas, HOX11, LYT10, MXI1. Cancer-related genes are functionally classified as either oncogenes or tumor suppressor genes depending on the known role of the gene product in cancer. In cancer, HOX11 and LYT10 function as oncogenes, and can each be transcriptionally activated by cancer-related chromosomal translocations. These translocations serve to bring an active promoter into the region of these normally quiescent genes, resulting in abnormal accumulation of a gene product which would normally be absent. Thus, the abnormal presence of an activity associated with an oncogene product contributes to the phenotype of a cancer cell. In contrast, the phenotypes of tumor suppressor genes suggest that they are active in normal cells, and that in cancer cells their gene products are non-functional. Cancer-related mutations in a tumor suppressor gene are generally inactivating mutations, commonly including deletions, truncations, and other mutations.

By analogy to the known function of scBUB3 in yeast, we anticipate that the absence of huBUB3 activity in human cells should reduce the fidelity of mitosis, possibly resulting in increased aneuploidy and genetic instability. Aneuploidy, a state which describes the absence of a correct genetic complement of chromosomes in a given cell, is exceptionally rare in normal human cells, but is observed at much higher frequencies in cancerous cells. The function of huBUB3 may be required in normal cells for suppressing aneuploidy. Cancer-related mutations in huBUB3 might therefore increase the genetic instability of cells, contributing to an unstable phenotype and karyotype commonly observed in tumor cells. We propose that the huBUB3 gene may behave in human cells as a tumor suppressor gene, such that cancer-related alterations in the huBUB3 gene would inactivate the huBUB3 gene product. Inactivating mutations, including chromosomal deletions, might therefore be expected to be associated with the huBUB3 locus in cancer cells.

In cancer, recurrent deletions of chromosomal loci have been used to infer the locations of important tumor suppressor genes. We find that the chromosomal site of huBUB3, 10q24, is recorded in the literature as the most heavily modified site of cancer-related karyotypic variation on chromosome 10. The resolution of karyotypic analysis is limited to relatively gross chromosomal deletions, and the frequency of cancer-related mutations of individual genes within this region are likely to be much higher. Recurrent karyotypic deletions of this site have been observed in neoplasms of both solid and hematological origin (Mitelman et al. 1997).

Hematological neoplasms exhibiting recurrent deletions of 10q24 include: Chronic Lymphoproliferative Disorder (CLD), Non-Hodgkins Lymphoma (NHL), Acute Lymphoblastic Leukemia (ALL), and Acute Myeloid Leukemia (AML). Non-hematological neoplasms with recurrent 10q24 deletions include: malignant epithelial neoplasms consisting of various adenocarcinomas originating in ovary, breast, large intestine, and prostate; transitional cell carcinomas of bladder tissue; and germ cell tumors of testis tissue. Recurrent 10q24 deletions have been recorded in malignant mesenchymal neoplasms (mesothelioma) and neuroglial neoplasms (astrocytoma). Recurrent 10q24 deletions have also been recorded from benign mesenchymal neoplasms of the uterus (leiomyoma). Of these deletions, many were recorded as the sole karyotypic abnormality detected in the neoplasm.

In the cases of malignant meningioma, prostate adenocarcinoma and glioma, the role and extent of modification of this chromosomal region was examined by extensive karyotyping and by Loss-Of-Heterozygosity (LOH) mapping. The minimal LOH region defined in a study of 117 gliomas included STS markers D10S587 and D10S216 (Rasheed et al. 1995). As previously noted, D10S216 was identified by RH mapping as within the immediate region of the huBUB3 gene. This suggests that the huBUB3 locus is subject to recurrent deletions and other potential modifications in cancer.

Genes are present in two copies in normal human diploid cells. In cancers exhibiting karyotypic deletions of a tumor suppressor gene locus, a single allele may be subject to deletion, and the remaining allele may be inactivated through point mutation. Occasionally, a tumor suppressor gene is inactivated by a dominant-negative mutation, in which a single mutated allele may suppress the activity of a second, non-mutated allele. This effect can occur through interaction of a mutant gene product with the gene product of the remaining allele, or through interaction with other proteins in a multi-protein complex. In these scenarios, these interactions block the activity of the product from the non-mutated allele. With respect to huBUB3, both scenarios are possible. In this work, we have demonstrated that huBUB3 protein forms a multi-protein complex, through interaction with huBUB1 gene product, as described in the following section.

Of known genes mapped to 10q24, MXI1 has been suggested as a potential tumor suppressor gene. One study associated mutations of MXI1 with prostate cancer, while a separate study of 40 pancreatic adenocarcinomas failed to find any correlation with MXI1 inactivation. These results suggest MXI1 inactivation is insufficient to explain the general tumor suppressor effect associated with deletions in this region.

The precise role of huBUB3 in the genesis of individual cancers remains to be determined, but this mapping data provides strong inferential support for the idea that the huBUB3 locus may function as a tumor suppressor gene in cancer.

EXAMPLE 5

Chromosomal Locus of huBUB1

Using somatic cell hybrids, chromosome 2 has been identified as the location of the huBUB1 gene, mapped more specifically using RH (radiation hybrid) mapping to a site near STS marker D2S176 (Pangilinan et al. 1997). Another study independently mapped BUB1 to 2q12-14 by FISH (Cahill et al. 1998). We RH mapped the 3' end of BUB1 using primer pair TWS169 (5'.ACCAAGAGGGTC ATTGCCCTTGTAGCTCTGCATGT) (SEQ ID NO:25) and TWS185 (5'.GGATGCAGAGTTCTCTGGGAGCTCTG TGGCTGATT) SEQ ID NO:26), which anneals to intron sequence near the 5' end of the BUB1 ORF. Our own BUB1 RH data produced significant scores when a chromosome 2 localization was included, suggesting linkage (50 cR_10, 000, LOD 3.5) to STS locus SHGC-37233. Markers SHGC-37233 and D2S176 are separated by a gap in the current Stanford G3 RH map, suggesting BUB1 may lie within this interval. SHGC-37233 and D2S176 are assigned to 2p13-14, suggesting huBUB1 lies very near the centromere of Chr. 2.

EXAMPLE 6

Antisense Constructs

We engineered an antisense construct of the huBUB3 gene (p291-45), consisting of a ~1.0 kb PCR fragment corresponding to the huBUB3 ORF cloned into a commercial expression plasmid vector pCR3.1 (Invitrogen). This ~1.0 kb PCR fragment was amplified from a RACE-modified testis cDNA pool using sense primer TWS95 (5'-GGGAGCCCAAGATGACCGGTT) (SEQ ID NO:5) and antisense primer TWS96 (5'-AAATCCACCATTGGGGAGTACGAATTGT) (SEQ ID NO:6). Upon characterization of various cDNAs, it was determined that the ~1.4 kb transcript lacks a priming site for TWS96. TWS96 matches sequence present in the ~2.7 kb cDNA (and possibly also the ~4.0 transcript, which has not been fully characterized as of yet). p291-45 is designed to utilize the strong viral CMV promoter and the bGH transcriptional terminator in transfected mammalian cells for antisense huBUB3 expression and transcriptional termination. The vector includes a neomycin resistance marker gene for selection of stable transfectants in mammalian cell lines, along with additional sequences required for propagation in bacteria.

This construct, and an essentially similar sense huBUB3 expression construct (p291-2), are being tested in cell lines to determine their ability to produce relevant phenotypes in various assays. Relevant phenotypes are discussed below. Additional constructs expressing huBUB3 fusion proteins have been produced as well. These plasmids, including sense, antisense and fusion protein constructs, can be used for gene therapy. We have injected p291-2 directly into mice, and results suggest that huBUB3 was expressed in murine tissue. Expression of a huBUB3 gene in tissues can be exploited for therapeutic effect.

EXAMPLE 7

Therapeutic Applications of the Gene/protein

To aid in defining therapeutic applications, we are currently examining cells for any or all of four phenotypes that we anticipate may be associated with huBUB3; (1) cell viability, (2) cell cycle control, (3) apoptosis, and (4) transcriptional regulation. Cell viability phenotypes are anticipated based on the known function of yeast scBUB3 in maintaining cell viability in the presence of microtubule poisons. Cell cycle phenotypes are also anticipated based on studies of yeast scBUB3. Research on the p53 and ATM genes, which function in a functionally analogous pathway activated in response to DNA damaging agents, suggest to us that in multicellular organisms, including humans, huBUB3 may be associated with apoptosis and transcriptional regulation. Cell cycle arrest and apoptosis are known consequences of treatment of cultured human cells with microtubule poisons, and we anticipate these phenotypes may require the function of the huBUB3 gene. In various tests, these cellular phenotypes and associated potential therapeutic applications may prove to be either microtubule-poison drug dependent, or drug independent.

Normal human and yeast cells pause in cell cycle in the presence of microtubule poisons. Microtubule poisons interfere with the proper formation and dynamics of the microtubule organizing centers (also called centrosomes, spindle pole bodies), associated microtubules, and other microtubule-associated proteins. Late in each cell division, microtubules become attached to paired chromosomes at a chromosomal structure termed the kinetochore. These microtubules in turn become associated with centrosomes at the opposite poles of a cell. In preparation for mitosis, these microtubules interact with the opposed centrosomes within the cell, forming what is termed a mitotic spindle. During the metaphase stage of mitosis, microtubules direct the migration of the individual chromosomes towards a point midway between the centrosomes, forming the metaphase plate. Following proper arrangement of the chromosomes to form the metaphase plate, a signal is generated which allows the paired chromosomes to separate and migrate towards opposite centrosomes (chromosome segregation), in a microtubule-dependent process. Once chromosomes have been properly segregated to opposite poles of a cell, cells begin cytokinesis, the process of dividing the cell into two progeny cells. Cytokinesis is the process by which the cytoskeleton of a cell is modified to cause a constriction of the plasma membrane in the region between the segregated chromosomes, as a precursor to the formation of two independent progeny cells. The cytoskeleton of cells consists of actin and other protein components. The cytoskeleton exists independently from microtubules. Any effect of microtubule poisons on cytoskeletal dynamics is therefore indirect.

Microtubule poisons disrupt the formation and dynamics of microtubules, and in normal cells, a cell cycle delay ensues. Thus, the process of cytokinesis is inhibited in response to microtubule poisons in normal cells. This delay presumably exists to allow time for the mitotic spindle to be repaired prior to attempting cytokinesis.

The mechanism by which disruption of microtubule function results in inhibition of later mitotic events including cytokinesis has been studied genetically in the budding yeast, *Saccharomyces cerevisiae*. Yeast cell cycle response to microtubule poisons requires the activity of *S. cerevisiae* scBUB3. Yeast cells defective in scBUB3 function are sensitized to the presence of microtubule poisons. These mutant scBUB3 cells fail to detect the absence of mitotic spindle function, and proceed directly into cytokinesis in the absence of chromosome segregation. The result of cytokinesis in the absence of proper chromosome segregation is the production of progeny cells that inherit a random assortment of genetic material. Since many individual genes are essential for viability of cells, failure to inherit an accurate and complete complement of chromosomes results in subsequent loss of viability and death of progeny cells. This loss of viability of scBUB3-mutant yeast cells in the presence of microtubule poisons is therefore directly associated with a failure of cell cycle control. This process of cell death through failure to regulate cell cycle progression in response to control signals has been generally termed "mitotic catastrophe".

In humans, the huBUB3 protein or gene or variants thereof can be used in therapeutic applications to stimulate a cell cycle response. A delivery method which resulted in an excess of huBUB3 activity in recipient cells may cause a permanent cell cycle arrest, for example, without a requirement for microtubule poisons. Alternatively, delivery of huBUB3 augments the cell cycle delay phenotype of microtubule poison-treated cells. This can be useful in inhibiting the growth and division of hyperplastic tissues, including cancer. Any application where inhibition of cell growth is desired can be achieved through methods which increase the activity of huBUB3 in cells. In these therapeutic applications, DNA or protein can be used directly, delivered by injection, by gene gun using huBUB3 protein, RNA or DNA coated particles, by electroporation, or by a variety of other recognized methods designed to increase uptake of exogenously provided materials into cells. Gene-specific delivery methods for delivery of huBUB3 DNA and/or RNA can include viral-based gene delivery vectors, e.g., retroviral, AAV and other hybrid vectors.

We expect that knowledge of the nucleotide sequence of huBUB3 will be useful in the design and identification of huBUB3 small-molecule agonists, through random screening of chemical libraries for compound which modify the activity of huBUB3 protein or huBUB3 transcription, or through rational chemical design approaches using the structure of huBUB3 protein and known huBUB3 ligands (e.g., huBUB1). In mutant huBUB3 cells, as may occur in cancer or other hyperplastic syndromes, cells may respond to huBUB3 protein or DNA by cell cycle arrest. This can be used therapeutically to retard the growth of cancer or other hyperplastic tissues. Alternatively, huBUB3 protein or gene may restore normal huBUB3 function to mutant human cells, allowing cell cycle arrest in a drug-dependent fashion. Genetic syndromes resulting from germ-line transmission of huBUB3 mutations may be treatable by huBUB3 gene therapy in utero, for example, with huBUB3 genes or variants thereof.

Knowledge of the huBUB3 gene may allow the rational design of viral vectors which require the absence of huBUB3 function. An instance of use of modified adenoviral vectors which requires absence of p53 function has been described. In this cases, viral replication and death of infected cells is restricted to mutant cells, sparing normal tissue.

Additional arguments can be made for therapeutic applications based on apoptotic response of cells to huBUB3 activity. Many cell types have been described which undergo an apoptotic response to microtubule poisons. Cells which cannot repair damaged mitotic spindles may be targeted for programmed cell death by apoptotic signaling pathways that may involve the huBUB3 gene. Delivery of huBUB3 gene, protein or small molecule agonist may be sufficient to trigger apoptosis in cells. This can be useful in eliminating hyperplastic tissues, including cancer, though apoptotic cell death, for example. Alternatively, delivery of huBUB3 gene, protein or small molecule agonist may sensitize cells to the apoptotic effects of microtubule poisons, resulting in enhanced cell death in combined treatments involving these agents.

Similar therapeutic applications based on transcriptional response of cells to huBUB3 activity may also be used. While transcriptional targets of huBUB3 regulation have not been identified, the functions of these transcriptional targets may prove essential to cell viability, cell cycle control, apoptosis and/or other uncharacterized phenotypes. Delivery of huBUB3 gene, protein or small molecule agonist may be sufficient to trigger transcriptional regulation of target genes in cells, the utility of which is currently unknown with respect to therapeutic applications. The constructs described here can be used to facilitate discovery of transcriptionally regulated genes, by using PCR differential display or other techniques to identify differential representation of specific mRNAs in cells in which huBUB3 activity is overexpressed, or under-expressed, as may occur using antisense constructs.

An alternative approach to the design of huBUB3-based therapeutics involves the engineering of versions of the huBUB3 protein or gene which inhibit the function of the native huBUB3 gene within cells (dominant negative phenotypes). These constructs can be used to confer a "mitotic catastrophe" on cells treated with microtubule poisons. Alternatively, small molecule inhibitors that interact with huBUB3 and prevent binding of ligands (e.g., huBUB1) can be developed with similar applications in mind. This is likely the most promising avenue for development of huBUB3-based therapies. Modified huBUB3 proteins or genes of this class might include huBUB3 antisense constructs, transcript-specific ribozymes, truncation variants, point mutants, insertion mutants, and/or fusions with other proteins, to produce variant huBUB3-derived molecules which inhibit the activity of native huBUB3 within cells. These genes or proteins can be delivered directly, as previously described, or in the form of nucleic acid constructs, including recognized gene therapy vectors and other nucleic acid delivery vehicles. By inhibiting the activity of native huBUB3 in cells, huBUB3-associated phenotypes can be blocked.

Because in yeast scBUB3 is required for cell viability following treatment with microtubule poisons, these inhibitors of huBUB3 function may induce selective cell death upon exposure to microtubule poisons. In cancer cells expressing native huBUB3 protein, enhanced cell death upon exposure to microtubule poisons can be of great clinical utility. Other applications include treatment of other hyperplastic disorders in combination with microtubule poisons.

EXAMPLE 8

Diagnosis, Prognosis, Therapeutics, and Drug Screening huBUB3-based diagnosis of tumor samples can predict the outcome of treatment with microtubule poisons and can therefore be used to decide an appropriate therapeutic regimen, tailored to the individual patient. huBUB3 diagnostic tests can include Protein Truncation Test, SSCP analysis, sequence analysis of PCR products, and other tests. If diagnostic tests determine that the huBUB3 locus is inactivated through mutation of both alleles, or through production of dominant negative mutations, treatment of patients with commonly used microtubule poisons may result in severe regression of the tumor through the effects of "mitotic catastrophe" on cell viability, as described in the therapeutic applications section. Alternatively, if diagnostic tests determine that the BUB3 locus is functionally active in tumor cells, transient or prolonged treatment of patients with microtubule poisons may result in a delay in tumor progression, through the anticipated cell cycle effects of huBUB3 activity, rather than producing substantial tumor regression. In this instance, a clinician may elect to omit microtubule poison drug treatment, as side effects of treatment with these drugs may limit their therapeutic value in this instance. In a third instance, the huBUB3 locus is diagnosed as functionally active in a tumor, and based on this diagnosis, a decision may be made to treat patients with a combination therapy consisting of huBUB3 inhibitors and microtubule poisons. This would serve to induce a mitotic catastrophe effect in cells which normally would be resistant to this effect. This treatment can be repeated for additional reductions in tumor burden, as upon recovery from treatment cells retain wild-type huBUB3 genes.

With respect to discovery of novel drugs, the protein product of huBUB3 or variants thereof can be produced, and biochemical assays can be designed based on knowledge of this gene and gene products. These drugs can include chemical inhibitors of huBUB1 and huBUB3 interaction, or inhibitors of a huBUB1/huBUB3 kinase.

EXAMPLE 9

Antibodies

Antibodies directed against huBUB3 protein were produced in mice by direct DNA immunization. These antibodies may be useful in diagnostic tests, including Protein Truncation Test, and in various assays of huBUB3 function, including study of interacting proteins, and in assays of huBUB3 function in cells, cell extracts and other in vitro tests. Diagnostic and therapeutic applications may also be identified for antibodies or antibody fragments which recognize huBUB3. It may be possible to produce huBUB3-reactive antibodies using muBUB3 sequences.

To produce antibodies, plasmid 291-2, a huBUB3 expression construct, was purified from E. coli host strain XL-1-blue (Invitrogen) and used to immunize mice. Direct DNA immunization allows the production of highly-specific antibody in the absence of protein immunogen. Typical protein-based immunizations require highly-purified protein, and may result in the production of serum with antibody with affinity to minor protein contaminants in the immunogen preparation. In contrast, immunization with purified nucleic acids has the advantage that antibodies are produced only to the proteins encoded on the plasmid. Any residual contaminating bacterial nucleic acids are not expressed due to the lack of specific regulatory sequences required for expression in mammalian cells. Previous published data has shown that muscle tissue is competent for expression of injected DNAs.

p291-2 is based on expression plasmid pCR3.1 (Invitrogen), and includes necessary mammalian expression elements to allow the production of huBUB3 (~2.7 kb variant) and the neomycin resistance gene product within recipient cells. Endotoxin-free DNA was prepared using a kit (Qiagen). Following collection of pre-bleed serum samples, 5 Balb/c mice were immunized via intra-muscular injection of 100 μg of purified DNA, on three separate occasions (50 μg per each tibialis anterior muscle per injection). The second and third immunizations followed 28 and 56 days after the first injection, respectively. Two production bleed samples were collected from each mouse, at days 42 and 72 following the first injection.

Serum samples were used in Western blotting assays of cultured human cell extracts to determine if huBUB3 antibodies were produced in animals. Extracts from DU145 prostate carcinoma cells were separated by SDS-PAGE and transferred to a support membrane. Second production bleed serum from one immunized mouse was found to strongly react with a single band from these extracts. This band was not detected in parallel experiments using pre-immune serum from the same animal and was absent or barely detectable using post-immunization serum samples from the other animals. Because untransfected DU145 cells are not expected to express neomycin resistance gene product, this band is interpreted to represent the presence of antibodies directed against huBUB3 in the serum from this animal. These antibodies are presumed to arise from expression of huBUB3 in mouse tissues.

huBUB3-reactive antibodies can be used in immuno-precipitations to identify interacting proteins, which can become targets for further discovery efforts and therapeutics and diagnostics. huBUB3 antibodies may be used to immuno-precipitate huBUB1/huBUB3 complexes from cell extracts for use in in vitro kinase assays to identify potential huBUB1 kinase substrates and kinase inhibitors in a small molecule screening effort. Additional proteins bound to huBUB1 and/or huBUB3 may be identified in extracts using these reagents and purified by recognized techniques to identify and characterize novel proteins or to assign novel activities to known proteins which function in a complex with huBUB3. Antibodies can be used to examine huBUB3 from tumor cells directly, for mutations which produce protein truncation variants in Western blotting experiments (protein truncation test). Also, huBUB3-reactive antibodies may have a therapeutic effect in humans. Cells which overexpress huBUB3 in a patient may react with antibody, allowing the selective elimination of these cells through normal immunological response. Antibody production might be achieved though DNA immunization of humans, as described above, or through treatment with antibody produced in cultured cells or animals. The production of huBUB3-reactive monoclonal antibodies is also possible, through recognized techniques for isolation and propagation of huBUB3 antibody-producing cells. The advantages of monoclonal antibodies are well recognized and documented elsewhere. Gene therapy vectors based on the expression of huBUB3-reactive antibodies or antibody fragments or fusion proteins may be produced for intracellular expression of huBUB3-reactive proteins. Within cells, these antibody-related proteins can be used in the same manner as dominant-negative nucleic acid and protein variant inhibitors of huBUB3 and small molecule chemical inhibitors of huBUB3 function.

EXAMPLE 10 huBUB1 Binds to huBUB3

We have found evidence for the physical interaction between huBUB3 and huBUB1 gene products. This interaction was predicted from yeast data, where huBUB1 and huBUB3 form a protein complex with kinase activity. The huBUB1 gene displays a conserved domain at the C-terminus proposed to be required for interaction with huBUB3. By demonstrating this physical interaction, we confirm that the huBUB3 gene product is the appropriate ligand for the huBUB1 protein. This experiment serves to illustrate the utility of knowledge of the huBUB3 sequence in discovery purposes in the discovery of novel protein-protein interactions. This discovery may also serve as the basis for a biochemical assay for inhibitors of huBUB1/huBUB3 interaction.

As part of these experiments, a huBUB3-FLAG fusion expression construct (p322-1) was produced, by insertion of synthetic FLAG immuno-peptide coding sequences between the PinAI and HindIII sites of p291-2. In this construct, a synthetic N-terminal methionine codon is followed by sequence coding for three "FLAG" immuno-peptide repeats separated by glycine codons. This segment is in turn immediately followed by 5 glycine codons and is fused in-frame to the second codon of the native huBUB3 N-terminus, replacing the native N-met residue. The product is a plasmid encoding a FLAG-huBUB3 protein fusion. Monoclonal antibody reagents which recognize the FLAG sequence (DYKDDDK) (SEQ ID NO:24) are commercially available (Kodak).

Figure 4A:
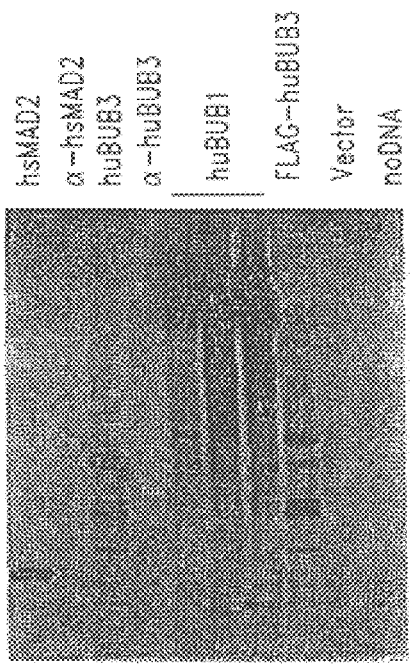
FIG. 4. FLAG-huBUB3 binds to huBUB1. (A) Plasmids with various inserts were transcribed and translated in the presence of $^{35}$S with the aid of a T7 RNAP-based transcription/translation kit (Promega). Translation products were then separated on 10–20% SDS-PAGE gels and autoradiographed. (B) Co-immunoprecipitation assay. Combinations of plasmids were co-translated and soluble translation products were subjected to FLAG immunoprecipitation, using M1 anti-FLAG monoclonal antibody conjugated to agarose (Kodak). Fractions of supernatant and agarose bead pellet fractions were separated by SDS-PAGE and autoradiographed, as indicated.

Various huBUB3 and huBUB1 plasmids were subjected to coupled in vitro transcription/translation reactions in the presence of 35-S labeled methionine (T7 polymerase-directed TnT kit, Promega), to produce radioactive protein products which can be followed in various assays (FIG. 4). The vector for these plasmids includes a bacteriophage T7 binding site which allows in vitro synthesis of transcripts of the genes under study. 5 µl labeling reactions contained 15 to 100 ng of each plasmid. Following incubation at 30 C. for ~1.5 hr, 3 µl of TNES buffer (50 mM Tris-Cl pH 7.5, 2 mM EDTA, 100 mM NaCl, 1% NP-40) was added and insoluble material was removed by centrifugation. Agarose beads with anti-FLAG monoclonal antibody coupled to them (Kodak) were washed with TNE (equivalent to TNES without NP-40) and added to the soluble fraction. Antibody binding reactions were incubated at room temperature ~1 hr, then briefly centrifuged and a 5 µl supernatant fraction was collected. Pellets were washed once with TNES and twice with TNE before resuspension in SDS-PAGE sample buffer. Aliquots of supernatant and washed pellet fractions were then analyzed by SDS-PAGE on 10–20% gradient gels. Dried gels were then autoradiographed (FIG. 4).

Figure 4B:
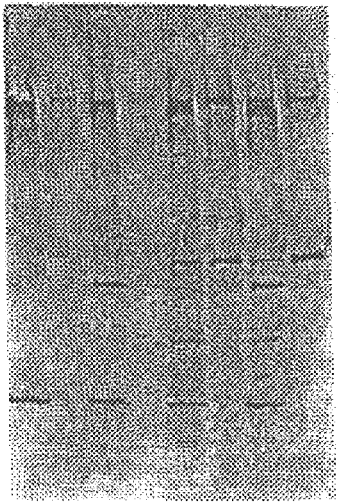

$^{35}$S labeled protein corresponding to the products of various genes of interest was produced in in vitro translation reactions. Proteins were expressed either singly (FIG. 4A) or in combinations (FIG. 4B). Preliminary experiments demonstrated that of the various plasmids analyzed, only the plasmid coding for the FLAG-epitope tagged huBUB3 fusion protein (p322-1) produced material that was enriched in pellets following anti-FLAG immuno-precipitation. In reactions where plasmids were combined, again, only reactions which included the FLAG-huBUB3 plasmid produced enrichment of labeled protein in immuno-precipitation pellets (FIG. 4B). When FLAG-huBUB3 plasmid was combined with a huBUB1 coding plasmid (p337-50), huBUB1 was co-precipitated along with the FLAG-huBUB3. This indicates that huBUB3 is a ligand for huBUB1. When plasmid encoding huBUB3 was added to reaction containing FLAG-huBUB3 and huBUB1 plasmids, only labeled FLAG-huBUB3 and huBUB1 were observed to be enriched in the pellet. These results are consistent with a model in which huBUB3/huBUB1 complexes retain a single monomer of huBUB3 per complex. In this manner, the labeled FLAG-huBUB3 protein competes with huBUB3 for a single binding site in the complex, such that prior binding of labeled FLAG-huBUB3 precludes association with huBUB3 protein. These results are also consistent with a model in which huBUB3 does not self-associate.

In yeast, scMAD2, scMPS1, scBUB1 and scBUB3 are each proposed to function in a microtubule poison signaling pathway. We also determined whether the known gene hsMAD2, a structural homolog of scMAD2, can interact with huBUB1 and FLAG-huBUB3 in a ternary protein complex. We did not detect any binding of the hsMAD2 gene product to FLAG-huBUB3/BUB1 complexes in these experiments. Co-translation of the hsMAD2 gene was not required for assembly of huBUB1/FLAG-huBUB3 complexes, shown in other experiments.

These results can be used to develop small molecule inhibitors based on activity in a huBUB1/huBUB3 interaction assay. The huBUB1 and scBUB1 genes exhibit strong homology to known kinases. In yeast, the scBUB1/scBUB3 complex is known exhibit protein kinase activity, with literature references recording scBUB1 auto-phosphorylation activity and kinase activity towards scBUB3. Our intent is to develop protocols which make use of some of the reagents and interactions described here to identify inhibitors or activators of huBUB1/huBUB3 signaling, and anticipate the development of in vitro kinase assays using huBUB1/huBUB3 protein complexes.

EXAMPLE 11

Subcellular Localization of Over-expressed BUB1 and BUB3

Anti-huBUB3 serum was generated directly by genetic immunization with huBUB3 expression plasmid p291-2. We find that genetic immunization with naked DNA provides a useful alternative strategy for generating antibody when protein immunogen is limiting. With this serum, BUB3 expression was monitored in DU154 prostate carcinoma cells transiently transfected with either BUB3 or FLAG-BUB3. In both cases, bright BUB3 staining was limited to mitotic nuclei, as evidenced by the presence of condensed DAPI-stained chromatin. Pre-immune serum failed to produced bright staining in BUB3-transfected cells. Similarly, bright staining was absent in cells transfected with pCR3.1 vector. Among brightly stained mitotic nucleic, clear prometaphase, metaphase, and telophase forms could be identified.

Cells were also transiently transfected with HA-BUB1 plasmid and the relative distribution of HA-BUB1 was determined using anti-HA antibody. Brightly HA-BUB1 stained cells also consisted entirely of mitotic nucleic. Control cells transfected with pCR3.1 vector failed to exhibit bright HA-BUB1 staining. These results suggest HA-BUB1 expression is also limited to mitotic nuclei.

The observation of a mitosis specific staining pattern for these proteins was somewhat surprising. Transcription from the pCR3.1 expression vector is not known to be cell cycle regulated. HA-BUB1 and BUB3 overexpression may each cause accumulation of cells in mitosis. The mitotic indices of HA-BUB1, BUB3 and pCR3.1 vector transfected cells in these experiments were therefore compared. These indices were similar, suggesting that expression of these proteins did not induce an excess of mitotic cells.

Alternatively, these proteins may be regulated by post-translational processing. This possibility is intriguing, as numerous cell cycle regulatory proteins are known to be subject to cell cycle-regulated proteolytic degradation. In both HA-huBUB1 and -huBUB3 transfected cells, bright staining of clear telophase figures was seen, suggesting that regulation of these proteins may occur after anaphase chromosome separation.

EXAMPLE 12 huBUB1 and huBUB3 are Nuclear Antigens

DU145 prostate carcinoma cells were transiently transfected with various plasmids in the presence of LT-1 transfection reagent (Mirus). After two days of growth, cells were fixed 5 min in cold methanol, shifted to room temperature, washed with PBS/0.1% Triton X-100 three times, then blocked and permeabilized with 1% BSA in PBS/0.1% Triton X-100 for 30 min at room temperature. Cells were sequentially incubated with primary and secondary antibodies in 1% BSA in PBS/0.1% Triton X-100. Following antibody reactions, slides were washed with PBS/0.1% Triton X-100.

Nuclei were stained by 10 min incubation in 0.05 mg/ml 4'-6-diamidono-2-phenylindole (DAPI). Stained cells were imaged digitally using a Zeiss axiovert fluorescence microscope equipped with a high-resolution CCD camera (Xillix Corporation). Image data was processed using SCILImage (Delft, Netherlands) to subtract background fluorescence and enhance contrast. Cytometric classification for cell cycle distribution was done using nuclear morphology and DAPI staining distribution and intensity.

The site of accumulation of HA-huBUB1, -huBUB3, and FLAG-huBUB3 proteins was determined in these cells. Results suggest that these proteins accumulate in the nucleus, consistent with the formation of huBUB1 and huBUB3 complexes.

Relatively diffuse HA-huBUB1 and huBUB3 nuclear staining was observed, likely due to relatively high expression levels. Somewhat surprisingly, bright huBUB1 and huBUB3 immunostaining was restricted to M phase cells, in which condensed chromatin was readily observed. Because in both cases proteins were expressed from a non-native CMV promoter, these results suggest that accumulation of huBUB1 and huBUB3 proteins may be regulated. The widespread role of the APC in turnover of mitotic regulatory proteins suggests a potential role for ubiquitin-mediated proteolysis in regulating the accumulation of huBUB1 and huBUB3 in the cell cycle. huBUB1 and huBUB3 overexpression were each detected in clear telophase figures, suggesting that degradation of these proteins was not required for anaphase initiation.

These staining patterns differ from those reported by Taylor et al., who reported that a GFP-BUB3 fusion protein was expressed as a diffuse nuclear antigen in interphase cells, becoming specifically localized to kinetochores during prophase and prometaphase, and finally becoming diffusely localized throughout the cell in metaphase and anaphase (Taylor et a. 1998). Overexpression of murine BUB1disrupted these patterns, causing accumulation of overexpressed huBUB3 in the cytoplasm. These differences in staining patterns are not mutually exclusive and likely result from different expression levels, cell types, and use of fusion proteins. Together, these data are consistent with the notion that huBUB1 and huBUB3 exist together as components of a multi-protein kinetochore complex.

EXAMPLE 13 huBUB1 is a Protein Kinase

The huBUB1 gene product functions as a kinase which auto-phosphorylates in the presence of a labeled ATP substrate. This phosphorylation is an inherent activity of the huBUB1 protein, as demonstrated by a requirement for lysine 821 in the huBUB1kinase motif. In the context of a huBUB1/huBUB3 complex, only huBUB1 auto-phosphorylation was observed. This result is in contrast to that reported for S cerevisiae BUB1/BUB3 complexes (Roberts et al. 1994).

This result could be related to some requirement for prior activation of huBUB1 before exogenous substrates (i.e., huBUB3) are phosphorylated. We therefore tested the activity of the huBUB1 kinase towards a variety of test proteins, and identified PHAS-I as an in vitro substrate of the huBUB1kinase. Absence of huBUB3 phosphorylation in kinase reactions could therefore not be attributed to any inability of huBUB1 to phosphorylate exogenous substrates. We tested the idea that the FLAG epitope tag might alter the activity of huBUB3 as a substrate. Although HA-huBUB1 efficiently retains both huBUB3 and FLAG-huBUB3, only HA-huBUB1 auto-phosphorylation was observed in kinase reactions containing these proteins. Thus, we conclude that under these conditions huBUB3 is not a significant huBUB1 substrate.

In other experiments, we did not detect any requirement for huBUB3 association for huBUB1 kinase activity. HA-huBUB1 prepared in the absence of cotranslated huBUB3 functions as an auto-phosphorylating kinase. Co-translation of huBUB3 sufficient to produce stoichiometric huBUB1/huBUB3 association did not reproducibly stimulate or inhibit huBUB1 auto-phosphorylation. These results are similar to those reported in S. cerevisiae, where BUB1 auto-phosphorylation was observed in extracts prepared from strains carrying a deletion of the BUB3 gene (Roberts et al.).

Relevant substrates of the huBUB1 kinase might include the human homolog of the S. cerevisiae MAD1 protein, which is phosphorylated in the presence of microtubule poisons (Jin et al. 1998). In S. cerevisiae, this phosphorylation has been attributed to the MPS1 kinase (Hardwick et al. 1996). The human kinase ttk (Mills et al. 1992) exhibits structural similarity to the MPS1 gene (see Sorger et al. 1997), and therefore also represents a candidate human MAD1 kinase. We find that ttk exhibits a tissue-specific mRNA expression pattern very similar to that of huBUB1 and MAD2 (FIG. 5).

Other BUB/MAD phosphorylation substrates may include the apoptosis inhibitor protein Bcl-2 and the kinase c-raf, each reported to be phosphorylated in mammalian cells treated with microtubule poisons (Blagosklonny et al. 1996; Haldar et al. 1996). BUB/MAD-mediated regulation of Bcl-2 may explain the apoptotic effects of microtubule poisons. In HeLa cells expressing an N-terminal domain of murine BUB1, this apoptotic effect is blocked (Taylor and McKeon 1997), suggesting that apoptosis is a downstream component of BUB/MAD signaling in human cells. Apoptotic death may be one cellular response to prolonged mitotic arrests caused by microtubule poisons. Indeed, enrichment of huBUB1mutations in tumors may occur due to the ability of cells to escape apoptotic death caused by induction of the BUB/MAD signaling pathway, as might occur during cancer chemotherapeutic drug treatment or by stochastic errors of chromosome segregation experienced by rapidly dividing cells. Phosphorylation of c-raf may represent a means whereby growth regulatory signals are linked to BUB/MAD-mediated cell cycle regulation.

REFERENCES

Blagosklonny et al., Taxol-induced apoptosis and phosphorylation of Bcl-2 protein involves c- Raf-1 and represents a novel c-Raf-1 signal transduction pathway. *Cancer Res* 56:1851–54 (1996).

Cahill et al., Mutations of mitotic checkpoint genes in human cancers. *Nature* 39: 300–03 (1998).

Haldar et al. Taxol induces bcl-2 phosphorylation and death of prostate cancer cells. *Cancer Res* 56:1253–55 (1996).

Hardwick et al., Activation of the budding yeast spindle assembly checkpoint without mitotic spindle disruption. *Science* 273: 953–56 (1996).

Jin et al., Human T cell leukemia virus type 1 oncoprotein Tax targets the human mitotic checkpoint protein MAD1. *Cell* 93: 81–91 (1998).

Mills et al., Expression of TTK, a novel human protein kinase, is associated with cell proliferation. *J. Biol Chem* 267: 16000–06 (1992).

Pangilinan et al., Mammalian BUB1 protein kinases: map positions and in vivo. *Genomics* 46: 379–88 (1997).

Roberts et al., The *Saccharomyces cerevisiae* checkpoint gene BUB1 encodes a novel protein kinase. *Mol Cell Biol* 14: 8282–91 (1994).

Sorger et al., Coupling cell division and cell death to microtubule dynamics. *Curr Opin Cell Biol* 9: 807–14 (1997).

Taylor et al., The Human Homologue of Bub3 is Required for Kinetochore Localization of Bub1 and a Mad3/Bub1-related Protein Kinase. *J Cell Biol* 142:1–11 (1998).

Taylor & McKeon, Kinetochore localization of murine Bub1 is required for normal mitotic timing and checkpoint response to spindle damage. *Cell* 89: 727–735 (1997).

What is claimed is:

1. A polynucleotide which encodes a huBUB3 protein comprising an amino acid sequence of SEQ ID NO:2.

2. The polynucleotide of claim 1 comprising the nucleotide sequence of SEQ ID NO:1.

3. A construct comprising:
   a promoter; and
   a polynucleotide segment encoding a huBUB3 protein as shown in SEQ ID NO:2, wherein the polynucleotide segment is located downstream from the promoter, wherein transcription of the polynucleotide segment initiates at the promoter.

4. A host cell comprising a construct which comprises:
   a promoter and;
   a polynucleotide segment encoding a huBUB3 protein comprising an amino acid sequence as shown in SEQ ID NO:2.

5. A recombinant host cell comprising a new transcription initiation unit, wherein the new transcription initiation unit comprises in 5' to 3' order:
   (a) an exogenous regulatory sequence;
   (b) an exogenous exon; and
   (c) a splice donor site,
wherein the new transcription initiation unit is located upstream of a coding sequence of a huBUB3 gene as shown in SEQ ID NO:1, wherein the exogenous regulatory sequence controls transcription of the coding sequence of the huBUB3 gene.

* * * * *

SEQUENCE LISTING

```
<160> NUMBER OF SEQ ID NOS:  32

<210> SEQ ID NO 1
<211> LENGTH: 2619
<212> TYPE: DNA
<213> ORGANISM: Homo sapien

<400> SEQUENCE: 1
gaagcaagga ggcggcggcg gccgagcgag tggcgagtag tggaaacgtt gcttctgagg      60
ggagcccaag atgaccggtt ctaacgagtt caagctgaac cagccacccg aggatggcat     120
ctcctccgtg aagttcagcc ccaacacctc ccagttcctg cttgtctcct cctgggacac     180
gtccgtgcgt ctctacgatg tgccggccaa ctccatgcgg ctcaagtacc agcacaccgg     240
cgccgtcctg gactgcgcct tctacgatcc aacgcatgcc tggagtggag gactagatca     300
tcaattgaaa atgcatgatt tgaacactga tcaagaaaat cttgttggga cccatgatgc     360
ccctatcaga tgtgttgaat actgtccaga agtgaatgtg atggtcactg gaagttggga     420
tcagacagtt aaactgtggg atcccagaac tccttgtaat gctgggacct tctctcagcc     480
tgaaaaggta tatcccctct cagtgtctgg agaccggctg attgtgggaa cagcaggccg     540
cagagtgttg gtgtgggact tacggaacat gggttacgtg cagcagcgca gggagtccag     600
cctgaaatac cagactcgct gcatacgagc gtttccaaac aagcagggtt atgtattaag     660
ctctattgaa ggccgagtgg cagttgagta tttggaccca agccctgagg tacagaagaa     720
gaagtatgcc ttcaaatgtc acagactaaa agaaaataat attgagcaga tttacccagt     780
caatgccatt tcttttcaca atatccacaa tacatttgcc acaggtggtt ctgatggctt     840
tgtaaatatt tgggatccat ttaacaaaaa gcgactgtgc caattccatc ggtaccccac     900
gagcatcgca tcacttgcct tcagtaatga tgggactacg cttgcaatag cgtcatcata     960
tatgtatgaa atggatgaca cagaacatcc tgaagatggt atcttcattc gccaagtgac    1020
agatgcagaa acaaaaccca agtcaccatg tacttgacaa gatttcattt acttaagtgc    1080
catgttgatg ataataaaac aattcgtact ccccaatggt ggatttatta ctattaaaga    1140
aaccagggaa aatattaatt ttaatattat aacaacctga aaataatgga aaagaggttt    1200
ttgaattttt ttttttaaat aaacaccttc ttaagtgcat gagatggttt gatggtttgc    1260
tgcattaaag gtatttgggc aaacaaaatt ggagggcaag tgactgcagt tttgagaatc    1320
agttttgacc ttgatgattt tttgtttcca ctgtggaaat aaatgtttgt aaataagtgt    1380
aataaaaatc cctttgcatt ctttctggac cttaaatggt agaggaaaag gctcgtgagc    1440
```

-continued

```
catttgtttc ttttgctggt tatagttgct aattctaaag ctgcttcaga ctgcttcatg    1500
aggaggttaa tctacaatta aacaatattt cctcttggcc gtccattatt ttctgaagca    1560
gatggttcat catttcctgg gctgttaaac aaagcgaggt taaggttaga ctcttgggaa    1620
tcagctagtt ttcaatctta ttagggtgca gaaggaaaac taataagaaa acctcctaat    1680
atcattttgt gactgtaaac aattatttat tagcaaacaa ttgatcccag aagggcaaat    1740
tgtttgagtc agtaatgagc tgagaaaaga cagagcatat ctgtgtattt ggaaaaataa    1800
ttgtaacgta attgcagtgc atttagacag gcatctattt ggacctgttt ctatctctaa    1860
atgaattttt ggaaacatta atgaggttta catatttctc tgacatttat atagttctta    1920
tgtccatttc agttgaccag ccgctggtga ttaaagttaa aaagaaaaaa attatagtga    1980
gaatgagatt catttcaatg taatgcacta agcagaaca cgaacttagc ttggcctatt    2040
ctaggtagtt ccaaatagta ttttgttgt caaactttaa aatttatatt aatttgcaaa    2100
tgtatgtctc tgagtaggac ttggaccttt cctgagattt attttatccg tgatgtattt    2160
tttttaattc ttttgataca gagaagggtc tttttttttt taagtatttc agtgaaaact    2220
tggtgtaagt ctgaacccat cttttgaaat gtattttctt cattgcaggt ccacctaatc    2280
atcctgtgaa agtggtttct ctatggaaag ctttgtttgc ttcctacaaa tacatgctta    2340
ttccttaagg gatgtgttag agttactgtg gatttctctg ttttctgtct tacaagaaac    2400
ttgtctatgt accttaatac tttgtttagg atgaggagtc tttgtgtccc tgtacagtag    2460
tctgacgtat ttccccttct gtcccctagt aagcccagtt gctgtatctg aacagtttga    2520 gctcttttg taatatactc taaacctgtt atttctgtgc taataaacga gatgcagaac    2580
ccttgaaaaa aaaaaaaaaa aaaaaaaaa aaaaaaaa                             2619
```

<210> SEQ ID NO 2
<211> LENGTH: 328
<212> TYPE: PRT
<213> ORGANISM: Homo sapien

<400> SEQUENCE: 2

```
Met Thr Gly Ser Asn Glu Phe Lys Leu Asn Gln Pro Pro Glu Asp Gly
 1               5                  10                  15

Ile Ser Ser Val Lys Phe Ser Pro Asn Thr Ser Gln Phe Leu Leu Val
                20                  25                  30

Ser Ser Trp Asp Thr Ser Val Arg Leu Tyr Asp Val Pro Ala Asn Ser
        35                  40                  45

Met Arg Leu Lys Tyr Gln His Thr Gly Ala Val Leu Asp Cys Ala Phe
    50                  55                  60

Tyr Asp Pro Thr His Ala Trp Ser Gly Gly Leu Asp His Gln Leu Lys
65                  70                  75                  80

Met His Asp Leu Asn Thr Asp Gln Glu Asn Leu Val Gly Thr His Asp
                85                  90                  95

Ala Pro Ile Arg Cys Val Glu Tyr Cys Pro Glu Val Asn Val Met Val
               100                 105                 110

Thr Gly Ser Trp Asp Gln Thr Val Lys Leu Trp Asp Pro Arg Thr Pro
            115                 120                 125

Cys Asn Ala Gly Thr Phe Ser Gln Pro Glu Lys Val Tyr Thr Leu Ser
        130                 135                 140

Val Ser Gly Asp Arg Leu Ile Val Gly Thr Ala Gly Arg Arg Val Leu
145                 150                 155                 160
```

```
Val Trp Asp Leu Arg Asn Met Gly Tyr Val Gln Gln Arg Arg Glu Ser
                165                 170                 175
Ser Leu Lys Tyr Gln Thr Arg Cys Ile Arg Ala Phe Pro Asn Lys Gln
                180                 185                 190
Gly Tyr Val Leu Ser Ser Ile Glu Gly Arg Val Ala Val Glu Tyr Leu
                195                 200                 205
Asp Pro Ser Pro Glu Val Gln Lys Lys Tyr Ala Phe Lys Cys His
            210                 215                 220
Arg Leu Lys Glu Asn Asn Ile Glu Gln Ile Tyr Pro Val Asn Ala Ile
225                 230                 235                 240
Ser Phe His Asn Ile His Asn Thr Phe Ala Thr Gly Gly Ser Asp Gly
                245                 250                 255
Phe Val Asn Ile Trp Asp Pro Phe Asn Lys Lys Arg Leu Cys Gln Phe
                260                 265                 270
His Arg Tyr Pro Thr Ser Ile Ala Ser Leu Ala Phe Ser Asn Asp Gly
                275                 280                 285
Thr Thr Leu Ala Ile Ala Ser Ser Tyr Met Tyr Glu Met Asp Asp Thr
                290                 295                 300
Glu His Pro Glu Asp Gly Ile Phe Ile Arg Gln Val Thr Asp Ala Glu
305                 310                 315                 320
Thr Lys Pro Lys Ser Pro Cys Thr
                325

<210> SEQ ID NO 3
<211> LENGTH: 3441
<212> TYPE: DNA
<213> ORGANISM: Homo sapien

<400> SEQUENCE: 3
caggtttggc cgctgccggc cagcgtcctc tggccatgga caccccggaa aatgtccttc      60
agatgcttga agcccacatg cagagctaca agggcaatga ccctcttggt gaatgggaaa    120
gatacataca gtgggtagaa gagaattttc ctgagaataa agaatacttg ataactttac    180
tagaacattt aatgaaggaa tttttagata agaagaaata ccacaatgac ccaagattca    240
tcagttattg tttaaaattt gctgagtaca acagtgacct ccatcaattt tttgagtttc    300
tgtacaacca tgggattgga accctgtcat cccctctgta cattgcctgg gcggggcatc    360
tggaagccca aggagagctg cagcatgcca gtgctgtcct tcagagagga attcaaaacc    420
aggctgaacc cagagagttc ctgcaacaac aatacaggtt atttcagaca cgcctcactg    480
aaacccattt gccagctcaa gctagaacct cagaacctct gcataatgtt caggttttaa    540
atcaaatgat aacatcaaaa tcaaatccag gaaataacat ggcctgcatt tctaagaatc    600
agggttcaga gctttctgga gtgatatctt cagcttgtga taagagtca aatatggaac    660 gaagagtgat cacgatttct aaatcagaat attctgtgca ctcatctttg gcatccaaag    720
ttgatgttga gcaggttgtt atgtattgca aggagaagct tattcgtggg gaatcagaat    780
tttcctttga agaattgaga gcccagaaat acaatcaacg gagaaagcat gagcaatggg    840
taaatgaaga cagacattat atgaaaagga agaagcaaa tgcttttgaa gaacagctat    900
taaaacagaa aatggatgaa cttcataaga gttgcatca ggtggtggag acatcccatg    960
aggatctgcc cgcttcccag gaaaggtccg aggttaatcc agcacgtatg gggccaagtg   1020
taggctccca gcaggaactg agagcgccat gtcttccagt aacctatcag cagacaccag   1080
tgaacatgga aaagaaccca agagaggcac ctcctgttgt tcctcctttg gcaaatgcta   1140
```

-continued

| | |
|---|---|
| tttctgcagc tttggtgtcc ccagccacca gccagagcat tgctcctcct gttcctttga | 1200 |
| aagcccagac agtaacagac tccatgtttg cagtggccag caaagatgct ggatgtgtga | 1260 |
| ataagagtac tcatgaattc aagccacaga gtggagcaga gatcaaagaa gggtgtgaaa | 1320 |
| cacataaggt tgccaacaca agttcttttc acacaactcc aaacacatca ctgggaatgg | 1380 |
| ttcaggcaac gccatccaaa gtgcagccat cacccaccgt gcacacaaaa gaagcattag | 1440 |
| gtttcatcat gaatatgttt caggctccta cacttcctga tatttctgat gacaaagatg | 1500 |
| aatggcaatc tctagatcaa aatgaagatg catttgaagc ccagtttcaa aaaatgtaa | 1560 |
| ggtcatctgg ggcttgggga gtcaataaga tcatctcttc tttgtcatct gcttttcatg | 1620 |
| tgtttgaaga tggaaacaaa gaaaattatg gattaccaca gcctaaaaat aaacccacag | 1680 |
| gagccaggac ctttggagaa cgctctgtca gcagacttcc ttcaaaacca aggaggaag | 1740 |
| tgcctcatgc tgaagagttt ttggatgact caactgtatg gggtattcgc tgcaacaaaa | 1800 |
| ccctggcacc cagtcctaag agcccaggag acttcacatc tgctgcacaa cttgcgtcta | 1860 |
| caccattcca caagcttcca gtggagtcag tgcacatttt agaagataaa gaaaatgtgg | 1920 |
| tagcaaaaca gtgtacccag gcgactttgg attcttgtga ggaaacatg gtggtgcctt | 1980 |
| caagggatgg aaaattcagt ccaattcaag agaaaagccc aaaacaggcc ttgtcgtctc | 2040 |
| acatgtattc agcatcctta cttcgtctga gccagcctgc tgcaggtggg gtacttacct | 2100 |
| gtgaggcaga gttgggcgtt gaggcttgca gactcacaga cactgacgct gccattgcag | 2160 |
| aagatccacc agatgctatt gctgggctcc aagcagaatg gatgcagatg agttcacttg | 2220 |
| ggactgttga tgctccaaac ttcattgttg ggaacccatg ggatgataag ctgattttca | 2280 |
| aactttatc tgggctttct aaaccagtga gttcctatcc aaatactttt gaatggcaat | 2340 |
| gtaaacttcc agccatcaag cccaagactg aatttcaatt gggttctaag ctggtctatg | 2400 |
| tccatcacct tcttggagaa ggagcctttg cccaggtgta cgaagctacc cagggagatc | 2460 |
| tgaatgatgc taaaaataaa cagaaatttg ttttaaaggt ccaaaagcct gccaacccct | 2520 |
| gggaattcta cattgggacc cagttgatgg aaagactaaa gccatctatg cagcacatgt | 2580 |
| ttatgaagtt ctattctgcc cacttattcc agaatggcag tgtattagta ggagagctct | 2640 |
| acagctatgg aacattatta aatgccatta acctctataa aaatacccct gaaaagtga | 2700 |
| tgcctcaagg tcttgtcatc tcttttgcta tgagaatgct ttacatgatt gagcaagtgc | 2760 |
| atgactgtga aatcattcat ggagacatta accagacaa tttcatactt ggaaacggat | 2820 |
| ttttggaaca ggatgatgaa gatgatttat ctgctggctt ggcactgatt gacctgggtc | 2880 |
| agagtataga tatgaaactt tttccaaaag gaactatatt cacagcaaag tgtgaaacat | 2940 |
| ctggttttca gtgtgttgag atgctcagca acaaaccatg gaactaccag atcgattact | 3000 |
| ttgggggttgc tgcaacagta tattgcatgc tctttggcac ttacatgaaa gtgaaaaatg | 3060 |
| aaggaggaga gtgtaagcct gaaggtcttt ttagaaggct tcctcatttg gatatgtgga | 3120 |
| atgaattttt tcatgttatg ttgaatattc cagattgtca tcatcttcca tctttggatt | 3180 |
| tgttaaggca aaagctgaag aaagtatttc aacaacacta tactaacaag attagggccc | 3240 |
| tacgtaatag gctaattgta ctgctcttag aatgtaagcg ttcacgaaaa taaaatttgg | 3300 |
| atatagacag tccttaaaaa tcacactgta aatatgaatc tgctcacttt aaacctgttt | 3360 |
| ttttttcatt tattgtttat gtaaatgttt gttaaaaata aatcccatgg aatatttcca | 3420 |
| tgtaaaaaaa aaaaaaaaa a | 3441 |

<210> SEQ ID NO 4
<211> LENGTH: 1085
<212> TYPE: PRT
<213> ORGANISM: Homo sapien

<400> SEQUENCE: 4

```
Met Asp Thr Pro Glu Asn Val Leu Gln Met Leu Glu Ala His Met Gln
 1               5                  10                  15

Ser Tyr Lys Gly Asn Asp Pro Leu Gly Glu Trp Glu Arg Tyr Ile Gln
            20                  25                  30

Trp Val Glu Glu Asn Phe Pro Glu Asn Lys Glu Tyr Leu Ile Thr Leu
        35                  40                  45

Leu Glu His Leu Met Lys Glu Phe Leu Asp Lys Lys Lys Tyr His Asn
50                  55                  60

Asp Pro Arg Phe Ile Ser Tyr Cys Leu Lys Phe Ala Glu Tyr Asn Ser
65                  70                  75                  80

Asp Leu His Gln Phe Phe Glu Phe Leu Tyr Asn His Gly Ile Gly Thr
                85                  90                  95

Leu Ser Ser Pro Leu Tyr Ile Ala Trp Ala Gly His Leu Glu Ala Gln
            100                 105                 110

Gly Glu Leu Gln His Ala Ser Ala Val Leu Gln Arg Gly Ile Gln Asn
        115                 120                 125

Gln Ala Glu Pro Arg Glu Phe Leu Gln Gln Gln Tyr Arg Leu Phe Gln
130                 135                 140

Thr Arg Leu Thr Glu Thr His Leu Pro Ala Gln Ala Arg Thr Ser Glu
145                 150                 155                 160

Pro Leu His Asn Val Gln Val Leu Asn Gln Met Ile Thr Ser Lys Ser
                165                 170                 175

Asn Pro Gly Asn Asn Met Ala Cys Ile Ser Lys Asn Gln Gly Ser Glu
            180                 185                 190

Leu Ser Gly Val Ile Ser Ser Ala Cys Asp Lys Glu Ser Asn Met Glu
        195                 200                 205

Arg Arg Val Ile Thr Ile Ser Lys Ser Glu Tyr Ser Val His Ser Ser
210                 215                 220

Leu Ala Ser Lys Val Asp Val Glu Gln Val Val Met Tyr Cys Lys Glu
225                 230                 235                 240

Lys Leu Ile Arg Gly Glu Ser Glu Phe Ser Phe Glu Glu Leu Arg Ala
                245                 250                 255

Gln Lys Tyr Asn Gln Arg Arg Lys His Glu Gln Trp Val Asn Glu Asp
            260                 265                 270

Arg His Tyr Met Lys Arg Lys Glu Ala Asn Ala Phe Glu Glu Gln Leu
        275                 280                 285

Leu Lys Gln Lys Met Asp Glu Leu His Lys Lys Leu His Gln Val Val
290                 295                 300

Glu Thr Ser His Glu Asp Leu Pro Ala Ser Gln Glu Arg Ser Glu Val
305                 310                 315                 320

Asn Pro Ala Arg Met Gly Pro Ser Val Gly Ser Gln Gln Glu Leu Arg
                325                 330                 335

Ala Pro Cys Leu Pro Val Thr Tyr Gln Gln Thr Pro Val Asn Met Glu
            340                 345                 350

Lys Asn Pro Arg Glu Ala Pro Val Val Pro Leu Ala Asn Ala
        355                 360                 365

Ile Ser Ala Ala Leu Val Ser Pro Ala Thr Ser Gln Ser Ile Ala Pro
370                 375                 380
```

```
Pro Val Pro Leu Lys Ala Gln Thr Val Thr Asp Ser Met Phe Ala Val
385                 390                 395                 400

Ala Ser Lys Asp Ala Gly Cys Val Asn Lys Ser Thr His Glu Phe Lys
            405                 410                 415

Pro Gln Ser Gly Ala Glu Ile Lys Glu Gly Cys Glu Thr His Lys Val
            420                 425                 430

Ala Asn Thr Ser Ser Phe His Thr Thr Pro Asn Thr Ser Leu Gly Met
            435                 440                 445

Val Gln Ala Thr Pro Ser Lys Val Gln Pro Ser Pro Thr Val His Thr
    450                 455                 460

Lys Glu Ala Leu Gly Phe Ile Met Asn Met Phe Gln Ala Pro Thr Leu
465                 470                 475                 480

Pro Asp Ile Ser Asp Asp Lys Asp Glu Trp Gln Ser Leu Asp Gln Asn
                485                 490                 495

Glu Asp Ala Phe Glu Ala Gln Phe Gln Lys Asn Val Arg Ser Ser Gly
            500                 505                 510

Ala Trp Gly Val Asn Lys Ile Ile Ser Ser Leu Ser Ser Ala Phe His
            515                 520                 525

Val Phe Glu Asp Gly Asn Lys Glu Asn Tyr Gly Leu Pro Gln Pro Lys
    530                 535                 540

Asn Lys Pro Thr Gly Ala Arg Thr Phe Gly Arg Ser Val Ser Arg
545                 550                 555                 560

Leu Pro Ser Lys Pro Lys Glu Val Pro His Ala Glu Glu Phe Leu
            565                 570                 575

Asp Asp Ser Thr Val Trp Gly Ile Arg Cys Asn Lys Thr Leu Ala Pro
            580                 585                 590

Ser Pro Lys Ser Pro Gly Asp Phe Thr Ser Ala Ala Gln Leu Ala Ser
    595                 600                 605

Thr Pro Phe His Lys Leu Pro Val Glu Ser Val His Ile Leu Glu Asp
    610                 615                 620

Lys Glu Asn Val Val Ala Lys Gln Cys Thr Gln Ala Thr Leu Asp Ser
625                 630                 635                 640

Cys Glu Glu Asn Met Val Val Pro Ser Arg Asp Gly Lys Phe Ser Pro
            645                 650                 655

Ile Gln Glu Lys Ser Pro Lys Gln Ala Leu Ser Ser His Met Tyr Ser
            660                 665                 670

Ala Ser Leu Leu Arg Leu Ser Gln Pro Ala Ala Gly Val Leu Thr
            675                 680                 685

Cys Glu Ala Glu Leu Gly Val Glu Ala Cys Arg Leu Thr Asp Thr Asp
690                 695                 700

Ala Ala Ile Ala Glu Asp Pro Pro Asp Ala Ile Ala Gly Leu Gln Ala
705                 710                 715                 720

Glu Trp Met Gln Met Ser Ser Leu Gly Thr Val Asp Ala Pro Asn Phe
            725                 730                 735

Ile Val Gly Asn Pro Trp Asp Asp Lys Leu Ile Phe Lys Leu Leu Ser
            740                 745                 750

Gly Leu Ser Lys Pro Val Ser Ser Tyr Pro Asn Thr Phe Glu Trp Gln
            755                 760                 765

Cys Lys Leu Pro Ala Ile Lys Pro Lys Thr Glu Phe Gln Leu Gly Ser
            770                 775                 780

Lys Leu Val Tyr Val His His Leu Leu Gly Glu Gly Ala Phe Ala Gln
785                 790                 795                 800

Val Tyr Glu Ala Thr Gln Gly Asp Leu Asn Asp Ala Lys Asn Lys Gln
```

```
                           805                 810                 815
Lys Phe Val Leu Lys Val Gln Lys Pro Ala Asn Pro Trp Glu Phe Tyr
                820                 825                 830
Ile Gly Thr Gln Leu Met Glu Arg Leu Lys Pro Ser Met Gln His Met
            835                 840                 845
Phe Met Lys Phe Tyr Ser Ala His Leu Phe Gln Asn Gly Ser Val Leu
        850                 855                 860
Val Gly Glu Leu Tyr Ser Tyr Gly Thr Leu Leu Asn Ala Ile Asn Leu
865                 870                 875                 880
Tyr Lys Asn Thr Pro Glu Lys Val Met Pro Gln Gly Leu Val Ile Ser
                885                 890                 895
Phe Ala Met Arg Met Leu Tyr Met Ile Glu Gln Val His Asp Cys Glu
                900                 905                 910
Ile Ile His Gly Asp Ile Lys Pro Asp Asn Phe Ile Leu Gly Asn Gly
            915                 920                 925
Phe Leu Glu Gln Asp Asp Glu Asp Leu Ser Ala Gly Leu Ala Leu
        930                 935                 940
Ile Asp Leu Gly Gln Ser Ile Asp Met Lys Leu Phe Pro Lys Gly Thr
945                 950                 955                 960
Ile Phe Thr Ala Lys Cys Glu Thr Ser Gly Phe Gln Cys Val Glu Met
                965                 970                 975
Leu Ser Asn Lys Pro Trp Asn Tyr Gln Ile Asp Tyr Phe Gly Val Ala
                980                 985                 990
Ala Thr Val Tyr Cys Met Leu Phe Gly Thr Tyr Met Lys Val Lys Asn
            995                 1000                1005
Glu Gly Gly Glu Cys Lys Pro Glu Gly Leu Phe Arg Arg Leu Pro His
        1010                1015                1020
Leu Asp Met Trp Asn Glu Phe Phe His Val Met Leu Asn Ile Pro Asp
1025                1030                1035                1040
Cys His His Leu Pro Ser Leu Asp Leu Leu Arg Gln Lys Leu Lys Lys
                1045                1050                1055
Val Phe Gln Gln His Tyr Thr Asn Lys Ile Arg Ala Leu Arg Asn Arg
                1060                1065                1070
Leu Ile Val Leu Leu Leu Glu Cys Lys Arg Ser Arg Lys
            1075                1080                1085

<210> SEQ ID NO 5
<211> LENGTH: 21
<212> TYPE: DNA
<213> ORGANISM: Artificial Sequence
<220> FEATURE:
<223> OTHER INFORMATION: Sense PCR primer

<400> SEQUENCE: 5
gggagcccaa gatgaccggt t                                           21

<210> SEQ ID NO 6
<211> LENGTH: 28
<212> TYPE: DNA
<213> ORGANISM: Artificial Sequence
<220> FEATURE:
<223> OTHER INFORMATION: Antisense PCR primer

<400> SEQUENCE: 6
aaatccacca ttggggagta cgaattgt                                    28

<210> SEQ ID NO 7
```

```
<211> LENGTH: 27
<212> TYPE: DNA
<213> ORGANISM: Artificial Sequence
<220> FEATURE:
<223> OTHER INFORMATION: Antisense  PCR primer

<400> SEQUENCE: 7
ccctgcttgt ttggaaacgc tcgtatg                                27

<210> SEQ ID NO 8
<211> LENGTH: 27
<212> TYPE: DNA
<213> ORGANISM: Artificial Sequence
<220> FEATURE:
<223> OTHER INFORMATION: PCR primer

<400> SEQUENCE: 8
cgggtggctg gttcagcttg aactcgt                                27

<210> SEQ ID NO 9
<211> LENGTH: 5
<212> TYPE: DNA
<213> ORGANISM: Unknown
<220> FEATURE:
<223> OTHER INFORMATION: Consensus sequence

<400> SEQUENCE: 9 caagg                                                         5

<210> SEQ ID NO 10
<211> LENGTH: 10
<212> TYPE: DNA
<213> ORGANISM: Homo sapien

<400> SEQUENCE: 10
ccaagatgac                                                   10

<210> SEQ ID NO 11
<211> LENGTH: 26
<212> TYPE: DNA
<213> ORGANISM: Artificial Sequence
<220> FEATURE:
<223> OTHER INFORMATION: PCR primer

<400> SEQUENCE: 11
accctctcag tgtctggaga ccggct                                 26

<210> SEQ ID NO 12
<211> LENGTH: 28
<212> TYPE: DNA
<213> ORGANISM: Artificial Sequence
<220> FEATURE:
<223> OTHER INFORMATION: PCR primer

<400> SEQUENCE: 12
cgacggtttc caaacaagca gggttatg                               28

<210> SEQ ID NO 13
<211> LENGTH: 30
<212> TYPE: DNA
<213> ORGANISM: Artificial Sequence
<220> FEATURE:
<223> OTHER INFORMATION: PCR primer

<400> SEQUENCE: 13
tgatgataat aaaacaattc gtactcccca                             30
```

<210> SEQ ID NO 14
<211> LENGTH: 29
<212> TYPE: DNA
<213> ORGANISM: Artificial Sequence
<220> FEATURE:
<223> OTHER INFORMATION: PCR primer

<400> SEQUENCE: 14
gactcaaaca atttgccctt ctgggatca                              29

<210> SEQ ID NO 15
<211> LENGTH: 27
<212> TYPE: DNA
<213> ORGANISM: Artificial Sequence
<220> FEATURE:
<223> OTHER INFORMATION: Sense PCR primer

<400> SEQUENCE: 15
ggagcccaag atgaccggtt ctaacga                                27

<210> SEQ ID NO 16
<211> LENGTH: 10
<212> TYPE: DNA
<213> ORGANISM: Homo sapien

<400> SEQUENCE: 16
ccaagtcacc                                                   10

<210> SEQ ID NO 17
<211> LENGTH: 10
<212> TYPE: DNA
<213> ORGANISM: Homo sapien

<400> SEQUENCE: 17
tgcaggtcca                                                   10

<210> SEQ ID NO 18
<211> LENGTH: 38
<212> TYPE: DNA
<213> ORGANISM: Artificial Sequence
<220> FEATURE:
<223> OTHER INFORMATION: PCR primer

<400> SEQUENCE: 18
tcattgcagg tccacctaat catcctgtga aagtggtt                    38

<210> SEQ ID NO 19
<211> LENGTH: 35
<212> TYPE: DNA
<213> ORGANISM: Artificial Sequence
<220> FEATURE:
<223> OTHER INFORMATION: PCR primer

<400> SEQUENCE: 19
actaggggac agaaggggaa atacgtcaga ctact                       35

<210> SEQ ID NO 20
<211> LENGTH: 31
<212> TYPE: DNA
<213> ORGANISM: Artificial Sequence
<220> FEATURE:
<223> OTHER INFORMATION: PCR primer

<400> SEQUENCE: 20

-continued

```
tttgggcaaa caaaattgga gggcaagtga c                           31
```

<210> SEQ ID NO 21
<211> LENGTH: 32
<212> TYPE: DNA
<213> ORGANISM: Artificial Sequence
<220> FEATURE:
<223> OTHER INFORMATION: PCR primer

<400> SEQUENCE: 21

```
accagcaaaa gaaacaaatg gctcacgagc ct                          32
```

<210> SEQ ID NO 22
<211> LENGTH: 34
<212> TYPE: DNA
<213> ORGANISM: Artificial Sequence
<220> FEATURE:
<223> OTHER INFORMATION: PCR primer

<400> SEQUENCE: 22

```
tgcaggtcca cctaatcatc ctgtgaaagt ggtt                        34
```

<210> SEQ ID NO 23
<211> LENGTH: 35
<212> TYPE: DNA
<213> ORGANISM: Artificial Sequence
<220> FEATURE:
<223> OTHER INFORMATION: PCR primer

<400> SEQUENCE: 23

```
acagaagggg aaatacgtca gactactgta caggg                       35
```

<210> SEQ ID NO 24
<211> LENGTH: 7
<212> TYPE: PRT
<213> ORGANISM: Homo sapien

<400> SEQUENCE: 24

```
Asp Tyr Lys Asp Asp Asp Lys
 1               5
```

<210> SEQ ID NO 25
<211> LENGTH: 35
<212> TYPE: DNA
<213> ORGANISM: Artificial Sequence
<220> FEATURE:
<223> OTHER INFORMATION: PCR primer

<400> SEQUENCE: 25

```
accaagaggg tcattgccct tgtagctctg catgt                       35
```

<210> SEQ ID NO 26
<211> LENGTH: 35
<212> TYPE: DNA
<213> ORGANISM: Artificial Sequence
<220> FEATURE:
<223> OTHER INFORMATION: PCR primer

<400> SEQUENCE: 26

```
ggatgcagag ttctctggga gctctgtggc tgatt                       35
```

<210> SEQ ID NO 27
<211> LENGTH: 330
<212> TYPE: PRT
<213> ORGANISM: Homo sapien

<400> SEQUENCE: 27

```
Met Thr Gly Ser Asn Glu Phe Lys Leu Asn Gln Pro Pro Glu Asp Gly
 1               5                  10                  15
Ile Ser Ser Val Lys Phe Ser Pro Asn Thr Ser Gln Phe Leu Leu Val
                20                  25                  30
Ser Ser Trp Asp Thr Ser Val Arg Leu Tyr Asp Val Pro Ala Asn Ser
            35                  40                  45
Met Arg Leu Lys Tyr Gln His Thr Gly Ala Val Leu Asp Cys Ala Phe
 50                  55                  60
Tyr Asp Pro Thr His Ala Trp Ser Gly Gly Leu Asp His Gln Leu Lys
 65                  70                  75                  80
Met His Asp Leu Asn Thr Asp Gln Glu Asn Leu Val Gly Thr His Asp
                85                  90                  95
Ala Pro Ile Arg Cys Val Glu Tyr Cys Pro Glu Val Asn Val Met Val
            100                 105                 110
Thr Gly Ser Trp Asp Gln Thr Val Lys Leu Trp Asp Pro Arg Thr Pro
        115                 120                 125
Cys Asn Ala Gly Thr Phe Ser Gln Pro Glu Lys Val Tyr Thr Leu Ser
130                 135                 140
Val Ser Gly Asp Arg Leu Ile Val Gly Thr Ala Gly Arg Arg Val Leu
145                 150                 155                 160
Val Trp Asp Leu Arg Asn Met Gly Tyr Val Gln Gln Arg Arg Glu Ser
                165                 170                 175
Ser Leu Lys Tyr Gln Thr Arg Cys Ile Arg Ala Phe Pro Asn Lys Gln
            180                 185                 190
Gly Tyr Val Leu Ser Ser Ile Glu Gly Arg Val Ala Val Glu Tyr Leu
        195                 200                 205
Asp Pro Ser Pro Glu Val Gln Lys Lys Tyr Ala Phe Lys Cys His
210                 215                 220
Arg Leu Lys Glu Asn Asn Ile Glu Gln Ile Tyr Pro Val Asn Ala Ile
225                 230                 235                 240
Ser Phe His Asn Ile His Asn Thr Phe Ala Thr Gly Gly Ser Asp Gly
                245                 250                 255
Phe Val Asn Ile Trp Asp Pro Phe Asn Lys Lys Arg Leu Cys Gln Phe
            260                 265                 270
His Arg Tyr Pro Thr Ser Ile Ala Ser Leu Ala Phe Ser Asn Asp Gly
        275                 280                 285
Thr Thr Leu Ala Ile Ala Ser Ser Tyr Met Tyr Glu Met Asp Asp Thr
290                 295                 300
Glu His Pro Glu Asp Gly Ile Phe Ile Arg Gln Val Thr Asp Ala Glu
305                 310                 315                 320
Thr Lys Pro Lys Val His Leu Ile Ile Leu
                325                 330
```

<210> SEQ ID NO 28
<211> LENGTH: 341
<212> TYPE: PRT
<213> ORGANISM: Saccharomyces cerevisiae

<400> SEQUENCE: 28

```
Met Gln Ile Val Gln Ile Glu Gln Ala Pro Lys Asp Tyr Ile Ser Asp
 1               5                  10                  15
Ile Lys Ile Ile Pro Ser Lys Ser Leu Leu Leu Ile Thr Ser Trp Asp
                20                  25                  30
```

```
Gly Ser Leu Thr Val Tyr Lys Phe Asp Ile Gln Ala Lys Asn Val Asp
             35                  40                  45

Leu Leu Gln Ser Leu Arg Tyr Lys His Pro Leu Leu Cys Cys Asn Phe
 50                  55                  60

Ile Asp Asn Thr Asp Leu Gln Ile Tyr Val Gly Thr Val Gln Gly Glu
 65                  70                  75                  80

Ile Leu Lys Val Asp Leu Ile Gly Ser Pro Ser Phe Gln Ala Leu Thr
                 85                  90                  95

Asn Asn Glu Ala Asn Leu Gly Ile Cys Arg Ile Cys Lys Tyr Gly Asp
            100                 105                 110

Asp Lys Leu Ile Ala Ala Ser Trp Asp Gly Leu Ile Glu Val Ile Asp
            115                 120                 125

Pro Arg Asn Tyr Gly Asp Gly Val Ile Ala Val Lys Asn Leu Asn Ser
            130                 135                 140

Asn Asn Thr Lys Val Lys Asn Lys Ile Phe Thr Met Asp Thr Asn Ser
145                 150                 155                 160

Ser Arg Leu Ile Val Gly Met Asn Asn Ser Gln Val Gln Trp Phe Arg
                165                 170                 175

Leu Pro Leu Cys Glu Asp Asp Asn Gly Thr Ile Glu Glu Ser Gly Leu
            180                 185                 190

Lys Tyr Gln Ile Arg Asp Val Ala Leu Leu Pro Lys Glu Gln Glu Gly
            195                 200                 205

Tyr Ala Cys Ser Ser Ile Asp Gly Arg Val Ala Val Glu Phe Phe Asp
            210                 215                 220

Asp Gln Gly Asp Asp Tyr Asn Ser Ser Lys Arg Phe Ala Phe Arg Cys
225                 230                 235                 240

His Arg Leu Asn Leu Lys Asp Thr Asn Leu Ala Tyr Pro Val Asn Ser
                245                 250                 255

Ile Glu Phe Ser Pro Arg His Lys Phe Leu Tyr Thr Ala Gly Ser Asp
            260                 265                 270

Gly Ile Ile Ser Cys Trp Asn Leu Gln Thr Arg Lys Lys Ile Lys Asn
            275                 280                 285

Phe Ala Lys Phe Asn Glu Asp Ser Val Val Lys Ile Ala Cys Ser Asp
            290                 295                 300

Asn Ile Leu Cys Leu Ala Thr Ser Asp Asp Thr Phe Lys Thr Asn Ala
305                 310                 315                 320

Ala Ile Asp Gln Thr Ile Glu Leu Asn Ala Ser Ser Ile Tyr Ile Ile
                325                 330                 335

Phe Asp Tyr Glu Asn
            340

<210> SEQ ID NO 29
<211> LENGTH: 326
<212> TYPE: PRT
<213> ORGANISM: Mus musculus

<400> SEQUENCE: 29

Met Thr Gly Ser Asn Glu Phe Lys Leu Asn Gln Pro Pro Glu Asp Gly
 1               5                  10                  15

Ile Ser Ser Val Lys Phe Ser Pro Asn Thr Ser Gln Phe Leu Leu Val
                 20                  25                  30

Ser Ser Trp Asp Thr Ser Val Arg Leu Tyr Asp Val Pro Ala Asn Ser
             35                  40                  45

Met Arg Leu Lys Tyr Gln His Thr Gly Ala Val Leu Asp Cys Ala Phe
 50                  55                  60
```

```
Tyr Asp Pro Thr His Ala Trp Ser Gly Gly Leu Asp His Gln Leu Lys
 65                  70                  75                  80

Met His Asp Leu Asn Thr Asp Gln Glu Asn Leu Val Gly Thr His Asp
             85                  90                  95

Ala Pro Ile Arg Cys Val Glu Tyr Cys Pro Glu Val Asn Val Met Val
            100                 105                 110

Thr Gly Ser Trp Asp Gln Thr Val Lys Leu Trp Asp Pro Arg Thr Pro
            115                 120                 125

Cys Asn Ala Gly Thr Phe Ser Gln Pro Glu Lys Val Tyr Thr Leu Ser
130                 135                 140

Val Ser Gly Asp Arg Leu Ile Val Gly Thr Ala Gly Arg Arg Val Leu
145                 150                 155                 160

Val Trp Asp Leu Trp Asn Met Gly Tyr Val Gln Gln Arg Arg Glu Ser
                165                 170                 175

Ser Leu Lys Tyr Gln Thr Arg Cys Ile Arg Ala Phe Pro Asn Lys Gln
            180                 185                 190

Gly Tyr Val Leu Ser Ser Ile Glu Gly Arg Val Ala Val Glu Tyr Leu
            195                 200                 205

Asp Pro Ser Pro Glu Val Gln Lys Lys Tyr Ala Phe Lys Cys His
210                 215                 220

Arg Leu Lys Glu Asn Asn Ile Glu Gln Ile Tyr Pro Val Asn Ala Ile
225                 230                 235                 240

Ser Phe His Asn Ile His Asn Thr Phe Ala Thr Gly Gly Ser Asp Gly
                245                 250                 255

Phe Val Asn Ile Trp Asp Pro Phe Asn Lys Lys Arg Leu Cys Gln Phe
            260                 265                 270

His Arg Tyr Pro Thr Ser Ile Ala Ser Leu Ala Phe Ser Asn Asp Gly
            275                 280                 285

Thr Thr Leu Ala Ile Ala Ser Ser Tyr Met Tyr Glu Met Asp Asp Thr
            290                 295                 300

Glu His Pro Glu Asp Gly Ile Phe Ile Arg Gln Val Thr Asp Ala Glu
305                 310                 315                 320

Thr Lys Pro Lys Ser Thr
                325

<210> SEQ ID NO 30
<211> LENGTH: 368
<212> TYPE: PRT
<213> ORGANISM: Homo sapien

<400> SEQUENCE: 30

Met Ser Leu Phe Gly Thr Thr Ser Gly Phe Gly Thr Ser Gly Thr Ser
  1               5                  10                  15

Met Phe Gly Ser Ala Thr Thr Asp Asn His Asn Pro Met Lys Asp Ile
             20                  25                  30

Glu Val Thr Ser Ser Pro Asp Asp Ser Ile Gly Cys Leu Ser Phe Ser
             35                  40                  45

Pro Pro Thr Leu Pro Gly Asn Phe Leu Ile Ala Gly Ser Trp Ala Asn
 50                  55                  60

Asp Val Arg Cys Trp Glu Val Gln Asp Ser Gly Gln Thr Ile Pro Lys
 65                  70                  75                  80

Ala Gln Gln Met His Thr Gly Pro Val Leu Asp Val Cys Trp Ser Asp
             85                  90                  95

Asp Gly Ser Lys Val Phe Thr Ala Ser Cys Asp Lys Thr Ala Lys Met
```

-continued

```
                100             105             110
Trp Asp Leu Ser Ser Asn Gln Ala Ile Gln Ile Ala Gln His Asp Ala
            115                 120                 125
Pro Val Lys Thr Ile His Trp Ile Lys Ala Pro Asn Tyr Ser Cys Val
130                 135                 140
Met Thr Gly Ser Trp Asp Lys Thr Leu Lys Phe Trp Asp Thr Arg Ser
145                 150                 155                 160
Ser Asn Pro Met Met Val Leu Gln Leu Pro Glu Arg Cys Tyr Cys Ala
                165                 170                 175
Asp Val Ile Tyr Pro Met Ala Val Ala Thr Ala Glu Arg Gly Leu
            180                 185                 190
Ile Val Tyr Gln Leu Glu Asn Gln Pro Ser Glu Phe Arg Arg Ile Glu
            195                 200                 205
Ser Pro Leu Lys His Gln His Arg Cys Val Ala Ile Phe Lys Asp Lys
            210                 215                 220
Gln Asn Lys Pro Thr Gly Phe Ala Leu Gly Ser Ile Glu Gly Arg Val
225                 230                 235                 240
Ala Ile His Tyr Ile Asn Pro Pro Asn Pro Ala Lys Asp Asn Phe Thr
                245                 250                 255
Phe Lys Cys His Arg Ser Asn Gly Thr Asn Thr Ser Ala Pro Gln Asp
                260                 265                 270
Ile Tyr Ala Val Asn Gly Ile Ala Phe His Pro Val His Gly Thr Leu
            275                 280                 285
Ala Thr Val Gly Ser Asp Gly Arg Phe Ser Phe Trp Asp Lys Asp Ala
            290                 295                 300
Arg Thr Lys Leu Lys Thr Ser Glu Gln Leu Asp Gln Pro Ile Ser Ala
305                 310                 315                 320
Cys Cys Phe Asn His Asn Gly Asn Ile Phe Ala Tyr Ala Ser Ser Tyr
                325                 330                 335
Asp Trp Ser Lys Gly His Glu Phe Tyr Asn Pro Gln Lys Lys Asn Tyr
            340                 345                 350
Ile Phe Leu Arg Asn Ala Ala Glu Glu Leu Lys Pro Arg Asn Lys Lys
            355                 360                 365
```

<210> SEQ ID NO 31
<211> LENGTH: 352
<212> TYPE: PRT
<213> ORGANISM: Schizosaccharomyces pombe

<400> SEQUENCE: 31

```
Met Ser Leu Phe Gly Gln Ala Thr Thr Ser Thr Val Ser Asn Ala Thr
1               5                   10                  15
Gly Asp Leu Lys Lys Asp Val Glu Val Ala Gln Pro Pro Glu Asp Ser
            20                  25                  30
Ile Ser Asp Leu Ala Phe Ser Pro Gln Ala Glu Tyr Leu Ala Ala Ser
            35                  40                  45
Ser Trp Asp Ser Lys Val Arg Ile Tyr Glu Val Gln Ala Thr Gly Gln
        50                  55                  60
Ser Ile Gly Lys Ala Leu Tyr Glu His Gln Gly Pro Val Leu Ser Val
65                  70                  75                  80
Asn Trp Ser Arg Asp Gly Thr Lys Val Ala Ser Gly Ser Val Asp Lys
                85                  90                  95
Ser Ala Lys Val Phe Asp Ile Gln Thr Gly Gln Asn Gln Gln Val Ala
                100                 105                 110
```

```
Ala His Asp Asp Ala Val Arg Cys Val Arg Phe Val Glu Ala Met Gly
        115                 120                 125

Thr Ser Pro Ile Leu Ala Thr Gly Ser Trp Asp Lys Thr Leu Lys Tyr
    130                 135                 140

Trp Asp Leu Arg Gln Ser Thr Pro Ile Ala Thr Val Ser Leu Pro Glu
145                 150                 155                 160

Arg Val Tyr Ala Met Asp Cys Val His Pro Leu Leu Thr Val Ala Thr
                165                 170                 175

Ala Glu Arg Asn Ile Cys Val Ile Asn Leu Ser Glu Pro Thr Lys Ile
            180                 185                 190

Phe Lys Leu Ala Met Ser Pro Leu Lys Phe Gln Thr Arg Ser Leu Ala
        195                 200                 205

Cys Phe Ile Lys Gly Asp Gly Tyr Ala Ile Gly Ser Val Glu Gly Arg
    210                 215                 220

Cys Ala Ile Gln Asn Ile Asp Glu Lys Asn Ala Ser Gln Asn Phe Ser
225                 230                 235                 240

Phe Arg Cys His Arg Asn Gln Ala Gly Asn Ser Ala Asp Val Tyr Ser
                245                 250                 255

Val Asn Ser Ile Ala Phe His Pro Gln Tyr Gly Thr Phe Ser Thr Ala
            260                 265                 270

Gly Ser Asp Gly Thr Phe Ser Phe Trp Asp Lys Asp Ser His Gln Arg
        275                 280                 285

Leu Lys Ser Tyr Pro Asn Val Gly Gly Thr Ile Ser Cys Ser Thr Phe
    290                 295                 300

Asn Arg Thr Gly Asp Ile Phe Ala Tyr Ala Ile Ser Tyr Asp Trp Ser
305                 310                 315                 320

Lys Gly Tyr Thr Phe Asn Asn Ala Gln Leu Pro Asn Lys Ile Met Leu
                325                 330                 335

His Pro Val Pro Gln Asp Glu Ile Lys Pro Arg Pro Lys Lys Gly Arg
            340                 345                 350

<210> SEQ ID NO 32
<211> LENGTH: 365
<212> TYPE: PRT
<213> ORGANISM: Saccharomyces cerevisiae

<400> SEQUENCE: 32

Met Ser Phe Phe Asn Arg Ser Asn Thr Thr Ser Ala Leu Gly Thr Ser
1               5                   10                  15

Thr Ala Met Ala Asn Glu Lys Asp Leu Ala Asn Asp Ile Val Ile Asn
            20                  25                  30

Ser Pro Ala Glu Asp Ser Ile Ser Asp Ile Ala Phe Ser Pro Gln Gln
        35                  40                  45

Asp Phe Met Phe Ser Ala Ser Trp Asp Gly Lys Val Arg Ile Trp
50                  55                  60

Asp Val Gln Asn Gly Val Pro Gln Gly Arg Ala Gln His Glu Ser Ser
65                  70                  75                  80

Ser Pro Val Leu Cys Thr Arg Trp Ser Asn Asp Gly Thr Lys Val Ala
                85                  90                  95

Ser Gly Gly Cys Asp Asn Ala Leu Lys Leu Tyr Asp Ile Ala Ser Gly
            100                 105                 110

Gln Thr Gln Gln Ile Gly Met His Ser Ala Pro Ile Lys Val Leu Arg
        115                 120                 125

Phe Val Gln Cys Gly Pro Ser Asn Thr Glu Cys Ile Val Thr Gly Ser
    130                 135                 140
```

-continued

```
Trp Asp Lys Thr Ile Lys Tyr Trp Asp Met Arg Gln Pro Gln Pro Val
145                 150                 155                 160

Ser Thr Val Met Met Pro Glu Arg Val Tyr Ser Met Asp Asn Lys Gln
                165                 170                 175

Ser Leu Leu Val Val Ala Thr Ala Glu Arg His Ile Ala Ile Ile Asn
                180                 185                 190

Leu Ala Asn Pro Thr Thr Ile Phe Lys Ala Thr Thr Ser Pro Leu Lys
            195                 200                 205

Trp Gln Thr Arg Cys Val Ala Cys Tyr Asn Glu Ala Asp Gly Tyr Ala
            210                 215                 220

Ile Gly Ser Val Glu Gly Arg Cys Ser Ile Arg Tyr Ile Asp Asp Gly
225                 230                 235                 240

Met Gln Lys Lys Ser Gly Phe Ser Phe Lys Cys His Arg Gln Thr Asn
                245                 250                 255

Pro Asn Arg Ala Pro Gly Ser Asn Gly Gln Ser Leu Val Tyr Pro Val
                260                 265                 270

Asn Ser Ile Ala Phe His Pro Leu Tyr Gly Thr Phe Val Thr Ala Gly
            275                 280                 285

Gly Asp Gly Thr Phe Asn Phe Trp Asp Lys Asn Gln Arg His Arg Leu
            290                 295                 300

Lys Gly Tyr Pro Thr Leu Gln Ala Ser Ile Pro Val Cys Ser Phe Asn
305                 310                 315                 320

Arg Asn Gly Ser Val Phe Ala Tyr Ala Leu Ser Tyr Asp Trp His Gln
                325                 330                 335

Gly His Met Gly Asn Arg Pro Asp Tyr Pro Asn Val Ile Arg Leu His
                340                 345                 350

Ala Thr Thr Asp Glu Glu Val Lys Glu Lys Lys Arg
            355                 360                 365
```